US008254637B2

(12) United States Patent
Abourizk et al.

(10) Patent No.: US 8,254,637 B2
(45) Date of Patent: Aug. 28, 2012

(54) MASK FITTING SYSTEM AND METHOD

(75) Inventors: Mark Alexander Abourizk, Boronia Park (AU); Paul Anthony Green, Lindfield (AU); Robert Edward Henry, Roseville (AU); Karthikeyan Selvarajan, Gosford (AU); Joanne Elizabeth Drew, Balgowiah Heights (AU)

(73) Assignee: ResMed Limited, Bella Vista (AU)

( * ) Notice: Subject to any disclaimer, the term of this patent is extended or adjusted under 35 U.S.C. 154(b) by 1090 days.

(21) Appl. No.: 11/878,798

(22) Filed: Jul. 26, 2007

(65) Prior Publication Data
US 2008/0060652 A1 Mar. 13, 2008

Related U.S. Application Data

(60) Provisional application No. 60/833,482, filed on Jul. 27, 2006, provisional application No. 60/840,003, filed on Aug. 25, 2006, provisional application No. 60/842,996, filed on Sep. 8, 2006.

(51) Int. Cl.
G06K 9/00 (2006.01)
G01B 11/24 (2006.01)

(52) U.S. Cl. ........ 382/106; 382/100; 382/118; 382/128; 382/141; 382/154; 356/601

(58) Field of Classification Search .................. None
See application file for complete search history.

(56) References Cited

U.S. PATENT DOCUMENTS

| 4,504,129 | A | 3/1985 | Van Iderstine |
| 4,825,068 | A | 4/1989 | Suzuki et al. |
| 5,284,313 | A | 2/1994 | Hallgren |
| 5,584,125 | A | 12/1996 | Prete |
| 5,771,310 | A | 6/1998 | Vannah |
| 6,017,315 | A | 1/2000 | Starr et al. |
| 6,397,847 | B1 | 6/2002 | Scarberry et al. |
| 6,546,309 | B1 * | 4/2003 | Gazzuolo ...................... 700/132 |
| 6,546,356 | B1 * | 4/2003 | Genest .......................... 702/153 |
| 6,728,589 | B1 * | 4/2004 | Delache et al. ................ 700/117 |
| 6,988,088 | B1 | 1/2006 | Miikkulainen et al. |
| 7,672,973 | B2 * | 3/2010 | Lordo ........................... 707/803 |

(Continued)

FOREIGN PATENT DOCUMENTS
EP 1 116 492 7/2001
(Continued)

OTHER PUBLICATIONS

Mortimore et al., "Comparison of nose and face mask CPAP therapy for sleep apnoea", Thorax, 1998; vol. 53, Issue 4, pp. 290-292.*

(Continued)

*Primary Examiner* — Tom Y Lu
*Assistant Examiner* — Thomas Conway
(74) *Attorney, Agent, or Firm* — Nixon & Vanderhye PC

(57) ABSTRACT

Systems and methods for selecting a mask system for a patient are provided. Certain example embodiments include generating 3D contours of patients and selecting mask systems based at least on these contours. These contours may be generated by using, for example, a cushion of translatable pins, a nasal cannular scanning device, and/or a shadow stereopsis sensor. Certain other example embodiments allow images and/or videos to be captured and optionally synchronized. Then, images of various mask systems may be overlaid to determine how well a mask system fits. In still other embodiments, a user can hold a transparency corresponding to a mask design in front of the patient's face to determine how well a mask system fits.

51 Claims, 49 Drawing Sheets

U.S. PATENT DOCUMENTS

| | | | |
|---|---|---|---|
| 7,827,038 B2 * | 11/2010 | Richard et al. | 705/2 |
| 2001/0004401 A1 | 6/2001 | Dubois et al. | |
| 2002/0188664 A1 | 12/2002 | Hultgren et al. | |
| 2004/0039592 A1 * | 2/2004 | Shima | 705/1 |
| 2004/0133604 A1 | 7/2004 | Lordo | |

FOREIGN PATENT DOCUMENTS

| | | |
|---|---|---|
| FR | 2 824 739 | 11/2002 |
| JP | 07-271964 | 10/1995 |
| JP | 08-010224 | 1/1996 |
| JP | 09-145324 | 6/1997 |
| JP | 2001-242094 | 9/2001 |
| WO | WO 00/59567 | 10/2000 |
| WO | WO 2004/037153 | 5/2004 |
| WO | PCT/AU2005/000810 | 6/2005 |

OTHER PUBLICATIONS

Respironics Mask Fitting Box "Contour Mask Fitting Kit—Reorder #302190", 1994, 1 page.
ResMed Product Specification, Doc. No. R1609-002, "Mask Fitting Template", 1995, 3 pages.
ResMed Brochure, "Clinical Equipment", 1997, 1 page.
ResMed Specification, Doc. No. 16954, "Disposable Mask Fitting Template" 1999, 3 pages.
ResMed Printed Material Specification, Doc. No. 16638, "Obsolete—Full Face Mask System—Fitting Template", 1999, 3 pages.
ResMed Printed Material Specification, Doc. No. 16956, "AWSL—Ultra Mirage Mask System—Fitting Template", 2001, 4 pages.
ResCare Blue Mask Fitting Template—Side 1, R169-002, 1 page.
ResCare Blue Mask Fitting Template—Side 2, R-169-002, 1 page.
Healthdyne Technologies, "The Softest, Silkiest CPAP Mask Available.", 2 pages.
ResCare Plastic Mask Fitting Template, 1 page.
ResCare Mask Fitting Template, 1 page.
Oct. 1997 Video of Mirage Mask System, 1 Compact Disc.
E2-DigiMask™ Nasal Version, "The effective Nasal CPAP Therapy Solution That Offers Many Key Benefits," (Aug. 2005), pp. 1-4.
SENSA SEAL™, User Application Instructions, Reusable Silicone Rubber Seal Accessory Attachment for the Hans Rudolph 7500 & 7600 Series Oro-Nasal Masks (2004), 2 pgs.
Hans Rudolph 7600 Series Oro-Nasal (Full Face) CPAP/NPPV Mask, Instructions for Use and Recommendations for Cleaning, Disinfection, Sterilization & Maintenance (2005), 6 pgs.
See http://www.cpap.com/cpap-mask-sizing.php, Mask Sizing guide, 4 pages.
E2-DigiMask™ Product Catalog, (12 pages) (Aug. 2005).
International Search Report for PCT/AU2005/000810 dated Jul. 4, 2005.
Nasal Pillow FAQ from cpap-pro.net, Oct. 14, 2005, 4 pages.
Best Full Face Mask, groups.google.com/group/alt.support.sleep-disorder, Oct. 13, 2005, 10 pages.
Help with autopap/ultra mirage, groups.google.com/group/alt.support.sleep-disorder, Oct. 13, 2005, 13 pages.
Sullivan Nasal CPAP Products, "Mask Systems Handbook", Sep. 1993, pp. 1-12.
Respironics "Nasal Mask Fitting Kit Instruction Card" with Nasal Mask Sizing Gauge, circa May 25, 1994, 1 page.
Respironics Mask Fitting Box, 1994, 1 page.
U.S. Appl. No. 10/556,461, filed Nov. 2005, Richard et al.
U.S. Appl. No. 60/619,951, filed Oct. 2004, Richard et al.
U.S. Appl. No. 60/576,621, filed Jun. 2004, Richard et al.
http://www-cpap.com/cpap-mask-sizing.php, Mask Sizing Guide, 2 pages [retrieved Jun. 3, 2011].
CPAP Machines and CPAP Masks for the Treatment of Sleep Apnea, "Mask Sizing Guide," retrieved Jan. 3, 2008, 4 pages. http://www.cpap.com/cpap-mask-sizing.php.
ResCare Blue Mask Fitting Template—Side 1, R169-002, 1 page, possibly as early as Jan. 1995.
ResCare Blue Mask Fitting Template—Side 2, R-169-002, 1 page, possibly as early as Jan. 1995.
Healthdyne Technologies, "The Softest, Silkiest CPAP Mask Available," 2 pages, at least as early as Jun. 21, 2006.
ResCare Plastic Mask Fitting Template, 1 page, at least as early as Jun. 21, 2006.
ResCare Mask Fitting Template, 1 page, at least as early as Jun. 21, 2006.

* cited by examiner

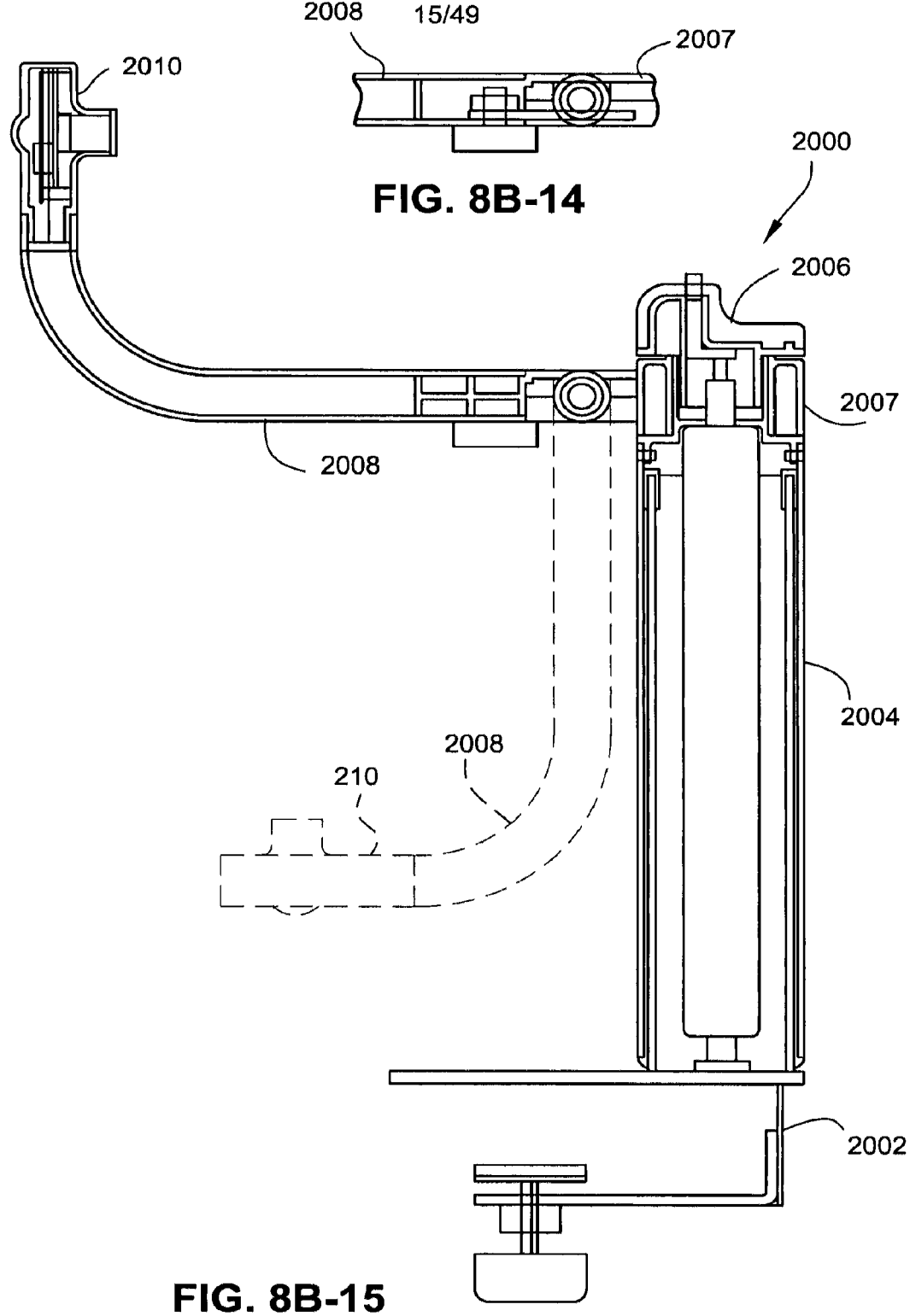

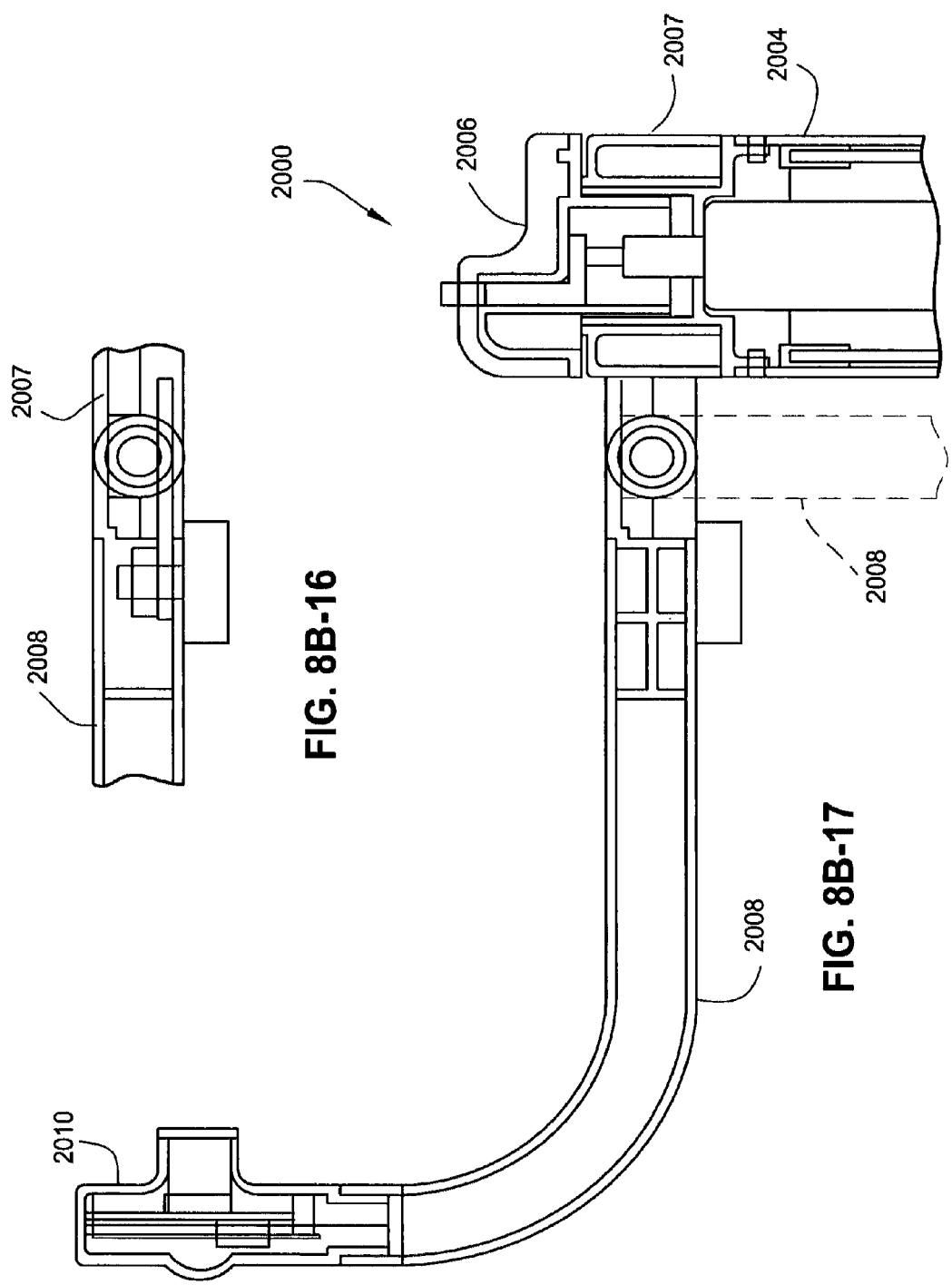

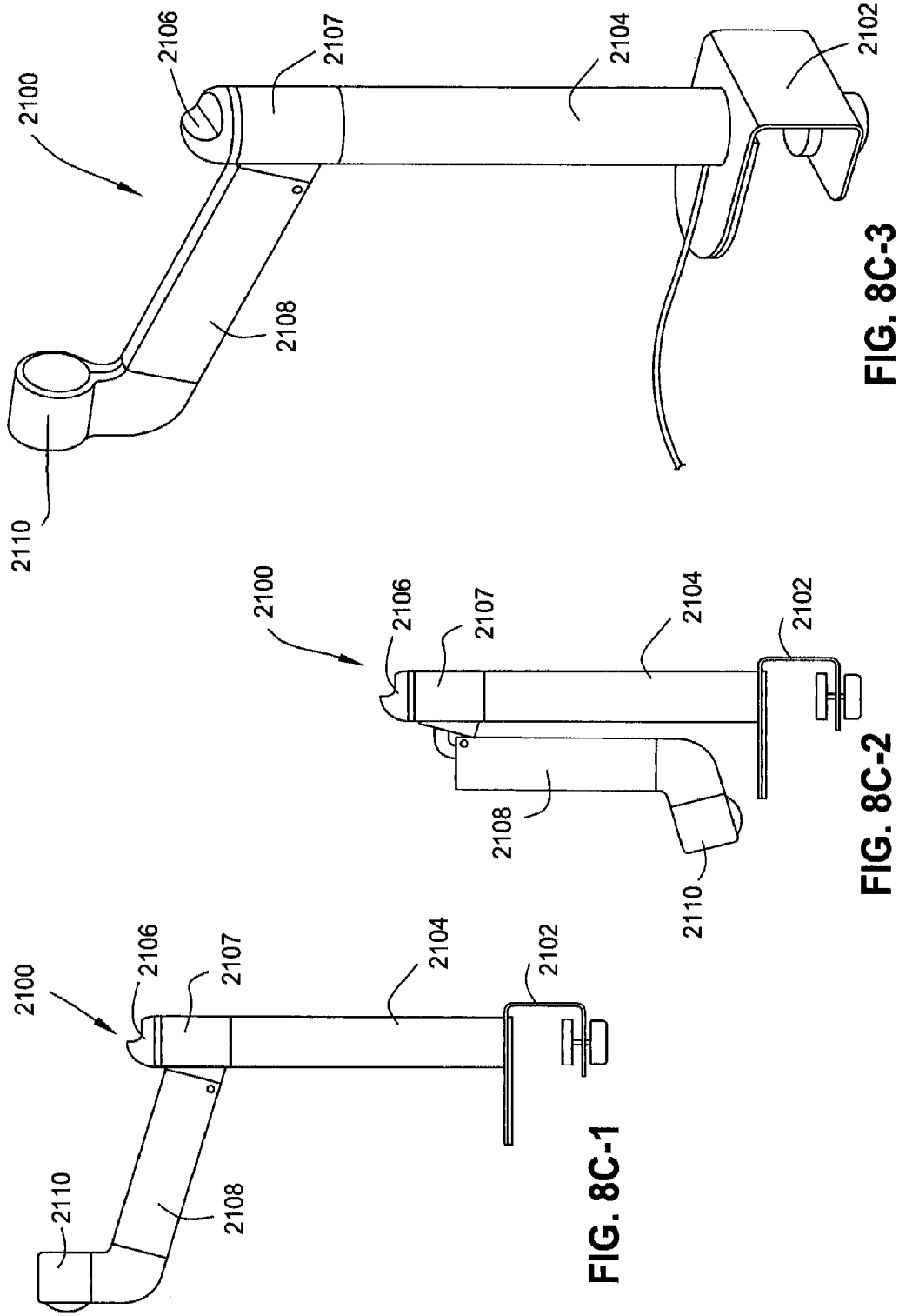

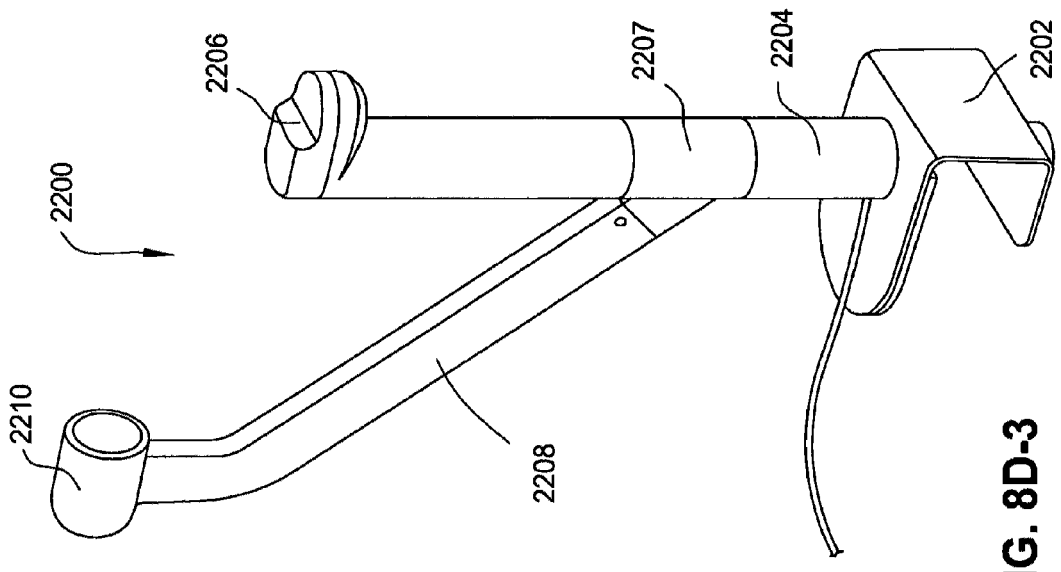
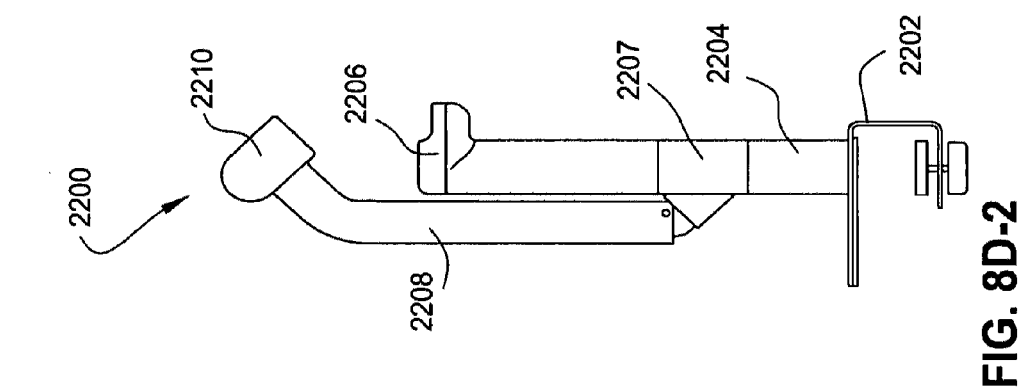
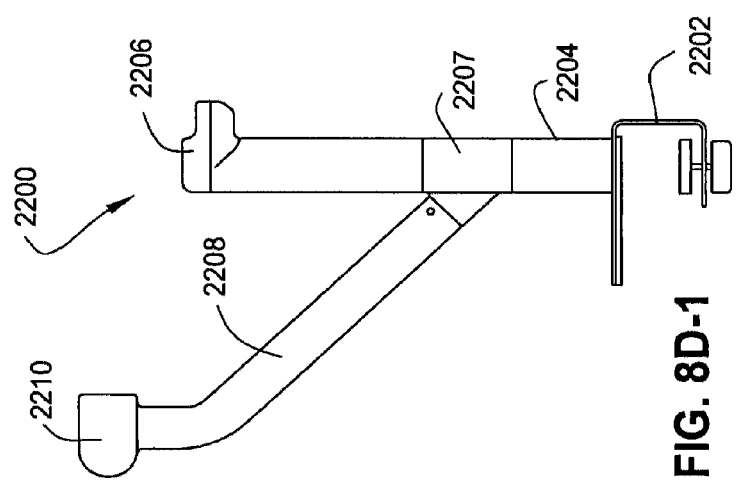
FIG. 8D-3
FIG. 8D-2
FIG. 8D-1

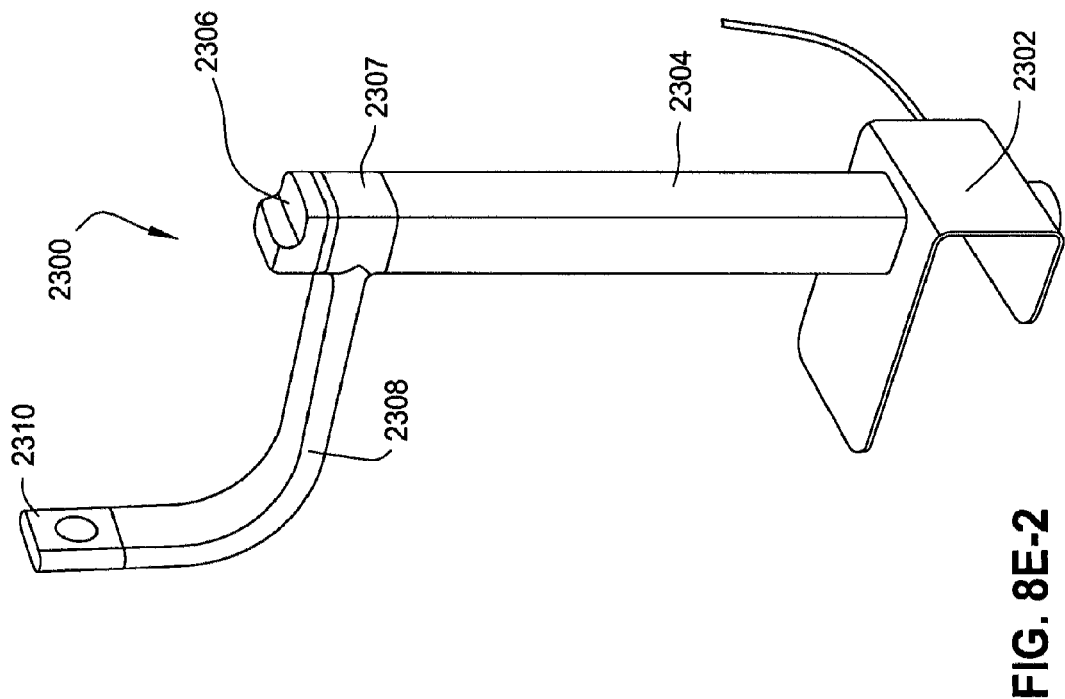
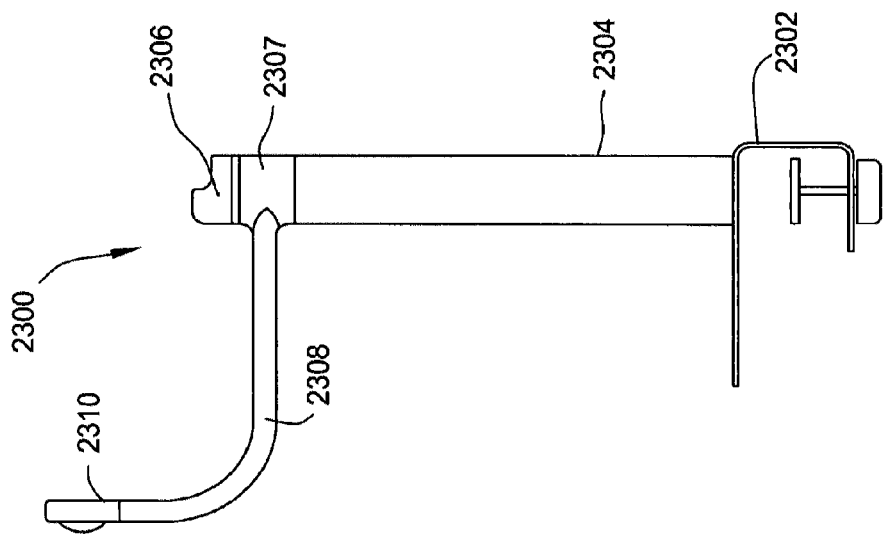
FIG. 8E-2
FIG. 8E-1

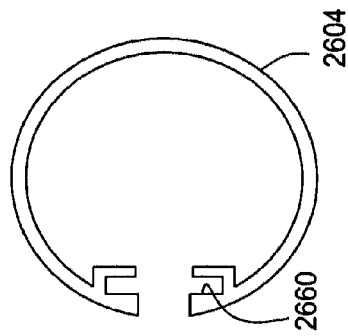
FIG. 8H-3
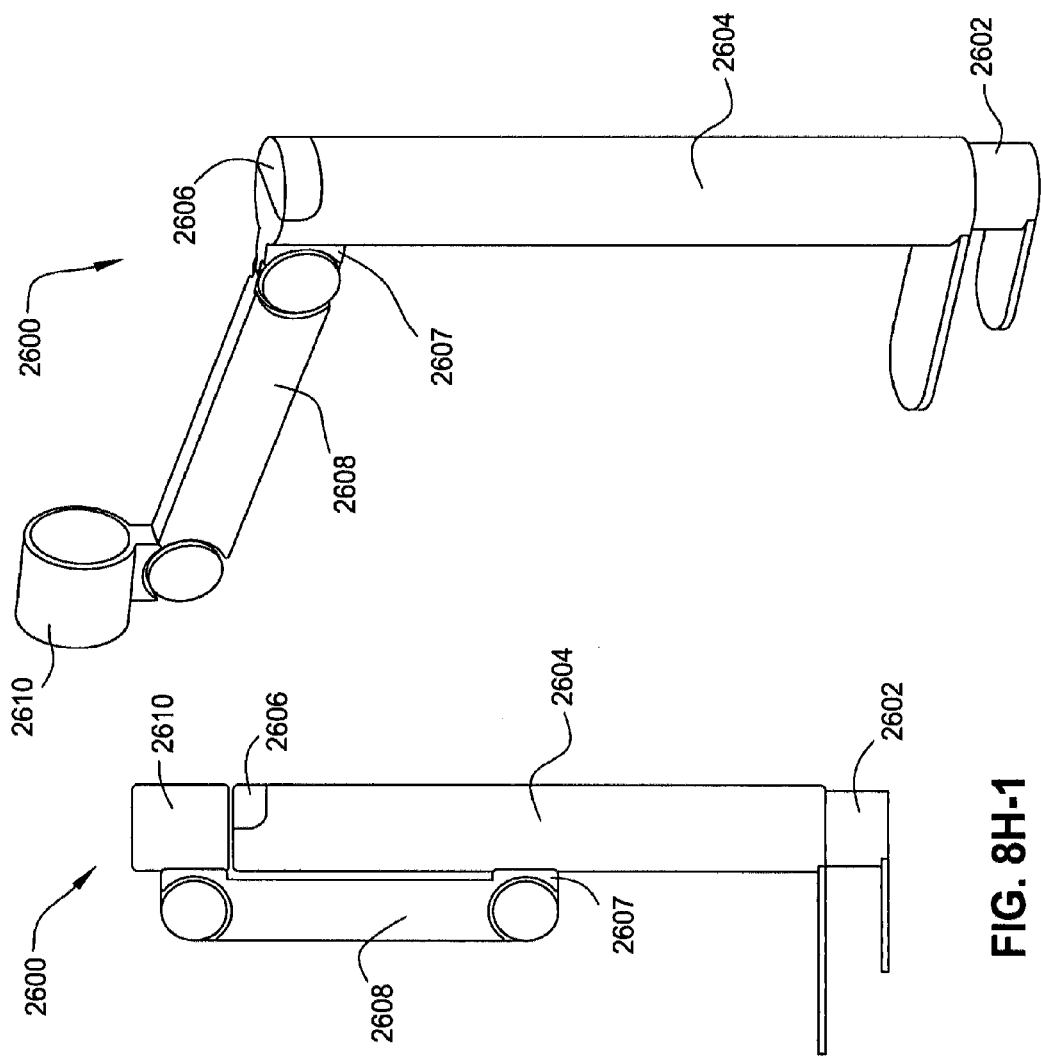
FIG. 8H-2
FIG. 8H-1

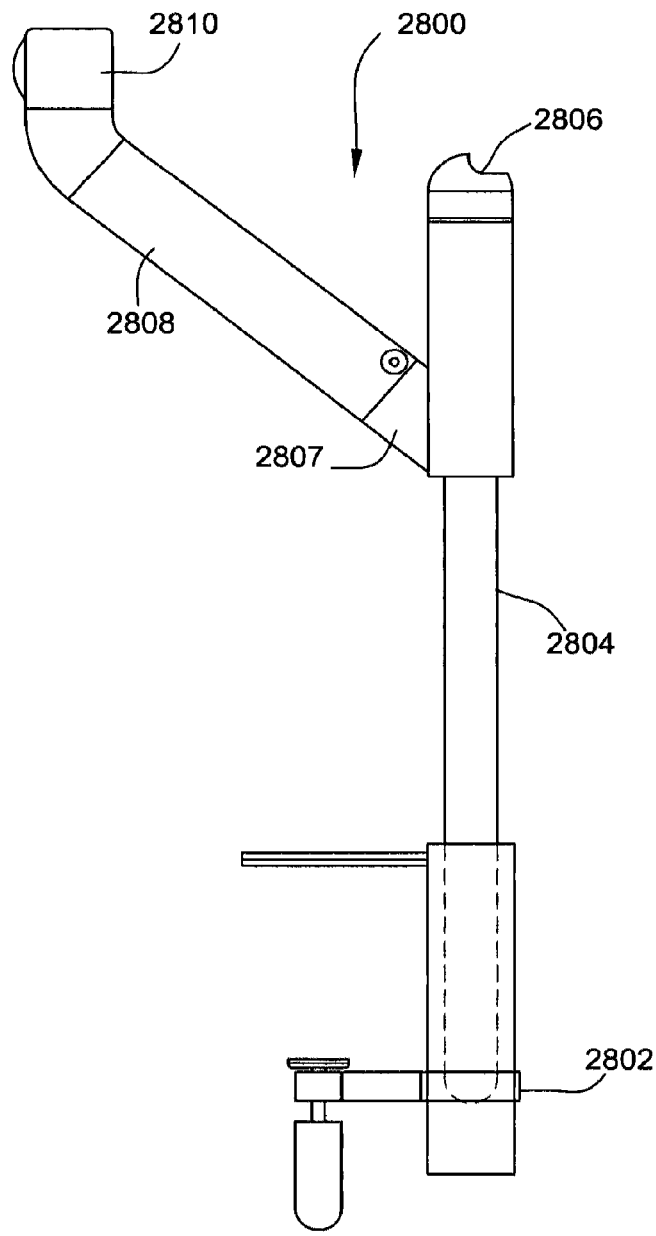
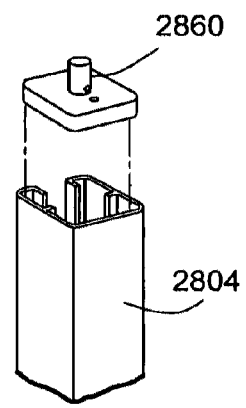
FIG. 8J-1
FIG. 8J-2

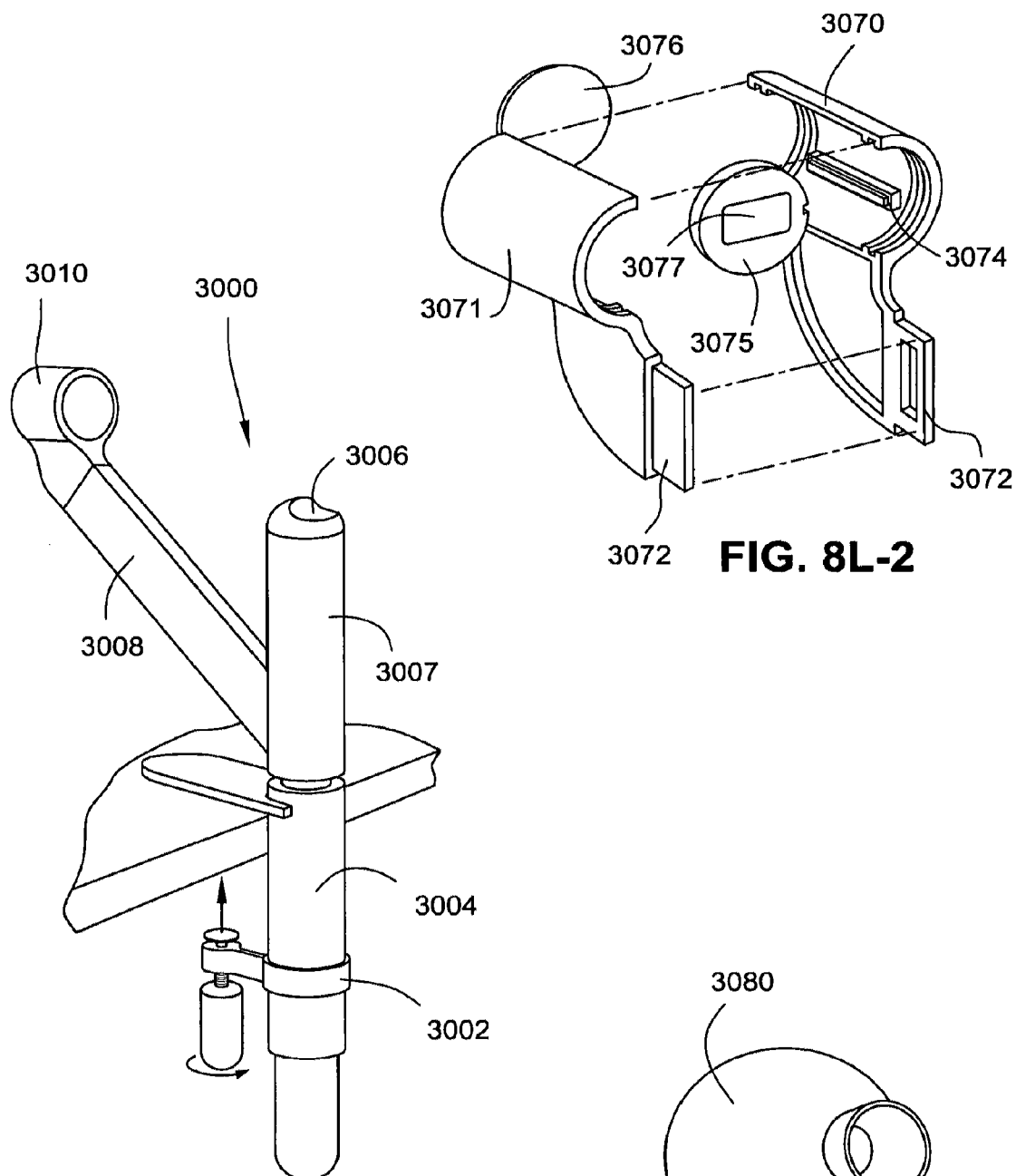

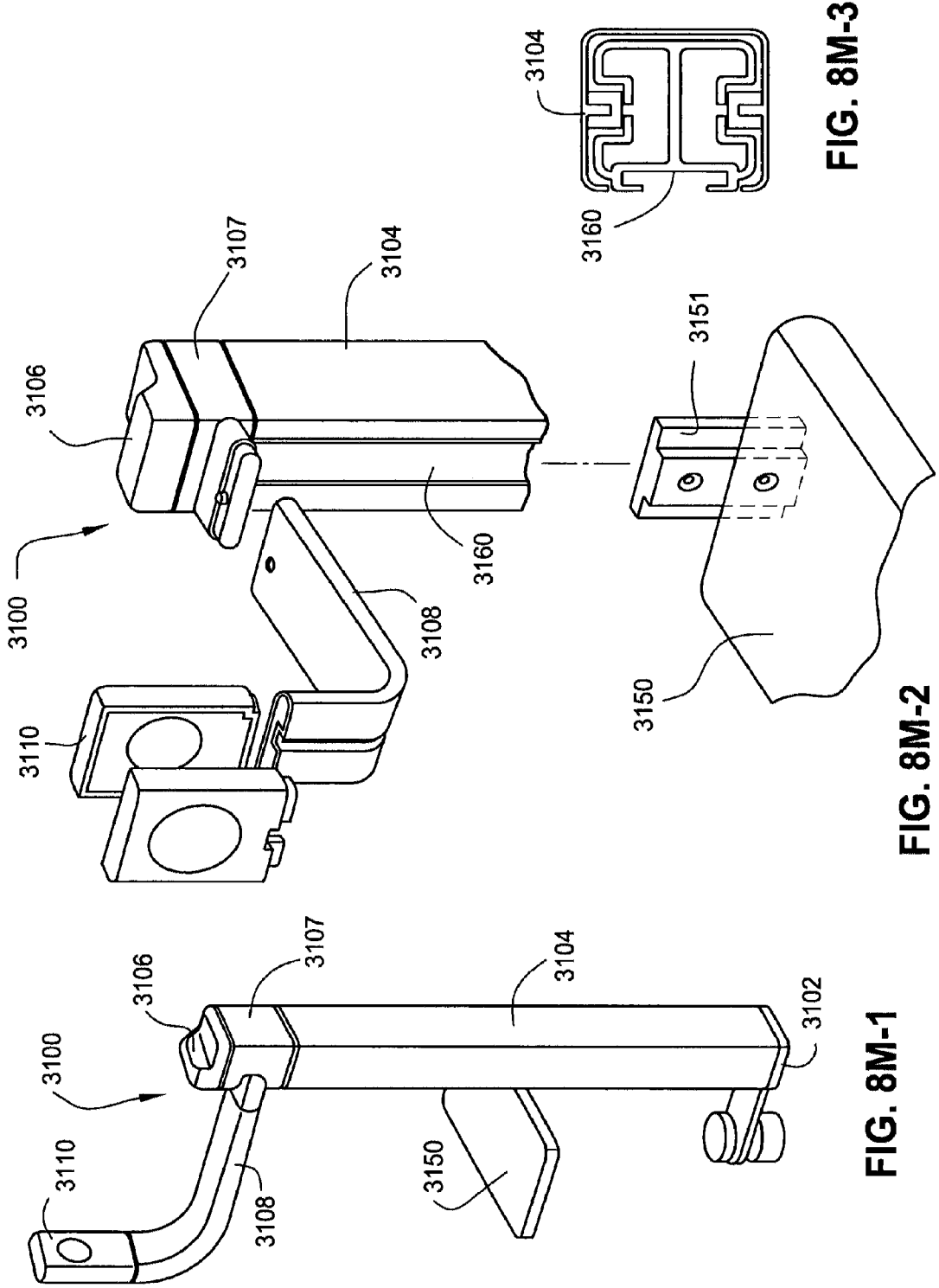

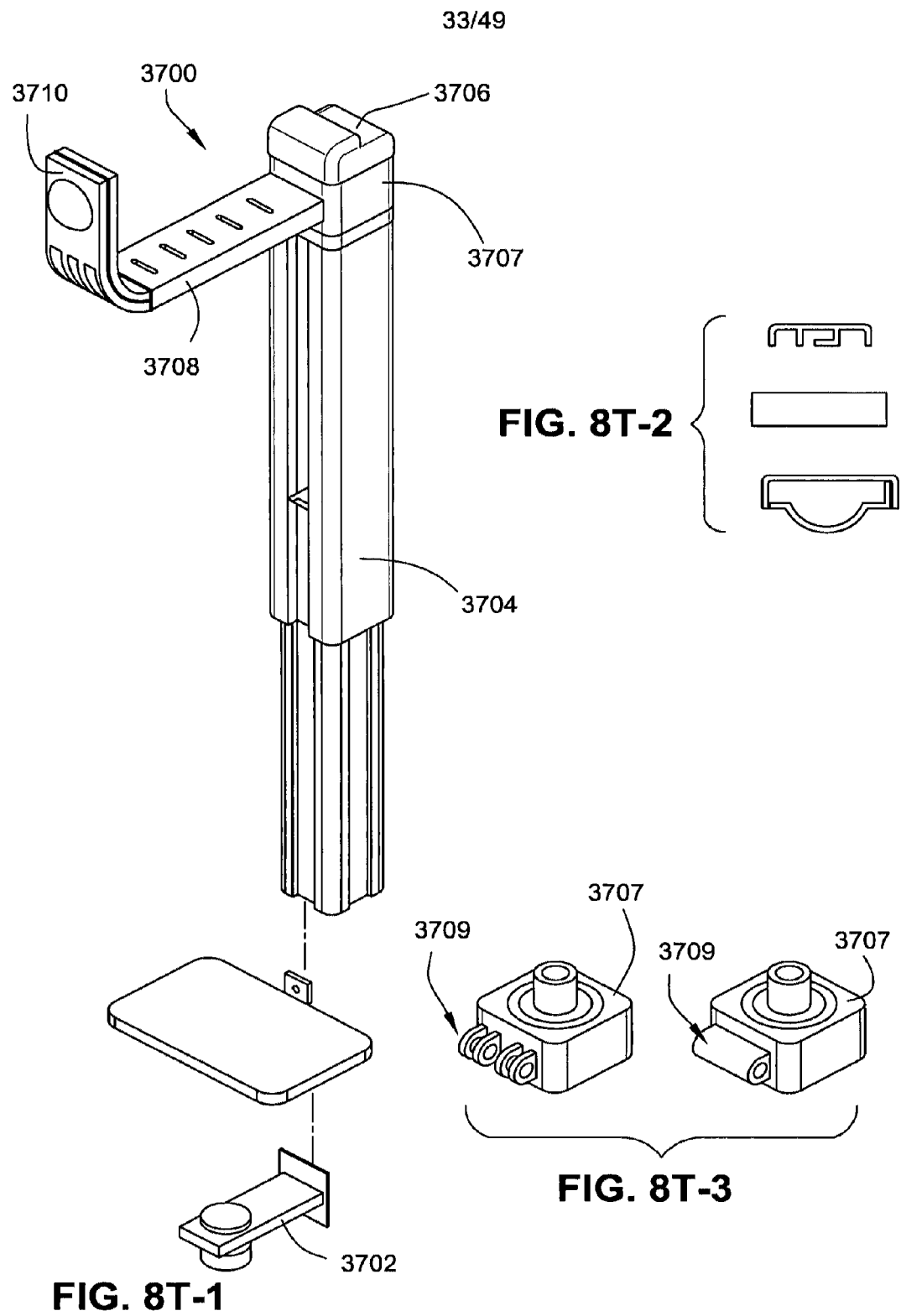

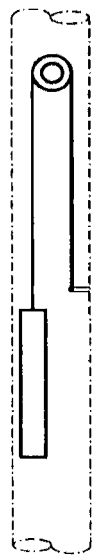
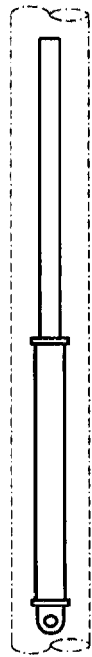
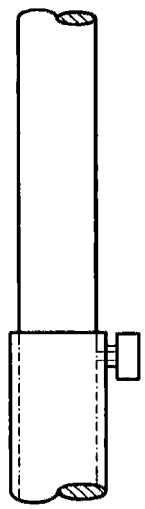
FIG. 8W-1    FIG. 8W-2    FIG. 8W-3
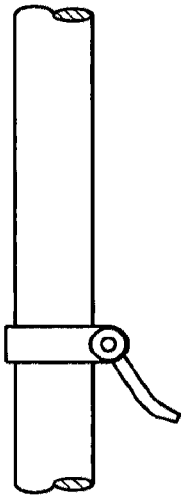
FIG. 8W-4    FIG. 8W-5

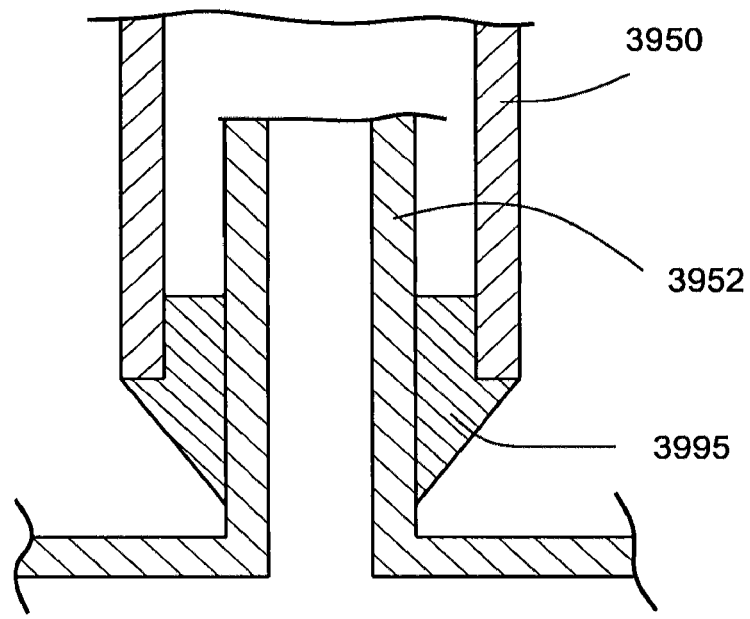
FIG. 8X
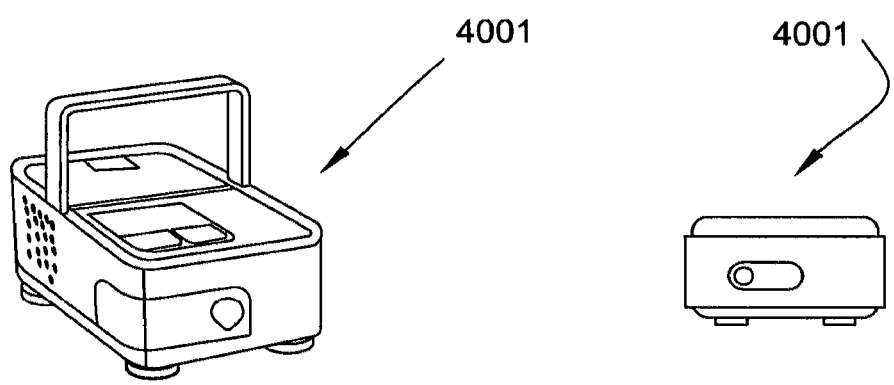
FIG. 8Y-1  FIG. 8Y-2

MASK FITTING SYSTEM AND METHOD

CROSS-REFERENCES TO APPLICATIONS

This application claims the benefit of U.S. Provisional Application Nos. 60/833,482, filed Jul. 27, 2006, 60/840,003, filed Aug. 25, 2006, and 60/842,996, filed Sep. 8, 2006, each of which is incorporated herein by reference in its entirety.

Also, the application incorporates by reference the entirety of each of U.S. application Ser. No. 10/556,461, filed on Nov. 10, 2005, PCT Application No. PCT/AU2005/000810, filed Jun. 6, 2005, U.S. Provisional Application Ser. No. 60/619,951, filed Oct. 20, 2004, and U.S. Provisional Application Ser. No. 60/576,621, filed Jun. 4, 2004.

FIELD OF THE INVENTION

This application is directed to a mask fitting system. In particular, the invention relates to a system for selection of a mask for patients suffering from a sleeping disorder, such as obstructive sleep apnea.

BACKGROUND OF THE INVENTION

There are several techniques which have been used in the past to fit mask systems to patients. In one example, a mask fitting template is used to obtain the necessary dimensions from the patient. Such mask fitting templates are available from ResMed Limited. In another example, a doctor or clinician will pick a mask system, such as ResMed's standard Ultra Mirage®, where a single mask system is believed to fit up to 80% of the population. Otherwise, the doctor or clinician selects a mask system for a patient simply by looking at the patient. Whichever technique or technique combination is used, selection of a mask system to obtain an optimal fit is limited by the knowledge of the clinician or doctor who is treating the patient.

With an ever increasing range of different masks available to fit a wide range of different people, it is increasingly difficult for clinicians or doctors to choose the most appropriate mask for the patient in the limited amount of time for fitting. The most appropriate fit, as used herein, may refer, for example, to the best human interface fit, maximum comfort, maximum seal, and/or the best type of technology to suit a patient's circumstances, needs and preferences. Therefore, patients in some cases may not be fitted with a mask system that would best fit the patient, which may result in less effective treatment and/or less patient compliance.

Therefore, it will be appreciated that a need has arisen to develop a system to allow for convenient and automated selection of a patient's mask system.

SUMMARY OF THE INVENTION

One aspect of the invention aims to ameliorate one or more of the above noted problems.

Another aspect of the invention is to match the patient with the most appropriate mask system, thereby improving the effectiveness of treatment and overall patient compliance.

Certain example embodiments provide a mask fitting system for selecting at least one mask system for a patient. Such systems may comprise a cushion of pins capable of being positioned over at least a portion of the patient's face. They may further comprise a processor operable to associate a location in a three-dimensional space with each pin in the cushion of pins; generate a contour of the patient's face or portion of the patient's face based at least in part on the location associated with each pin; and, based at least in part on the contour associated with each pin, select at least one mask system suitable for the patient. A display may be present, which may be operable to display the contour and/or the at least one mask system.

Certain example embodiments provide a method of selecting at least one mask for a patient. That method may comprise positioning a cushion of pins over at least a portion of the patient's face. A location in three-dimensional space can be associated with each pin in the cushion of pins. A contour of at least a portion of the patient's face based at least in part on the location associated with each pin also can be generated. The method may further comprise selecting at least one mask system suitable for the patient based at least in part on the contour and/or the location associated with each pin. Also, the contour and/or the at least one mask system may be displayed.

In certain example embodiments, a mask fitting system for selecting at least one mask system for a patient is provided. Such systems may comprise a sensor operable to generate a signal representing at least a portion of the patient's face comprising at least the patient's nasal area. Such systems also may comprise a processor operable to generate a contour of at least the patient's nasal area based at least in part on the signal, and further operable to determine a type and direction of nasal prongs suited to the patient based at least in part on the contour.

In certain example embodiments, a method of selecting at least one mask for a patient is provided. The method may comprise generating a signal that represents a portion of the patient's face comprising at least the patient's nasal area. Such systems also may comprise generating a contour of at least the patient's nasal area based at least in part on the signal. A type and direction of nasal prongs suited to the patient based at least in part on the contour can be generated.

In certain other example embodiments a mask fitting system for selecting at least one mask system for a patient is provided. Such systems may comprise at least one light operable to cast a shadow on at least a portion of the patient's face. A shadow steropsis sensor may be operable to generate a signal corresponding to the shadow. Such systems also may comprise a processor operable to generate a contour of at least a portion of the patient's face based at least in part on the signal.

In certain other example embodiments a method of selecting at least one mask for a patient is provided. Such methods may comprise shining at least one light on at least a portion of the patient's face. A shadow steropsis sensor may be used to generate a signal corresponding to the shadow. Then, a contour of at least a portion of the patient's face based at least in part on the signal can be generated.

Yet other example embodiments provide a mask fitting system for selecting at least one mask system for a patient. Such systems may comprise an image and/or video acquiring device operable to capture at least one image and/or video of at least a portion of the patient's face. A processor may be operable to process the at least one image and/or video to determine a physical characteristic of the patient's face based at least on the at least one image and/or video and at least one symbol, with the at least one symbol having been applied to the patient's face prior to the image and/or video acquiring device capturing the at least one image and/or video.

Yet other example embodiments provide a method of selecting at least one mask for a patient. Such methods may comprise applying at least one symbol to the patient's face. At least one image and/or video of at least a portion of the patient's face may be captured. Such methods also may comprise determining a physical characteristic of the patient's face based at least in part on the at least one image and/or video and the at least one symbol.

In certain example embodiments, a mask fitting system for selecting at least one mask system for a patient is provided. Such systems may comprise an image and/or video acquiring device operable to capture at least one image and/or video of at least a portion of the patient's face. A routine may be operable to allow at least one image of at least one mask system and the at least one image and/or video to be overlaid. Such systems also may comprise a display for showing the overlaid images and/or videos.

In certain example embodiments, a method of selecting at least one mask for a patient is provided. Such methods may comprise capturing at least one image and/or video of at least a portion of the patient's face. The at least one image and/or video may be displayed. Also, at least one image of at least one mask system may be displayed. The method may further comprise overlaying the at least one image and/or video and the at least one image of a mask system.

Certain example embodiments provide a transparency reflecting a design of a mask system, the transparency capable of being held to a patient's face to determine a goodness of fit of the mask system as indicated by the transparency.

Certain example embodiments provide a method of selecting at least one mask for a patient. Such methods may comprise providing at least one transparency reflecting a design of a mask system. The transparency may be held up to the patient's face. Such methods may further comprise selecting the at least one mask system based on a goodness of fit of the mask system as indicated by the transparency.

It will be appreciated that the above-described example embodiments also may be used as systems and/or methods for treating patients with sleeping disorders. In such example embodiments, one or more mask systems may be provided to the patients for use. It also will be appreciated that certain example embodiments will select at least two mask systems for a patient. In such example embodiments, a schedule for rotating among and/or switching between mask systems may be generated and/or provided to the patient.

Certain example embodiments provide a method of prescribing mask equipment to a patient for a sleeping disorder. The method may comprise compiling patient-specific data relevant to treatment of the sleeping disorder. At least two mask systems suitable for alternating use by the patient may be selected, based at least in part on the patient specific data.

Although the mask fitting system is described in relation to mask systems for patients who suffer from obstructive sleep apnea, the mask fitting system is not limited to such applications and may be provided to select patient interfaces and/or their accessories, such as headgear, for patients who suffer from other disorders. The mask fitting system may also be used as simply a method to record clinical details. Moreover, the mask fitting system can be used to select a mask/components for users who do not suffer from disorders, e.g., occupational health and safety masks.

Another aspect of the invention relates to a head support and camera mount assembly including a base, an upright provided to the base, and an arm extending outwardly from the upright. The upright includes a chin support adapted to support a patient's chin in use. The arm has a distal end structured to support an imaging device configured to capture at least one image of the patient's face when the patient's chin is resting on the chin support in use.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 7B-1 to 7B-3 illustrate exemplary methods for obtaining mask fit dimensions according to embodiments of the present invention;

FIGS. 8A-1 to 8A-3 illustrate a head support and camera mount according to an embodiment of the present invention;

FIGS. 8B-1 to 8Y-2 illustrate various features of a head support and camera mount according to alternative embodiments of the present invention;

DETAILED DESCRIPTION OF ILLUSTRATED EMBODIMENTS

Figure 1:
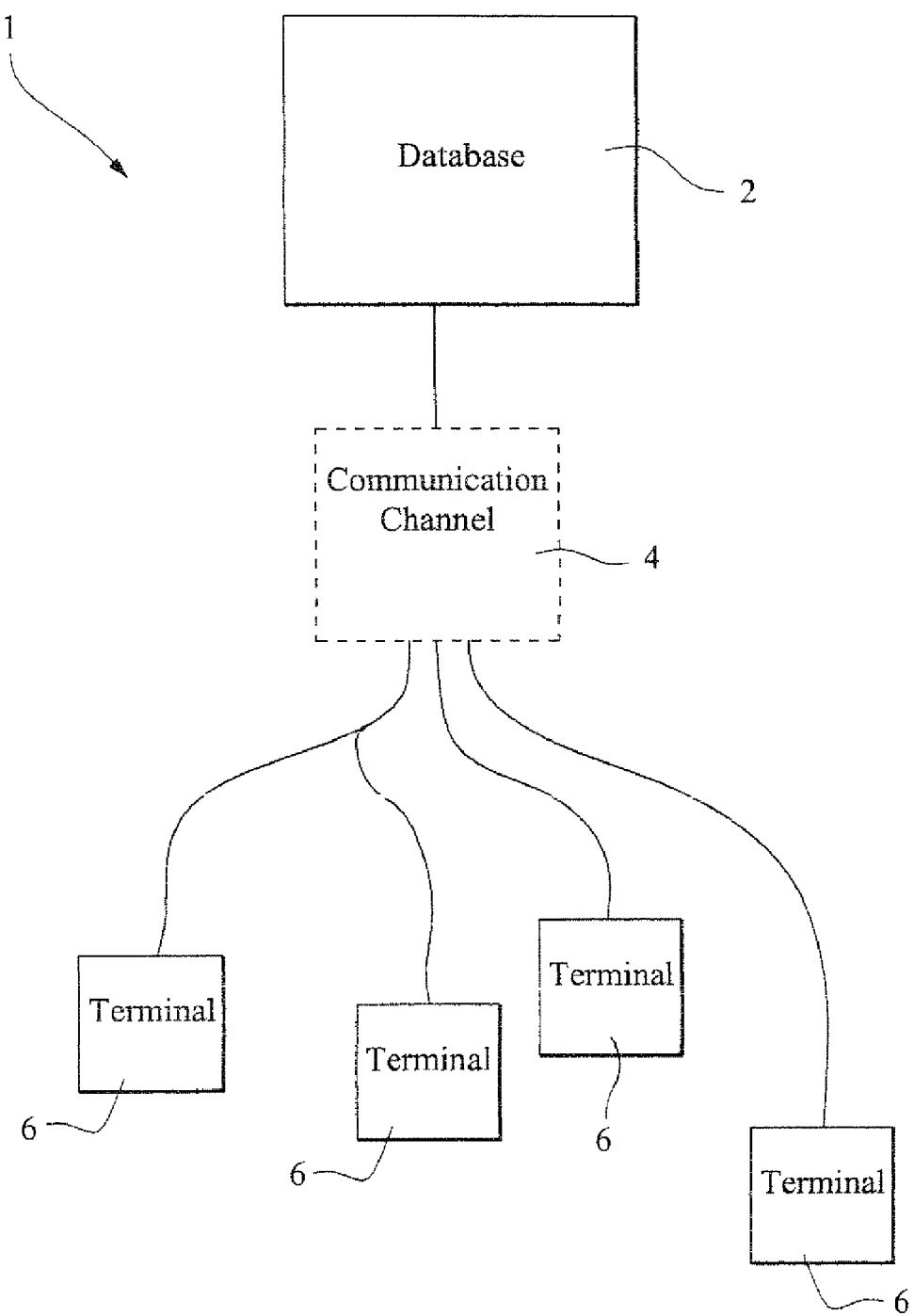
FIG. 1 is a schematic block diagram illustrating a mask fitting system according to a preferred embodiment of the invention.

A mask fitting system 1 according to an embodiment of the present invention is illustrated schematically in FIG. 1. Mask fitting system 1 includes a mask fitting database 2, one or more terminals 6, and a communication channel 4 between database 2 and terminals 6.

Mask fitting database 2 is provided to store data on a plurality of commercially available mask systems. The database 2 may be provided directly by a manufacturer of mask systems, or may be provided by a third party with the relevant information being obtained from the manufacturer.

Communication channel 4 allows communication between the database 2 and terminals 6, which may be remotely located from database 2. Communication channel 4 may be embodied in any suitable manner, for instance, wireless or land telecom line. Communication channel 4 may encompass direct hosting of the database, e.g., database, channel and a terminal may be included in a single PC system.

Channel 4 can be any known or later developed device or system for connecting each terminal 6 to the database 2, including a direct cable connection, a connection over a wide area network or a local area network, a connection over an intranet, a connection over the Internet, or a connection over any distributed processing network or system. In general, the channel 4 can be any known or later developed connection system or structure useful to connect the terminal to the database.

Figure 2:
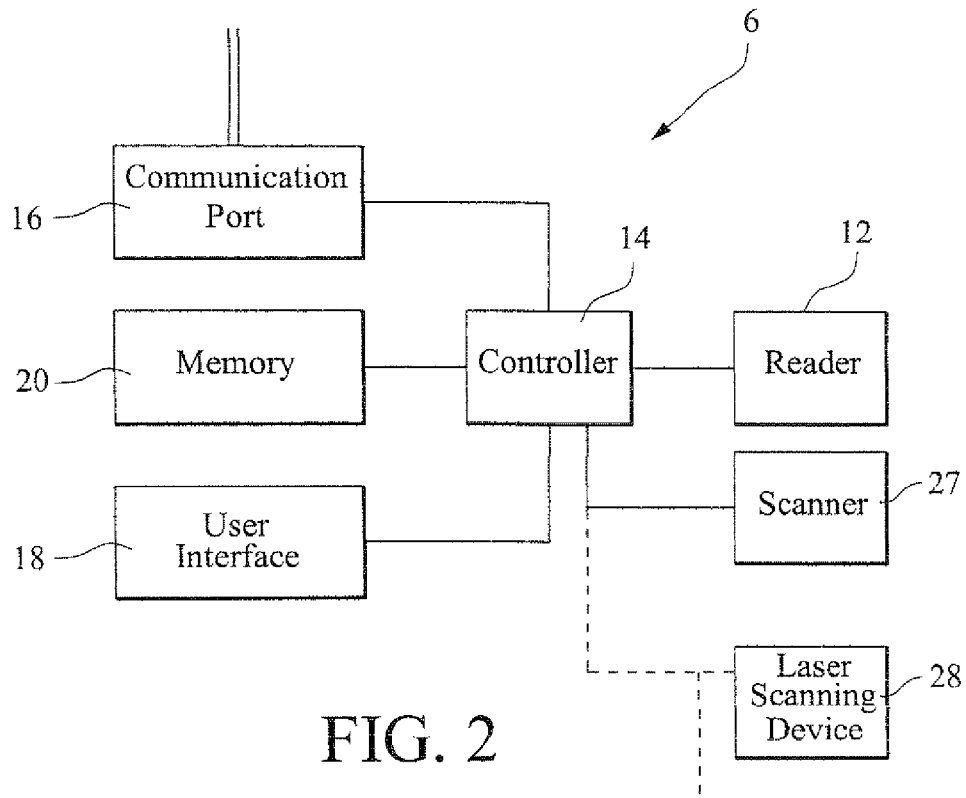
FIG. 2 is a schematic block diagram illustrating a terminal according to an embodiment of the present invention.

Terminals 6 are provided at locations where mask systems are recommended to patients, either by way of sale of the mask systems or merely dispensing them. As illustrated in FIG. 2, each terminal 6 is provided with a reader 12 by which information (patient data) from the patient may be read, received, scanned or otherwise input. A controller 14 may then communicate some or all of this data to a database 2 by means of a communication port 16.

A user interface 18, including, e.g., a monitor or display, may be provided to indicate to the user (patient, interface fitter, clinician and/or physician) the most appropriate mask system or systems for the patient. Also, terminal 6 may have access to more general information about each mask system, and/or accessories that could be used with the recommended mask system(s). Such information can be displayed on the interface 18. Further, a memory 20 may be provided to store data relating to the patient and/or database 2, or to merely assist in the processing of the controller 14.

In one example, reader 12 could include a camera (e.g., a digital or film camera, webcam, scanner, etc.) that is provided to take images of the patient from various angles, for example, profile and/or frontal views, for measurement of various dimensions of the patient's head. This is described in more detail below in relation to FIGS. 4-8. In addition or in the alternative, the terminal may include a facial scanner 27 (e.g. a facial scanner is commercially available from Cyberware). Scanner 27 may use 3D modeling techniques to scan the entire face, head, or other expected interfacing regions, or only selected portions thereof.

Other readers may include a handheld three-dimensional laser scanning device 28 (e.g. a commercially available device such as the Polhemus Cobra FastScan system). This system comprises a laser, reference transmitter, data acquisition unit and software. The data from the laser and the reference transmitter is fed to a Data Acquisition Unit (DAQ). The DAQ plots the data into a 3D plane. This information can be translated using the provided software to different 3D file formats such as wrl, stl and iges.

The Polhemus Cobra FastScan scanner has an accuracy 0.5 mm and should be held at least 10 cm away from the object. The Cobra FastScan can be operated in two different modes. In the first mode it collects data as a laser sweep and 3D models are created using the data, the file format can be output in many different engineering formats the majority being either 3D mesh or point cloud. In the second mode data is collected as 3D points in an x, y and z coordinate system. These points are recorded to a Comma Separated Values (CSV) file (or any file type, preferably with a known layout) which is a simple file that can be fed into Excel or by any programmable text reader.

When scanning a person, care must be taken to ensure that the eyes are closed. Scans of people with dark skin can be difficult, in which case the laser sensitivity has to be adjusted or a white powder can be applied to the face. During scanning, the scanned person must not change his or her facial expressions, however he or she can move their head around as the reference transmitter monitors position change (it is directly connected to the DAQ).

Several non-limiting examples of output options include:
3D scan of the face via image file (wrl, stl, iges) or a test file giving reference points (csv); and,
Points taken at discrete positions (text file, csv).

Alternatively a stylus can be attached that is directly attached to the DAQ and can be run along the face to measure distances (e.g., nose bridge).

One or more of the following advantages of this system exist:
The profile can be stored for further use;
Quick and efficient (e.g. 5 minutes per scan and 10 minutes to process the scan, note: processing can be left until night);
Improved accuracy with respect to hand measurement;
Image can be saved straight to an stl format (or other image file format), from which an SLA (solid) can be developed straight away;
Use of a design package such as ProE means that objects (e.g., masks) can be added around the scanned facial profile; and,
Measurements can be taken whilst patients are lying down.

An alternative to the Polhemus FastScan is a 3D laser scanner, which can be tripod mounted to scan 3D objects. Such laser scanners can capture the color of the object scanned with the 3D data. High accuracy lenses can be used, and preferred embodiments may have an accuracy of between 50 microns to 0.5 mm. In the situation where a completed 3D head of a patient is required, the laser scanner may scan the object from a number of different angles and the scans are then stitched together with a suitable scanning software package.

Of course, other scanners, readers or input devices are also contemplated, and the embodiments are not limited to the examples provided.

For example, the scanner system may take the form of a 3D scanner that is movably mounted or relative to the patient. The 3D scanner can rotate about the patient to scan along a predetermined circular path, e.g., 0-360° or any amount in the range of 0-360°. Dental X-rays are sometimes taken with such a system. Moreover, the scanner would be stationary while the patient's support (e.g., a chair or platform) rotates.

In a preferred embodiment, the scanner preferably covers the entire head, including the individual features, e.g., ears, nostrils, etc. As further masks are developed and require new data points to be utilized, further scans would not be required. For example, in considering a new headgear sized to avoid behind the ears, the scans would already contain this data. Therefore, upgrades of masks would not require re-scanning. Moreover, using the system described below, patients who wear masks can be automatically informed, either directly or through their clinician, of new mask systems/components that are more appropriate and/or provide a better fit for the patient.

Figure 3:
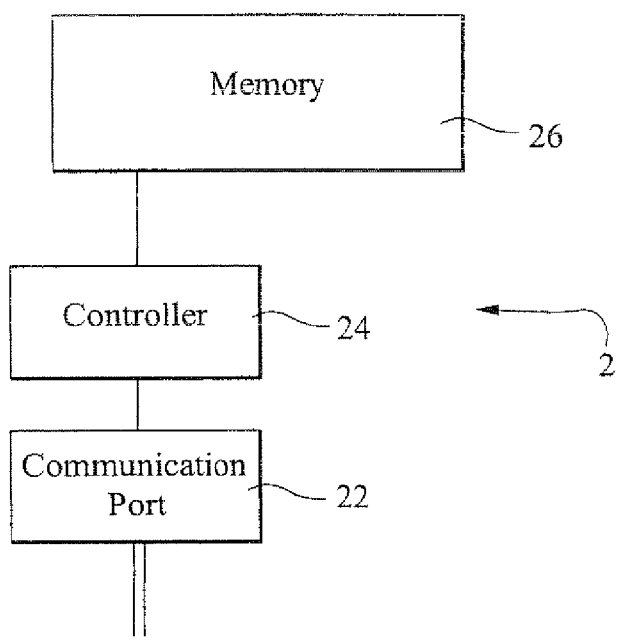
FIG. 3 is a schematic block diagram illustrating a mask system database according to an embodiment of the present invention.

FIG. 3 shows that the mask system database 2 includes a communication port 22 to allow communication with terminal 6 (FIG. 2), via channel 4. Communication port 22 may also allow communication with manufacturers for receiving data regarding mask systems. In addition, communication port 22 may receive information from other third parties, such as governmental agencies which may provide product reviews of the mask systems, possible accessories, product recalls, etc.

Mask system database 2 includes a controller 24 that interfaces with a memory 26. Memory 26 includes information (mask system data) regarding a plurality of mask systems that are commercially available. Such information includes, for example, and without limitation, data regarding the dimensions and/or weight of the mask system. Such data may also include the intended sex, age, age range, or size of patients with whom the mask system is intended for use.

In a preferred embodiment, the mask system data is based on mask system grading criteria such that mask systems with particular disadvantages or advantages are scored, rated or graded accordingly. For example, if a particular mask system is not conducive for a patient who likes to read using reading glasses when the mask system is being used, e.g., because the mask system includes an upwardly extending forehead support that may obstruct the patient's field of view and/or interfere with reading glasses, then that particular mask system would receive a lower weighted score for that particular mask system grading criteria, e.g., this mask system would receive a grade of "3" (on a scale of 1-10, 10 being the best possible grade). On the other hand, if a mask system is particularly useful for patients who have a beard and/or mustache, then the weighted score for that particular criteria will be relatively higher, e.g., a "9," when compared to other mask systems which are not particularly conducive for patients who have facial hair.

In an embodiment, a relative measure of the expected goodness of choice or fit may be presented to the mask fitter. This may be a star ranking system or similar. For example, a mask size that appears to fit very well in all areas may be given 5 stars. In another example, all mask sizes may be ranked and the top two mask sizes may both receive a 3 star ranking. This may indicate to the mask fitter that it is a bit of a toss-up between the first two sizes. Still another example may have the top ranked mask receive only a one star ranking. This may indicate to the mask fitter that the most likely choice is not expected to be a good fit. This arrangement may add more value to the mask recommendations than is currently available. The same principle may be applied to mask type so that a mask type that is expected to suit the patient very well based upon lifestyle selections and clinical history may receive a high ranking. This arrangement adds more value to the mask recommendations than is currently available. Of course, percentages or a number of noses or other mechanisms may be used in place of stars.

Other possible criteria includes mask size maximum fit dimensions, mouth width, nasal bridge width or depth, total nose depth, nose length, nostril spanning/sparring and angle, ear position, circumference or width of head, etc. Additional mask system grading criteria is described below.

In general, several medically acceptable mask system criteria can be established for universally grading any given mask system in a consistent manner. Such criteria can be used to establish database 2, shown in FIG. 2. In one embodiment, each mask/accessory can be provided with a tagging device, e.g., a bar code, uniform product code, RFID, etc., with data relating to product description, code, batch, purchase, etc. The information from the tagging device may be read and input into the database.

In addition to or in the alternative of using grading by best dimensions, etc., grading by "elimination" may also be used. For example, the questionnaire (an example of which is described below with reference to FIG. 5) reduces the number of mask options to select from by eliminating non-appropriate masks. Therefore, improved accuracy and speed of selection can be achieved by selecting from a smaller pool of potential masks.

In operation, the mask fitting system 1 is configured to produce a best-fit mask fitting result which is indicative of one or more commercially available mask systems that would be most appropriate for the patient. The result is generated in accordance with a comparison of patient data (received at terminal 6) with mask system data (stored in mask system database 2). The comparison may be performed by the controller of the terminal 6, the controller of database 2, or a combination thereof.

FIGS. 4, 5, 6, 7A, 7B and 8 illustrate sequential screen shots of a mask fitting system according to an embodiment of the present invention. In general, the process includes the entry of patient details, filling out of a questionnaire, imaging, dimensioning and then recommending a mask.

Figure 4:
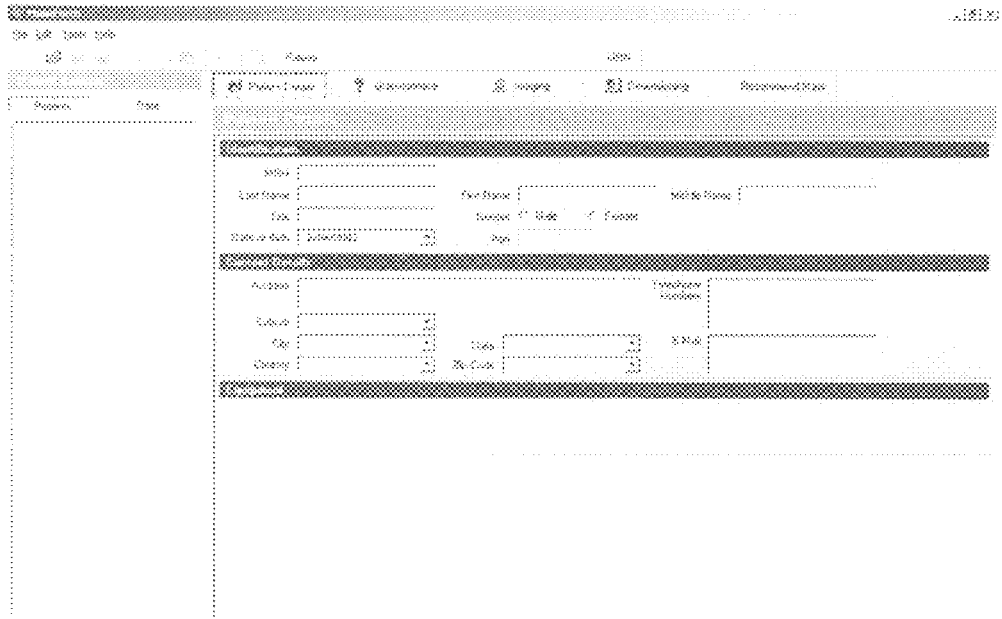
FIGS. 4, 5, 6, 7A, 7B and 8 illustrate sequential exemplary screen shots of a mask fitting program in use, according to an embodiment of the present invention.

FIG. 4 is a screen shot displaying entry blocks for patient details, such as name, age, data of birth, etc.

Figure 5:
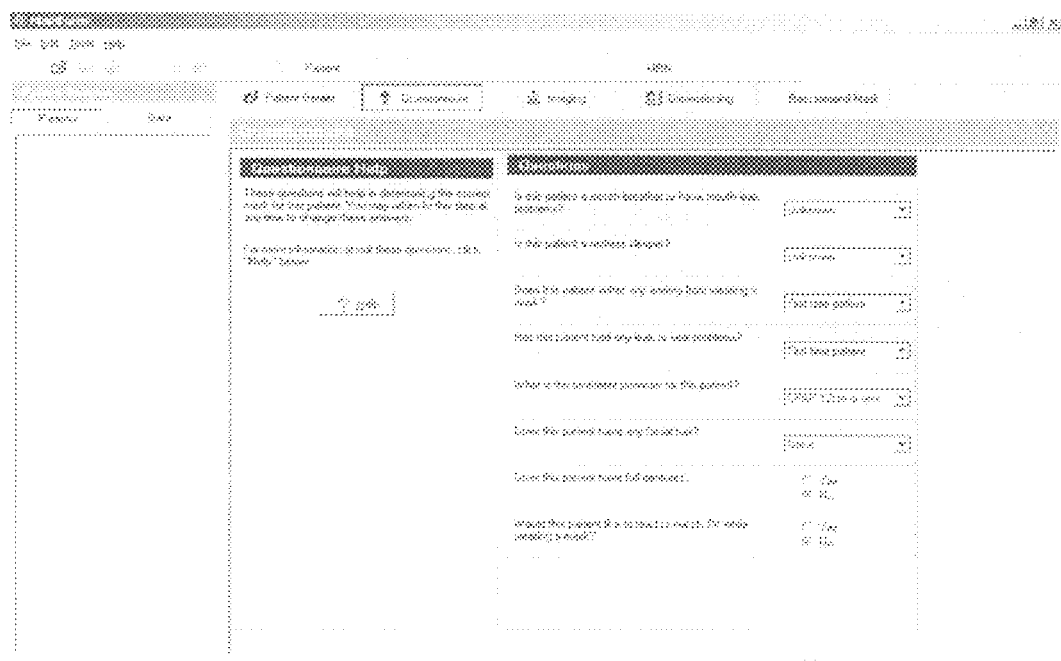

FIG. 5 is a questionnaire which includes several questions which are answered by the patient or clinician. Generally speaking, the questionnaire is used to accumulate patient data unique to the patient. Patient data may include, but is not limited to, physical characteristics, prior history of mask use, the patient's sleeping characteristics and/or the patient's relevant facial and/or head dimensions. Physical characteristics may include the patient's age, whether the patient wears glasses, whether the patient has facial hair, whether the patient wears dentures, and/or whether the patient is male or female.

The prior history of mask use may include the type of breathing the patient normally experiences, e.g., mouth breathing or nose breathing. Other criteria may include whether the patient has in the past experienced leak problems or anxiety when wearing the mask. Additional criteria may include information as to whether the patient likes to watch TV or read while wearing the mask, prior to sleep.

Sleep characteristics may include information about the typical sleep patterns of the patient, e.g., whether the patient is a restless sleeper, which may affect stability of the mask; stability may be yet another criteria built into the database.

There may also be questions designed to gauge the importance of the patient's facial image in the bedroom relative to therapeutic values. For example, a mask may provide a low visual impact but may be less likely to achieve a good seal. Some patients may prefer to just choose a mask most likely to be best for therapy but others will weigh visual impact aspects more highly.

Other factors that may affect mask selection include skin texture, skin floppiness, degree of skin wrinkling, and skin oiliness, which may also include questions answered by the clinician even if not asked of the patient.

A sample questionnaire is provided below and may include the following questions:

Mask Grading Criteria
1. Whether the patient is a new patient.
 a. Yes
 b. No
2. Degree of mouth—nose breathing
 a. Unknown/First time patient
 b. Nose breather
 c. Mostly nose
 d. Moderate mouth
 e. Mostly mouth
 f. Mouth breather
3. Degree of restless during sleep
 a. Not restless
 b. Light restlessness
 c. Some restlessness
 d. Heavy restlessness
 e. Extreme sensitivity
4. Degree of anxiety from wearing a mask
 a. Unknown/First time patient
 b. None
 c. Slight distraction
 d. Moderate distraction e. High discomfort
f. Claustrophobia
5. Does the patient have a moustache?
a. Yes
b. No
6. Does the patient have a beard?
a. Yes
b. No
7. Does the patient have any mask leak or seal problems?
a. Unknown/First time patient
b. No leaks
c. Light leakage
d. Moderate leak
e. Heavy leak
f. Extreme leak
8. What treatment pressure does the patient require?
a. CPAP 12 or less
b. CPAP greater than 12
c. Bilevel
9. Does the patient have full dentures?
a. Yes
b. No
10. Does the patient want to read or watch TV with the mask on?
a. Yes
b. No The mask grading system/algorithm is adaptable, so that new grading criteria or changes to the existing criteria can be implemented simply by updating the database, without the need to change the rest of the system. The user questions may form a part of the overall fitting system algorithm, as shown, e.g., in FIG. 16.

1. Mask Grading System Example

In the example below, the following answers to the grading selection criteria, produce the mask system grading shown below for currently available mask systems. In this example, all of the mask examples are ResMed's although other masks could be included.

| 1 | First time patient? | No |
| 2 | Mouth leak or mouth breather? | All nose |
| 3 | Restless sleeper? (Instability due to movement) | Extreme sensitivity |
| 4 | Anxiety from wearing masks? | Claustrophobia |
| 5 | Facial Hair - Moustache? | Yes |
| 6 | Facial Hair - Beard? (Full Beard) | Yes |
| 7 | Leaks or seal problems? (For refits) | Extreme Leak |
| 8 | Treatment pressure? | CPAP 12 or less |
| 9 | Full dentures? | No |
| 10 | Read/Watch TV with mask on? | No |

| Mask System | | | | | |
| --- | --- | --- | --- | --- | --- |
| | FFM | Vista | Activa | Ultra | Swift |
| Score | 30 | 125 | 175 | 130 | 165 |

2. Mask Grading System—Mask Dimensions

To determine the best possible fit among the available mask sizes currently stored in the database, the measured patient dimensions are compared with the relevant dimensions and/or characteristics of the stored mask sizes.

A preferred embodiment of the invention grades mask sizes by comparing the measured patient facial dimensions with the nominal "best fit" dimensions stored for each mask size in the database. However, other methods, such as those using statistical techniques can also be used.

For example, relevant dimensions of the mask system can be scanned, much in the way of a patient's dimensions may be scanned. In particular, the face contacting portion of a plurality of mask interfaces may be scanned, so as to capture the various topographical features of the mask, e.g., depth, width, contour, etc. This information can be stored in a database or registry. Further, the patient's facial features (which can be scanned as well) can be compared against the scanned patient interfaces and a best fit scenario may be obtained using, e.g., statistical analyses methods. Moreover, the results of the comparison can simply be used as one metric or criteria of fit, which can be weighted relative to other metrics and/or criteria (e.g., the patient's questionnaire, etc.).

The patient dimensions include, but are not limited to one or more of the following:
1. Nasal bridge width
2. Nasal root depth
3. Mid-nasal bridge width
4. Mid-nasal bridge height
5. Nasal width
6. Nose tip protrusion
7. Mouth width
8. Facial height
9. Nasal height
10. Nares diameter (in different dimensions)

Figure 8:
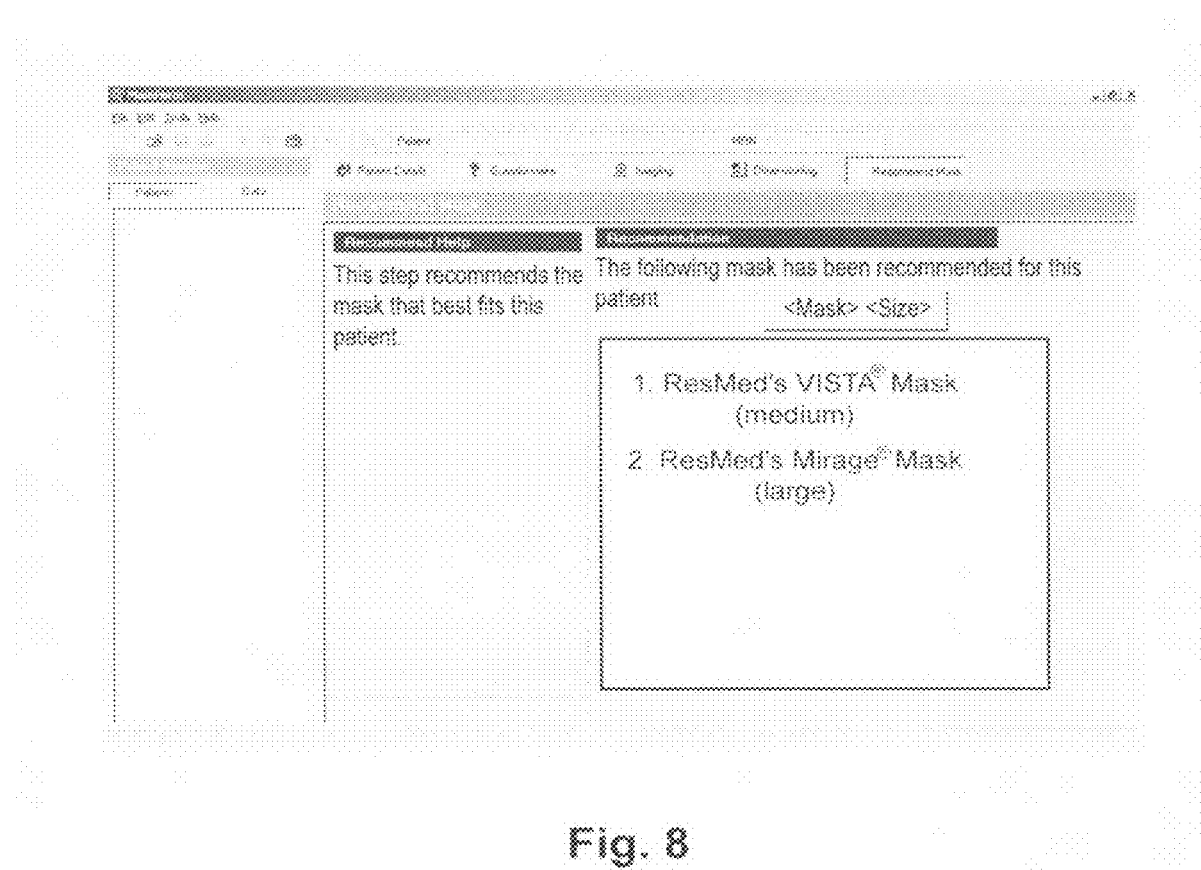
Figures 1, 8A:
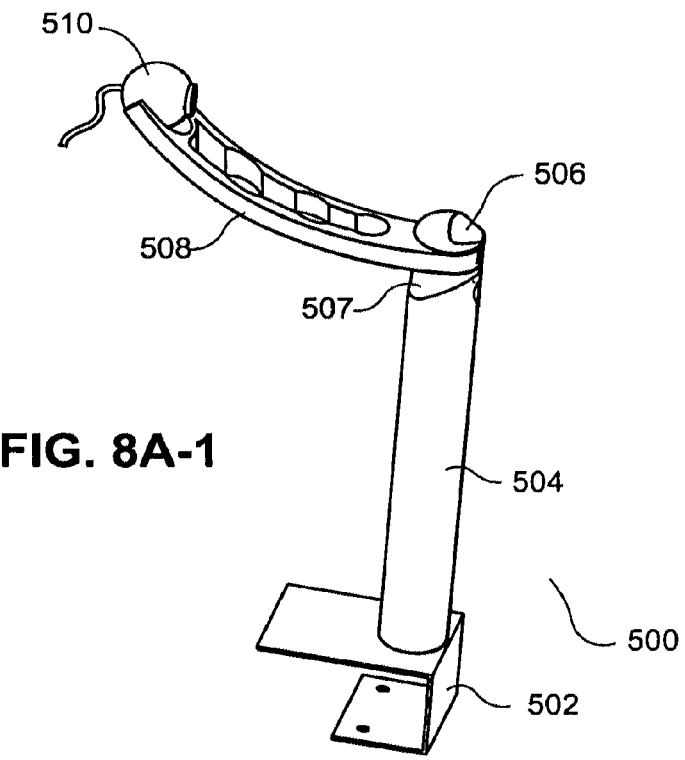
Figures 2, 8A:
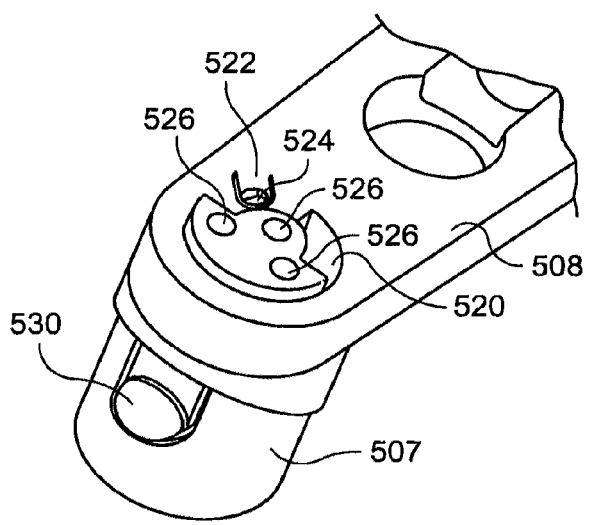
Figures 3, 8A:
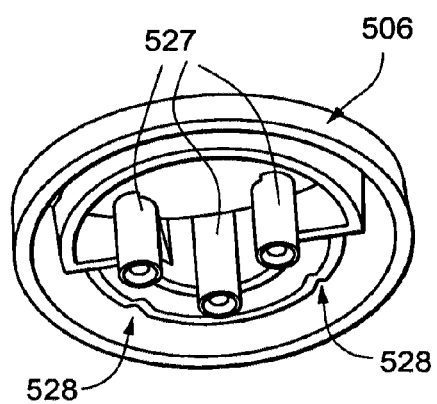
Figures 2, 8B:
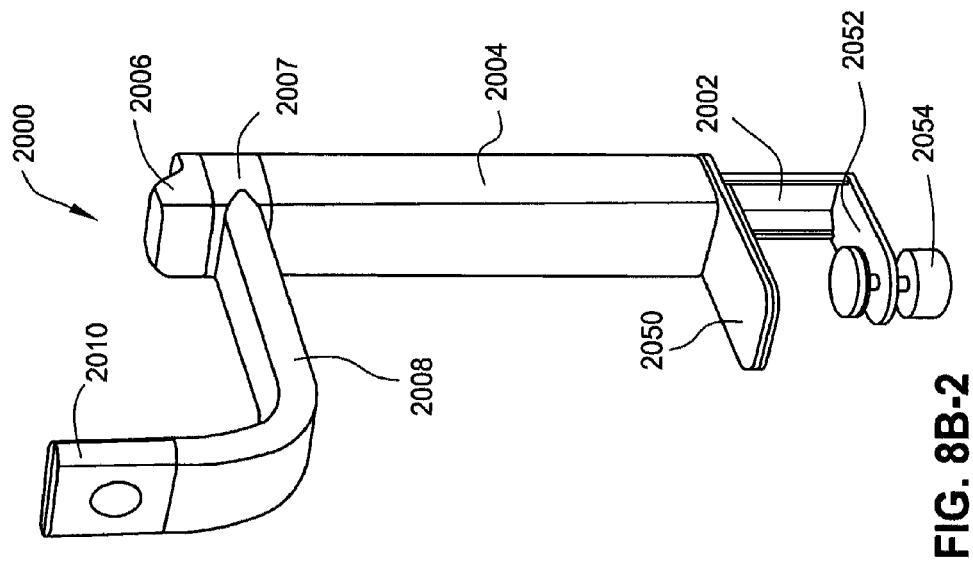
Figures 1, 8B:
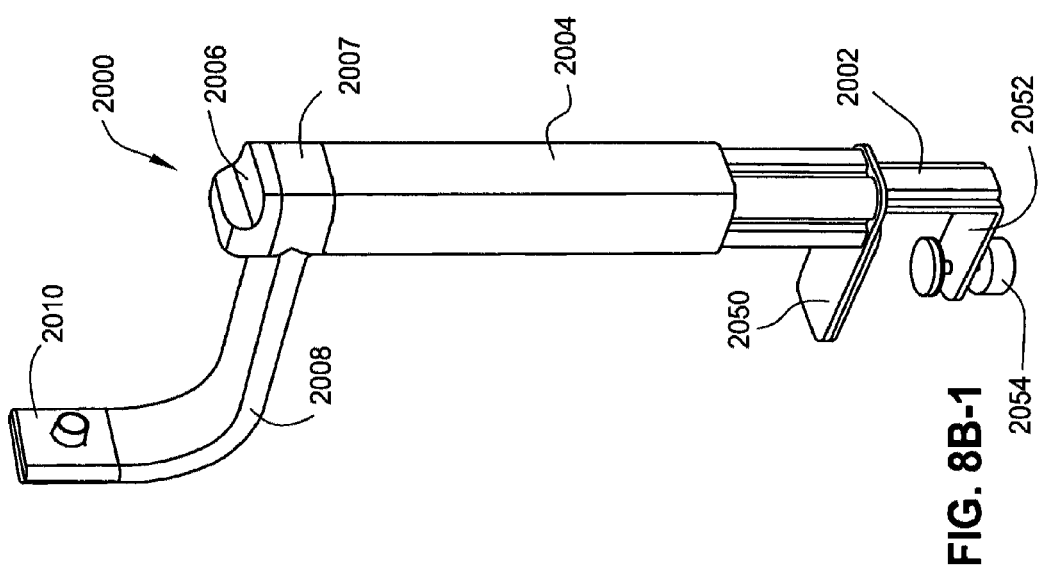
Figures 4, 8B:
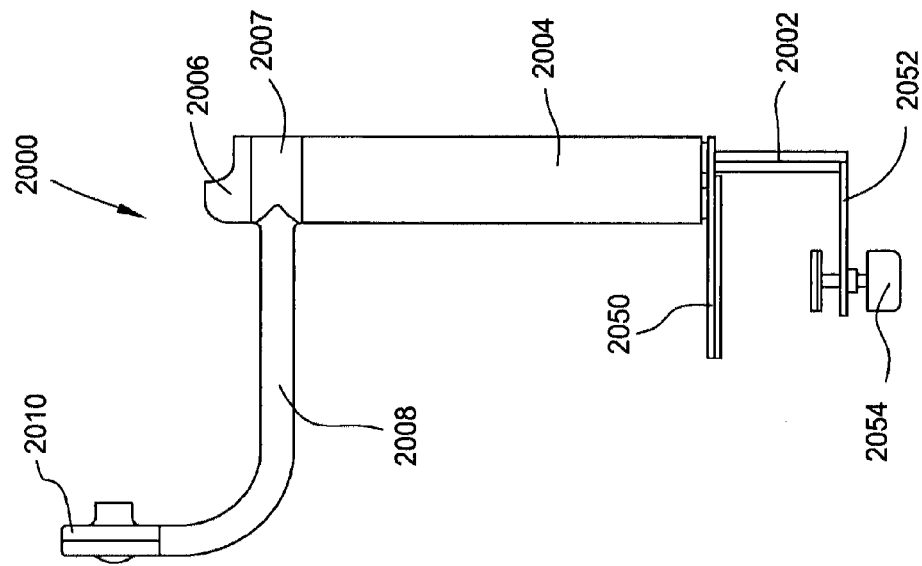
Figures 3, 8B:
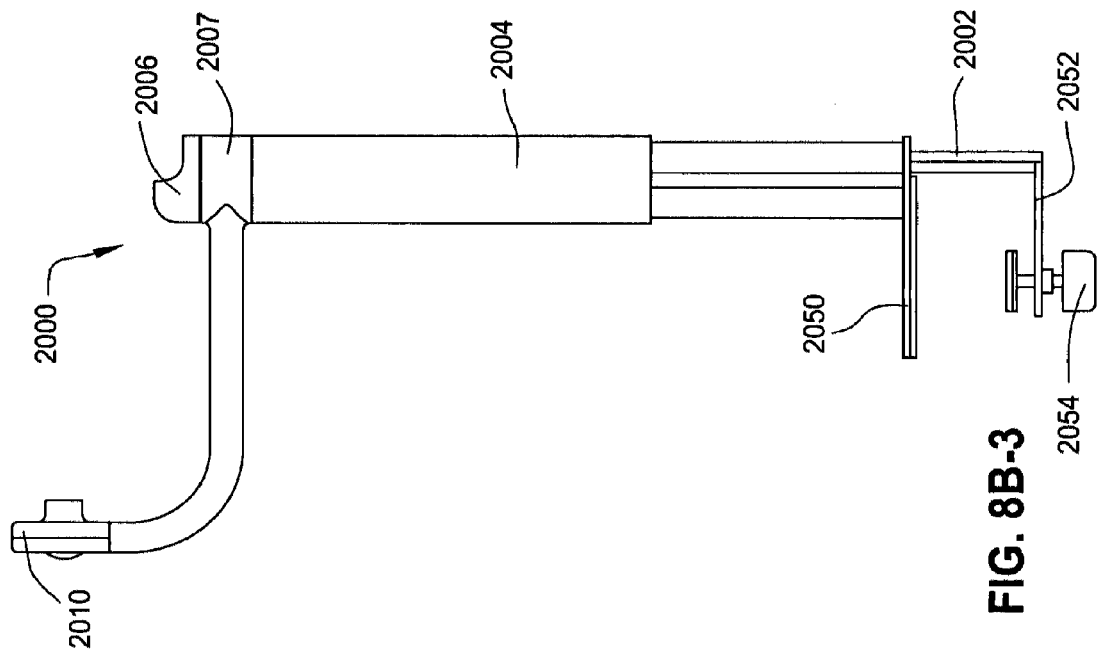
Figures 6, 8B:
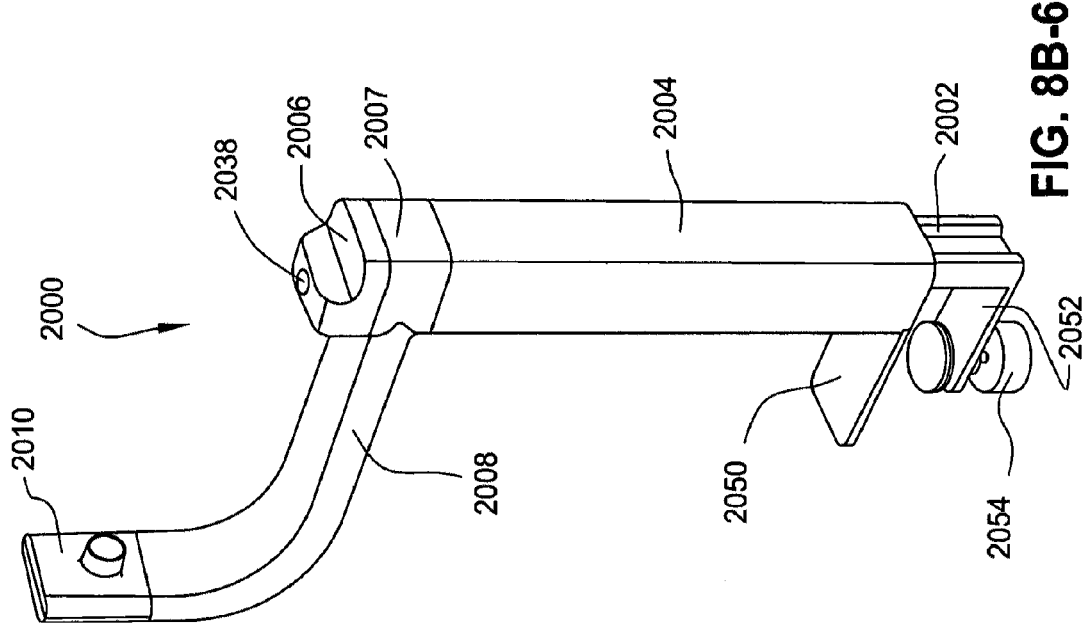
Figures 5, 8B:
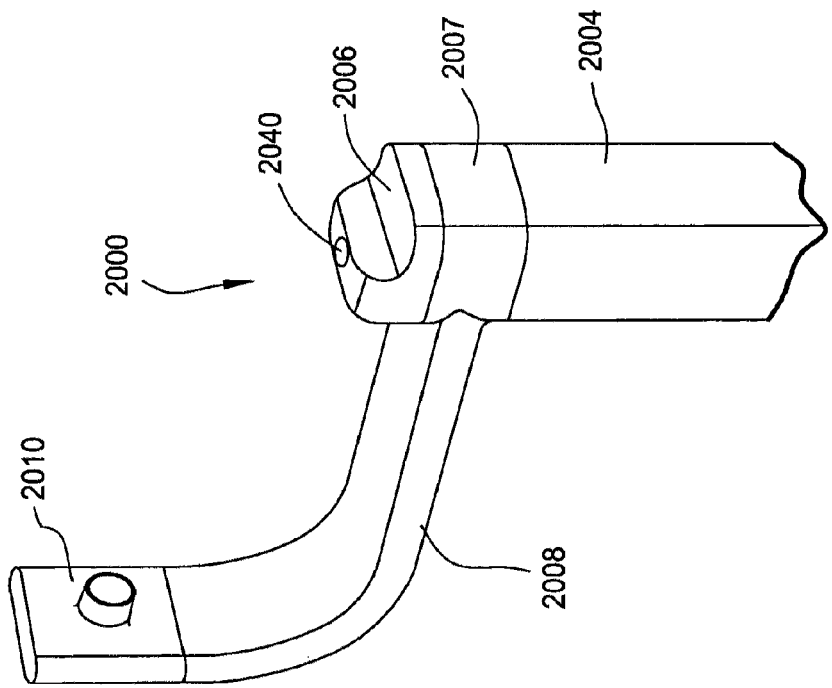
Figures 8, 8B:
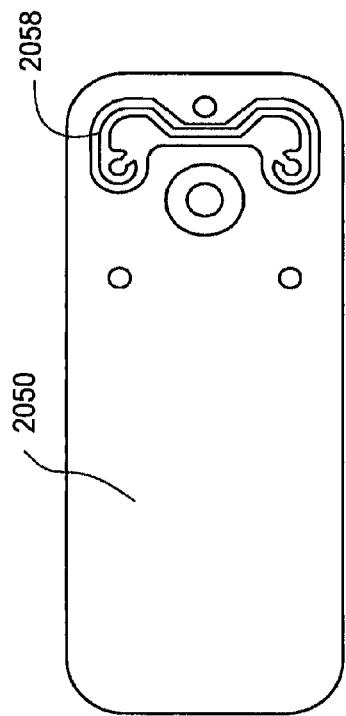
Figures 8, 8B, 9:
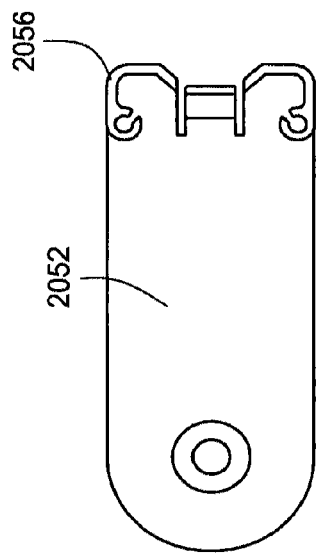

Dimensions which are necessary to fit a mask system to a patient vary, depending on the type of mask system involved. For example, a nose mask may require different information than is required for a full face mask or mask systems using cannula, nozzles, puffs, etc. FIG. 17, which is more fully described below, illustrates a sample mask fitting algorithm.

In one embodiment, the dimensions of the patient's head can be simply measured with a template or ruler and input into the terminal 6. However, FIGS. 6, 7A and 7B show a more preferred embodiment, in which one or more images of the patient are obtained (by capturing the image), and then dimensions of the patient's head are obtained (in response to user input).

Figure 6:
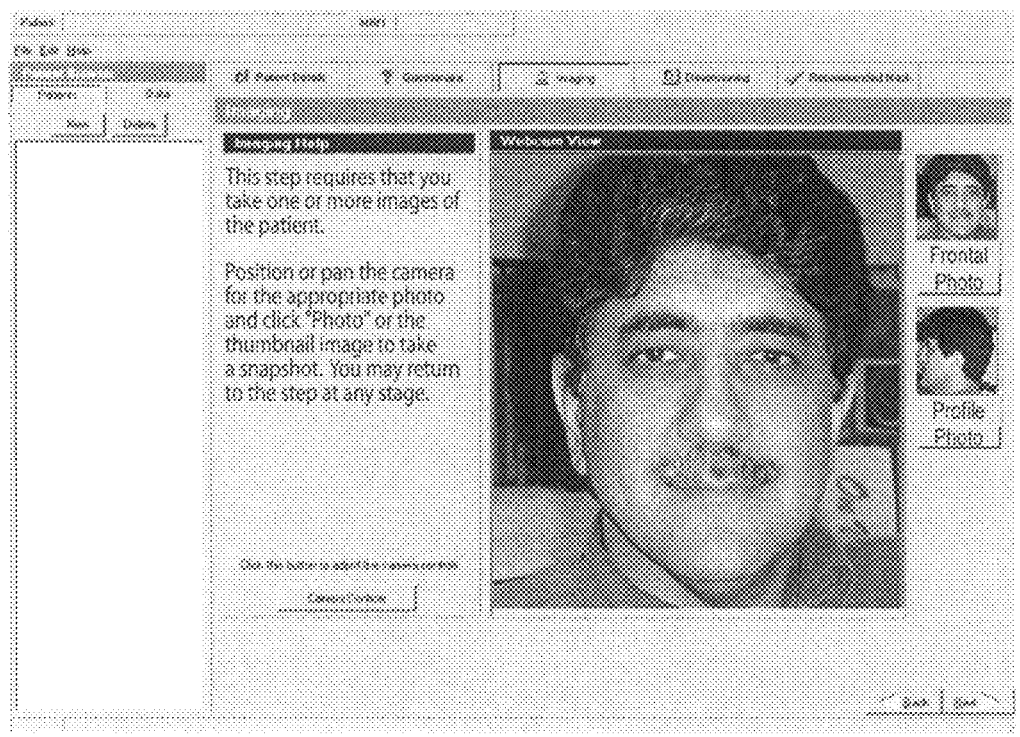
Figure 7A:
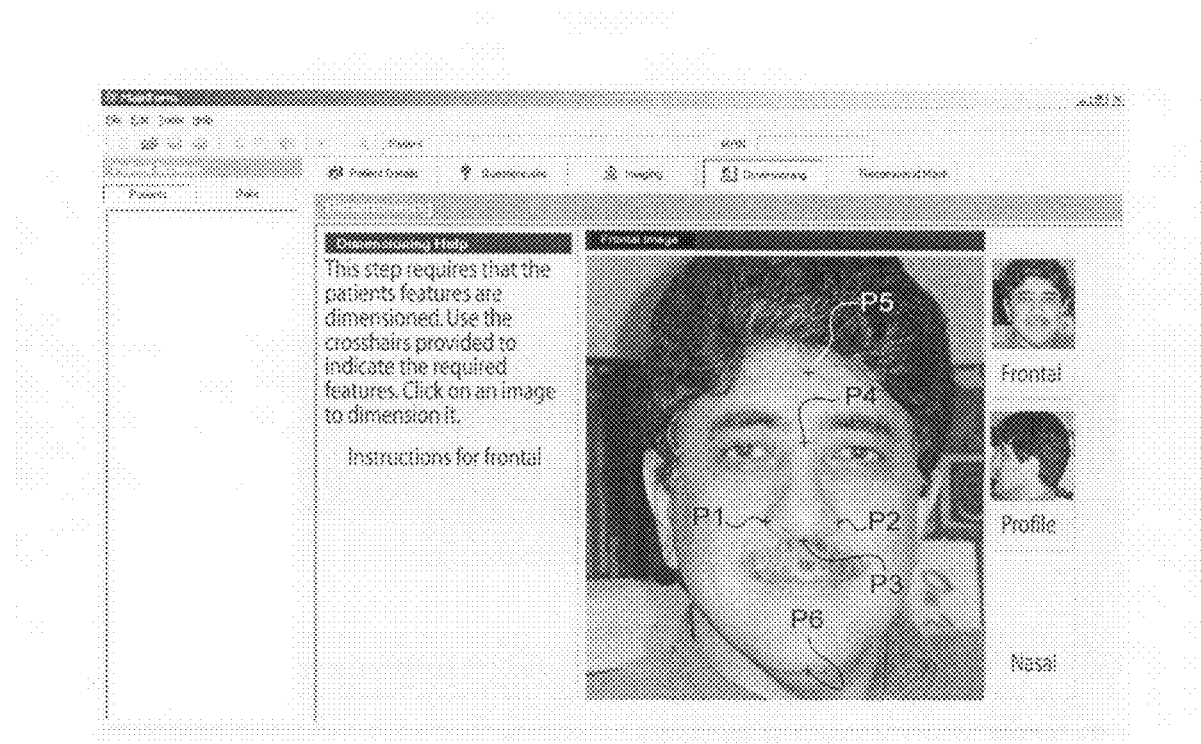
Figure 7B:
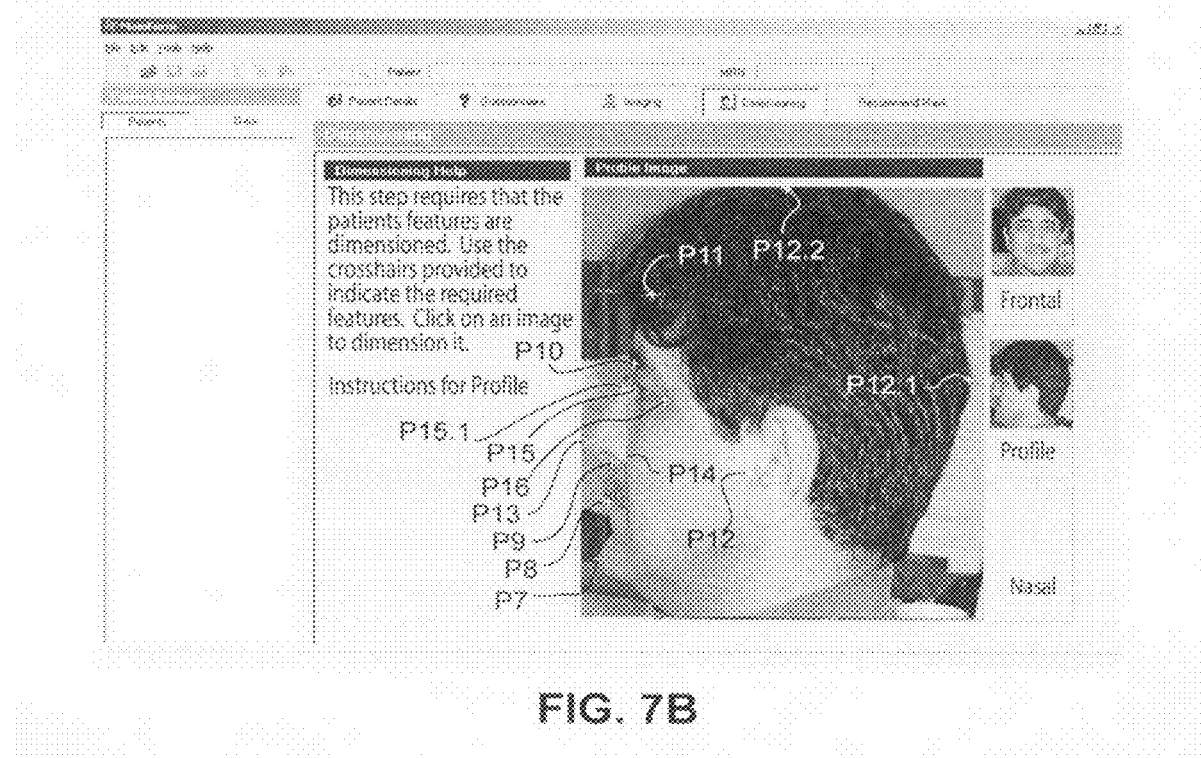
Figures 1, 7B:
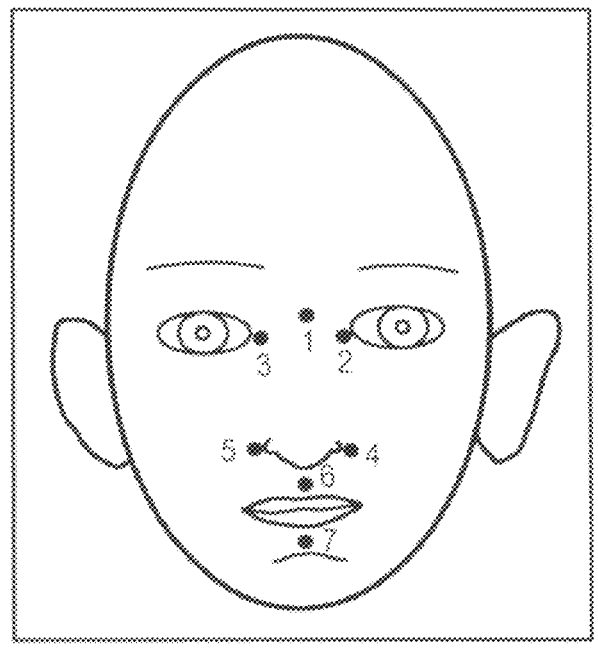
Figures 2, 7B:
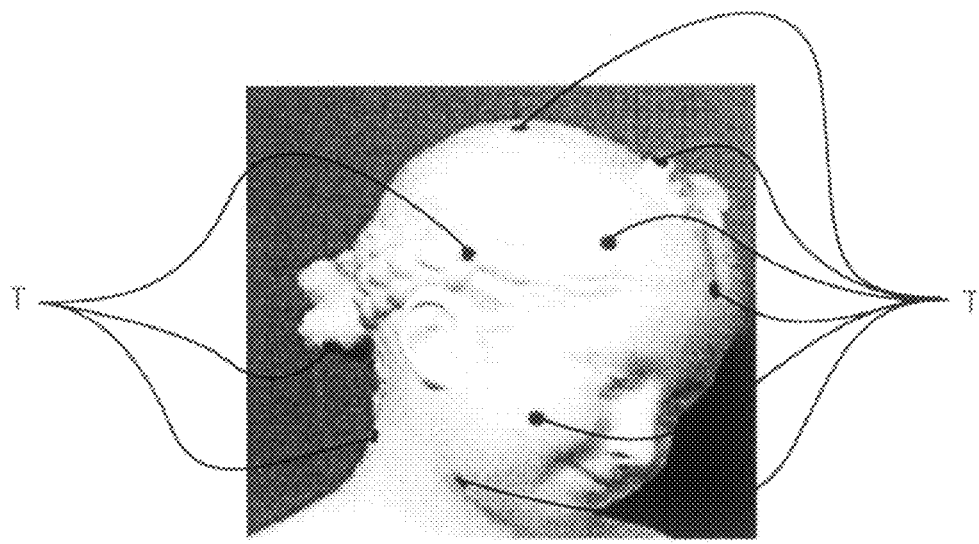
Figures 3, 7B:
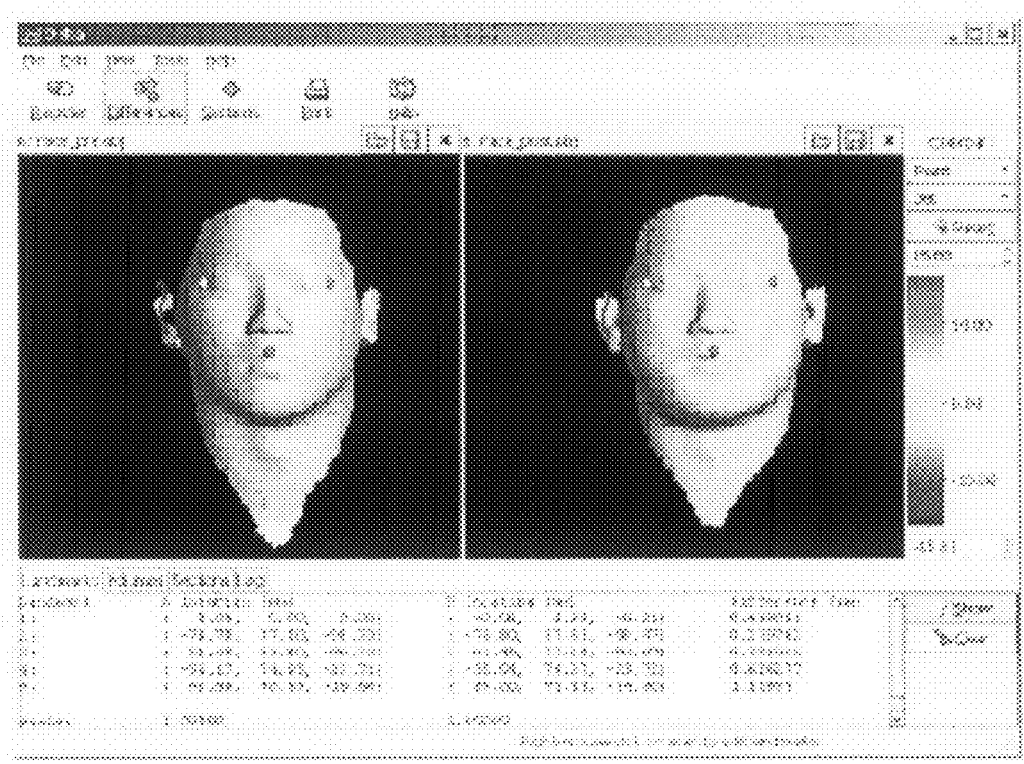

In the screenshot shown in FIG. 6, one or more images of the patient are captured and displayed on a display screen at terminal 6. The image(s) can be created using, e.g., a digital or film camera, webcam, still imaging system, and/or any system able to capture images by screen "grabbing" or video still capture, any of which may be the reader 12 described in relation to FIG. 2 above. The screenshot shown in FIG. 6 may include instructions on how to use a reader to create the recommended images.

In this embodiment, frontal and profile images of the patient are provided. However, nasal or other views can be incorporated as desired. Moreover, any reader that can transfer real time mask interfacing regions of a patient's body is readable into physical dimensions, e.g., overall dimensions or at least one plane (e.g., frontal view) can provide overall dimensions, such as nose width and head width.

After the imaging step, user input is utilized to obtain one or more dimensions from the patient's front and/or profile images. Once the image appears on the screen, as shown in FIGS. 7A and/or 7B, the patient or clinician is prompted to use the cursor to align crosshairs on the screen with various points on the patient's face. Different points will be recommended depending on whether the patient prefers nose masks or full face masks, etc. However, if the patient or clinician desires that all types of masks be considered in the selection process, then all the suggested dimensions should be entered and/or considered.

As shown in FIG. 7A, the cursor, e.g., in the shape of a crosshair, is moved to several points on the face and "clicked"

so as to derive the relative dimensions for entry into the system. For example, points P1 and P2 correspond to the sidewalls of the nostrils, i.e., the widest point of the patient's nose. Selection of additional points may result in an even better mask fit, although additional data points may not be necessary, depending on the type of mask of interest. For example, the following points can be measured to provide the best possible mask fit: point P3 (the bottom tip of the nose), point P4 (on the nasal bridge between the eyes, point P5 (the middle of the patient's forehead) and point P6 (the patient's chin), etc.

It is preferable that a comprehensive set of dimensions be obtained so that if a patient needs a full face mask, as opposed to a nasal mask, the clinician/dealer could recommend a new mask without the patient returning for a subsequent fit.

The same process is repeated for the profile image of the patient, as shown on the display in FIG. 7B. Of course, the profile image point(s) could be entered first, followed by the frontal image point(s). Using the profile image, the clinician or user will then be prompted to use the cursor to "click" on a number of points on the patient's head. For example, points P7-P16 are illustrative of the points which the patient may be prompted to enter into the system. P7-P16 are generally described as follows: P7 (chin), P8 (lips), P9 (joint between upper lip and bottom of nose), P10 (bottom of forehead), P11 (top of forehead), P12 (front of ear), P12.1 (rear of head), P12.2 (top of patient's head), P13 (tip of nose), P14 (joint between cheeks and base of nose), P15 (base of nasal bridge), P15.1 (peak of bridge between eyes), P16 (rear of eye socket where temple begins). Other points and/or dimensions could be added as desired.

Some of these points, e.g., points P13, P14, P15 and P15.1 may be relevant to use for consideration of nose masks or full face masks, but may not be relevant to consideration for use with nasal cannula. Points P10 and P11 may help with consideration of mask systems having forehead supports, by providing the slope of the patient's forehead. This information may also indicate the most appropriate adjustment setting for an adjustable forehead support, for best fit with the patient. Points P12, P12.1, P12.2 and/or P16 may be relevant for fitting a particular headgear to the patient's head.

In a preferred embodiment, frontal and profile images are all that are required to fit a mask. However, a nasal image could be used in a similar manner to the above if desired.

Once these suggested points are entered into the system, the fitting system may produce a best-fit mask system result. See FIG. 8. The result can take the form of a single mask system which is judged to be most appropriate for the patient, or the result may include a listing of two or more masks which the patient may wish to consider. The mask fitting result may be presented in order of preference. The results page may include information about mask accessories, mask system reviews, etc., or links to such information, e.g., via database 2.

Further, certain example embodiments may generate a system result suggesting multiple mask systems (e.g. alternating between two or more mask systems) that may be appropriate for a patient. For example, the patient could use a first mask system for a predetermined period of time (e.g. one day, one week, one month, etc.) and then alternate with a second mask system. Recommending multiple mask systems may be advantageous for several reasons. For example, it may not be possible to recommend a single, best-fit system (e.g. because not enough data were gathered, multiple mask systems may fit equally well, etc.). Also, different mask systems generally will fit the same patient differently (e.g. because of different materials used, different adjustment mechanisms, different points at which masks contact portions of the patient, etc.). By way of example and without limitation, an aspect of the techniques for fitting mask systems to patients described herein seeks to find the most comfortable fit for patients (e.g. by eliminating irritation areas caused by where the mask comes into contact with the patient's face, etc.). However, it may not always be possible to eliminate all irritations, especially when mask systems must be used for extended periods of time. Thus, certain example embodiments may recommend a number of mask systems for a patient. The recommendation may come in the form of a schedule, which may be displayed and/or printed for the patient. The schedule may include scheduling information, which may include the predetermined amounts of time for which a patient should wear each particular mask. A patient may rotate among, alternate, or switch between, recommended mask systems, thereby potentially reducing irritations and improving both short- and long-term comfort.

Other embodiments of the invention are shown in FIGS. 7B-1 to 7B-3. To determine the appropriate mask fit for a patient a set of predetermined points can be used that are unique to particular features of the face. FIG. 7B-1 is an example of frontal facial points that could be used to determine the appropriate mask size for a patient.

In an embodiment, the operator may select or fit curves that match shapes on the patient's face such as the frontal and profile shapes of the patient's nose. This may also be used to select sizes by comparing the curves to mask or cushion shape curves.

Still other embodiments allow different functions to be performed after image(s) and/or video(s) of the patient are acquired by the camera, web cam, or other imaging device. As noted above, certain processing may be performed automatically to generate a 2D image of one's face. The accuracy of such systems may be improved with minimal user (e.g. patient, clinician, or other human) interaction. For example, one or more stickers depicting a symbol (e.g. a cross or the like) may be supplied to the patient. Applying the symbols to the patient's face prior to imaging may allow a computer system processing the image(s) to quickly find key points on the patient's face (e.g. the points described in relation to FIGS. 7A-7B and 7B-1-7B-3). The symbols also may help the system gauge distance and/or orientation of the patients face on the basis of the fixed dimensions of the sticker in order to gain a proper measurement of the patients face. It will be appreciated that a mask, hat, template, or the like may be used in place of a sticker, and that multiple stickers (or the like) may be used. It also will be appreciated that the images may be processed by software, hardware, firmware, some combination thereof, or the like.

In certain example embodiments, once a 2D image is acquired, the patient, clinician, or operator may use a computer system to overlay 2D images of the various masks available onto the image of the patients face to determine appropriate mask sizing. Alternatively, the computer system may automatically overlay the mask templates to determine the best fitting mask system. The system may use a single image, or it may synchronize photos from multiple cameras, potentially allowing for multiple viewpoints and thus potentially better fittings. Also, in certain example embodiments, images from different angles may be used to generate a 3D contour of the patient's face. Incorporating symbols on the patient's face at predetermined positions helps reduce the processing power required when generating such contours. It also will be appreciated that the images may be processed by software, hardware, firmware, some combination thereof, or the like.

In a tangible, real-world analog to the computer-mediated systems described above, a patient may be provided with transparencies (e.g. acetate sheets) or similar other products showing the outlines of various masks (e.g. the transparencies may have outlines pre-printed on them). Then, the patient may hold the transparency or other product up to a mirror to determine the appropriate mask sizing.

In another embodiment, the measurement ranges for each dimension of the sizes of a mask may be considered. For example, if there are two sizes for a mask, small and large, the ranges may be as follows:

----A--------B--------C---- where:
Values less than A are outside range for the given dimension;
Values between A and B suit the small size (in this dimension); and
Values between B and C suit the large size (in this dimension).

This may be repeated for multiple dimensions. A lookup table or flowchart may then be used to supply a weighting for each of the sizes of the mask.

For example (extending the example above), in the case where there are two mask sizes for a given type and two dimensions under consideration, the following table may be produced:

|             | Dimension A |            |                  |        |
|-------------|-------------|------------|------------------|--------|
| Dimension B | <A          | A to B     | B to C           | >C     |
| <A          | No Fit      | No Fit     | No Fit           | No Fit |
| A to B      | No Fit      | Small (very good) Large (very poor) | Large (good) Small (poor) | No Fit |
| B to C      | No Fit      | Large (good) Small (poor) | Large (very good) Small (very poor) | No Fit |
| >C          | No Fit      | No Fit     | No Fit           | No Fit |

It is noted that the logic embodied in the selected values in the table may permit decisions such as: Choose the largest size that any of the dimensions suit.

Of course, the ranges and relative weightings may be entirely arbitrary. Ranges may be selected so that borderline values between sizes are taken into account.

2.1 Method 1: Datum Points (e.g., Using the Polhemus Cobra FastScan)

The stylus/laser pointer would be placed on points 1-7, as shown in FIG. 7B-1, in order. Thus, data would be then sent to the software fitting program to calculate the distances between points and then a recommendation for the most appropriate mask size can be made based on the dimensions.

2.2 Method 2: Datum Points (e.g., Using the Minolta Laser Scanner)

This method uses the same concept as that outlined in Method 1 of using datum points, however instead of using a laser pointer/stylus to directly identify each point, a coloured tab T, as shown in FIG. 7B-2, is placed on selected feature points. The face is then scanned using a tripod mounted Minolta laser scanner which will map the coloured points onto a 3D model, using these points the dimensions of the patient can be found using any CAD system or CAD integrated system that is capable of importing 3D meshes. An example of software systems that could do this is Geomagic, Pro Engineer, Solid Works and IDEAS.

2.3 Method 3: Delta View (Polhemus Measuring Software)

The Delta View program (Screenshot in FIG. 7B-3), from Polhemus can be used to show how the patient's face has changed between full facial scans when the initial mask recommendation was made. Changes in the patient's weight can affect the way the mask fits onto the face the patient over time, especially in barriatric applications. This software can show geometrically how the patients face has changed and the specific areas where the most change has occurred. With this information a recommendation could be made from the software as to whether the patient requires a new mask size.

2.4 Method 4: Full Facial Scan (e.g., Using the Polhemus or Minolta Scanning Systems)

The face of the patient is scanned using the 3D laser scanner, the image is imported into a CAD package and the measurement analysis with the CAD package is used to measure the dimensions that are critical for fitting the mask.

The system may allow a clinician to override the choice, and may include "fuzzy logic" that could learn to adapt to a particular clinician's fit methods or needs. "Fuzzy logic" is optional and if included, it need not be enabled for each system user.

3. Exemplary Camera Mounts

Figures 7, 8B:
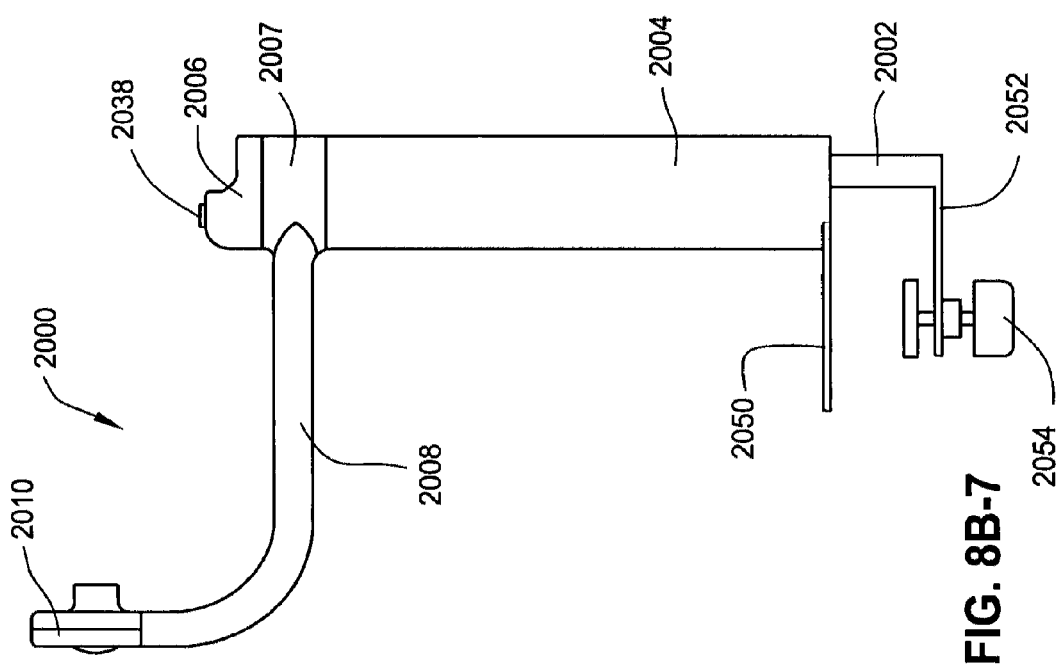

As described above, e.g., especially in relation to FIGS. 6-7B, the effort in taking several measurements manually is replaced with using a digital image to indicate the measurements. Preferably, the clinician or patient should align his head with a camera so as to provide for consistent and accurate results. This may be achieved by providing a template, e.g., a head support, for use with the camera. The template preferably would be fixed in relation to the camera such that the patient's head assumes a predetermined orientation. In addition, the patient's head will be preferably spaced from the camera at a predetermined distance/location, so that measurement results are consistent from patient to patient. Alternatively, the measured facial dimensions can be calibrated for each image.

The following illustrates several head supports and camera mounts according to alternative embodiments of the present invention, which may share common characteristics and features. It is to be understood that one or more features of any one embodiment may be combinable with one or more features of the other embodiments. In addition, each single feature or combination of features in any of the embodiments may constitute an additional embodiment.

3.1 First Illustrated Embodiment of Head Support and Camera Mount

FIGS. 8A-1 to 8A-3 illustrate a head support and camera mount assembly 500 according to an embodiment of the present invention. Assembly 500 includes a base 502 configured to clamp onto the side of a table or desktop. Of course, base 502 could rest on the top of a table or desk. Base 502 supports an extrusion or upright 504 with an upper end including a chin support 506 for the patient. Extrusion 504 may also support an arm 508 that is preferably pivotably mounted to the extrusion 504 via a pivot joint 507. Arm 508 includes a distal end to support an imaging device 510, e.g., a camera. Arm 508 may be mechanically operated. In certain example embodiments, the arm may be adjusted (e.g. by height using a telescopy arrangement, etc.) to accommodate different people with different characteristics (e.g. people of different heights, head sizes, etc.).

The camera mount is designed to enable consistent frontal and profile images to be taken of a patient's face when his or her head is resting on chin support 506. Imaging device 510 is supported at the end of the arm 508 attached in a fixed position, e.g., by a screw from the base and plugs at the sides. It will be appreciated that a light may also be attached to the arm or the imaging device directly. It also may be present proximate to any part of the assembly. The arm 508 locates on pivot 507 and rotates through a predetermined extent, e.g., about 90 degrees. Arm 508 may lock or rotate between or into two fixed positions, e.g., by detents or the like, to provide front and profile camera images without the patient moving or disassembly of any components. Arm 508 may swing within a groove provided in pivot 507. Pivot 507 may include stops at each extreme end of the desired movement angle, e.g., about 90°. As shown in FIG. 8A-2, for example, the arm 508 rotates on the pivot 507 via the 90° slot 520 in the arm 508. A locking mechanism uses a small tab 522 with a bump 524 that can be seen on the arm 508. The chin rest 506 is located via projections 527 that engage with the holes 526 to clamp the arm (see FIGS. 8A-2 and 8A-3). The tab 522 on the arm 508 deflects during rotation and the bump aligns with the notches 528 visible on the underside of the chin rest in the two 90° locations (see FIG. 8A-3). The circular button 530 that can be seen on the pivot 507 locates the pivot by a snap fit with a hole the extrusion 504. The inclined surface between the pivot block and extrusion is one method for helping to locate the components in a uniform manner.

Chin support 506 is designed to enable a patient to comfortably rest his head and locate his face at a known fixed distance from the camera 510. Chin support 506 attaches to the pivot 507 and remains fixed when the camera arm is rotated. It is easily removable for cleaning. The arm length is designed so that the distance between the camera and patient's face is sufficient to capture all of the required facial dimensions.

Extrusion 504 is a strong and stable support column for the system. The extrusion's height above the standard desk/table enables a comfortable sitting posture for when the patient is resting his chin. The pivot 507 clips into the top of the extrusion and the other end of the extrusion is attached to a base plate/clamp 502.

Base/clamp 502 provides a secure attachment of the entire camera rig to the top of a desk or table. Camera mount can be disassembled for flat packing. Camera mount can be easily assembled by the user.

3.2 Alternative Embodiments of Head Support and Camera Mount

FIGS. 8B-1 to 8Y-2 illustrate various features of a head support and camera mount according to alternative embodiments of the present invention. Each illustrated embodiment may include one or more of the following features:

1. Rotatable arm being lockable in an in-use configuration and a collapsed configuration. A squeeze button may be provided at the hinge region between the arm and the upright to allow rotation of the arm when squeezed and prevent rotation (i.e., lock the arm) when not squeezed. The hinge may be dampened to prevent the arm from banging against the upright if dropped.

2. Telescopic pneumatic system that provides controlled, steady height adjustment of the upright. The pneumatic system may support the weight of the upright to facilitate upward movement of the upright. In this arrangement, the upright would need to be pushed downwardly to move the upright downwardly. A push button may be provided to the pneumatic system, e.g., on the upright, which allows height adjustment when pressed but maintains the height of the upright when released. The upright may be raised by 10% to 500% of its height, e.g., 150 mm.

3. Base of arm may be selectively slidable up and down the upright.

4. Camera and/or camera housing may be fixed or rotatable on the end of the arm.

5. A slidably mounted bottom upright member that may be slid out of the base of the upright. The bottom upright has a flange with a clamp member screw threaded therethrough. An upper end of the clamp member bears against an undersurface of the table onto which the device is mounted. The side of the bottom upright member then cams against an inside surface of the upright. An embodiment based on the same principle with a slidable sleeve is shown in FIG. 8L-1. The cam clamping effect in these embodiments is similar to that used in common G-clamps.

6. Bushings provided to stop the patient from squashing his/her finger between telescoping parts.

7. Arm rotates laterally as well as up and down. The arm may rotate laterally through approximately 90 degrees in both directions. This arrangement allows the camera to take side photos of the patient's face. There may be a button to allow this rotation and the button may be detented in at least three positions, e.g., straight ahead, right side, and left side.

8. Device can be made from steel, plastic, and/or aluminum. However, other materials are possible.

3.2.1 First Alternative Embodiment

FIGS. 8B-1 to 8B-18 illustrate various views of a head support and camera mount assembly 2000 according to another embodiment of the present invention. As illustrated, the head support and camera mount assembly 2000 includes a base 2002 adapted to clamp onto the side of a table or desktop, an upright 2004 including a chin support 2006, and an arm 2008 that supports an imaging device 2010, e.g., camera.

The arm 2008 is mounted to a pivot joint 2007 that allows the arm 2008 to rotate laterally with respect to the upright 2004, e.g., 90 degrees in both directions. In addition, the pivot joint 2007 includes a hinge region that allows the arm 2008 to rotate up and down between an in-use configuration (see solid lines in FIGS. 8B-15 and 8B-17) and a collapsed configuration (see dashed lines in FIGS. 8B-15 and 8B-17).

The upright 2004 includes a telescopic pneumatic system to control height adjustment of the upright 2004. As schematically shown in FIG. 8B-18, the upright 2004 includes a first pneumatic cylinder 2030 provided to the base, a second pneumatic cylinder 2032 telescopically engaged with the first pneumatic cylinder 2030, and an outer tube 2034 attached, e.g., by a screw thread arrangement, to the second pneumatic cylinder 2032. An actuator 2036 is operatively connected to the second pneumatic cylinder 2032 that allows the second pneumatic cylinder 2032 to move into and out of the first pneumatic cylinder 2030, which adjusts the height of the upright 2004. A button 2038, e.g., rubber button, is provided to the actuator 2036 to manually actuate the actuator 2036.

As best shown in FIGS. 8B-6 and 8B-7, the button 2038 is provided to a top of the upright 2004, e.g., on top of the chin support 2006. FIG. 8B-5 illustrates the aperture 2040 in the chin support 2006 for the button 2038. The button 2038 is sealed, cleanable, and may be flush or below the chin support's surface. The flush mounting may help to prevent the patient's chin from pressing the button 2038. In an alternative embodiment, the button 2038 and actuator 2036 may be axially offset and operably connected by a lever.

The base 2002 is in the form of a clamp including an upper flange 2050 that supports the upright 2004 and a lower flange 2052 that supports a clamp member 2054 screw threaded therethrough. The lower flange 2052 includes an extrusion 2056 that engages within a corresponding opening 2058 provided in the upper flange 2050 to support the lower flange 2052 on the upper flange 2050 (see FIGS. 8B-8 and 8B-9).

FIG. 8B-13 illustrates the engagement between the upright 2004, upper flange 2050, and lower flange 2052. FIG. 8B-13B illustrates an alternative arrangement to that shown in FIG. 8B-13. As illustrated, the cross-sectional configuration of the upright 2004, upper flange 2050, and/or lower flange 2052 may vary. It is noted that the hook-like areas in the cross-section are adapted to receive fasteners (self-tapping or otherwise), e.g., screws.

3.2.2 Second Alternative Embodiment

FIGS. 8C-1 to 8C-3 illustrate various views of a head support and camera mount assembly 2100 according to another embodiment of the present invention. As illustrated, the head support and camera mount assembly 2100 includes a base 2102 adapted to clamp onto the side of a table or desktop, an upright 2104 including a chin support 2106, and an arm 2108 that supports an imaging device 2110, e.g., camera.

The arm 2108 is mounted to a pivot joint 2107 that allows the arm 2108 to rotate laterally with respect to the upright 2104, e.g., 90 degrees in both directions. In addition, the pivot joint 2107 includes a hinge region that allows the arm 2108 to rotate up and down between an in-use configuration (see FIGS. 8C-1 and 8C-3) and a collapsed configuration (see FIG. 8C-2).

3.2.3 Third Alternative Embodiment

FIGS. 8D-1 to 8D-3 illustrate various views of a head support and camera mount assembly 2200 according to another embodiment of the present invention. As illustrated, the head support and camera mount assembly 2200 includes a base 2202 adapted to clamp onto the side of a table or desktop, an upright 2204 including a chin support 2206, and an arm 2208 that supports an imaging device 2210, e.g., camera.

The arm 2208 is mounted to a pivot joint 2207 that allows the arm 2208 to rotate laterally with respect to the upright 2204, e.g., 90 degrees in both directions. In addition, the pivot joint 2207 includes a hinge region that allows the arm 2208 to rotate up and down between an in-use configuration (see FIGS. 8D-1 and 8D-3) and a collapsed configuration (see FIG. 8D-2). As illustrated, the pivot joint 2207 is provided to a lower region of the upright 2204, e.g., with respect to arrangement shown in FIGS. 8C-1 to 8C-3.

3.2.4 Fourth Alternative Embodiment

FIGS. 8E-1 to 8E-2 illustrate various views of a head support and camera mount assembly 2300 according to another embodiment of the present invention. As illustrated, the head support and camera mount assembly 2300 includes a base 2302 adapted to clamp onto the side of a table or desktop, an upright 2304 including a chin support 2306, and an arm 2308 that supports an imaging device 2210, e.g., camera.

The arm 2308 is mounted to a pivot joint 2307 that allows the arm 2208 to rotate laterally with respect to the upright 2304, e.g., 90 degrees in both directions. As illustrated, the assembly 2300 includes a tubing arrangement, e.g., square upright tubing and L-shaped arm, similar to the assembly 2000 described above.

3.2.5 Fifth Alternative Embodiment

Figures 8, 8B, 9, 10, 11, 12:
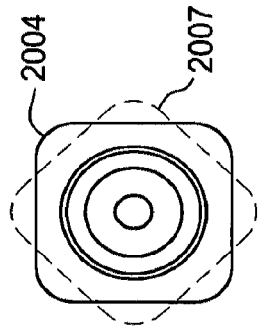
Figures 8, 8B, 9, 10, 11, 12, 13:
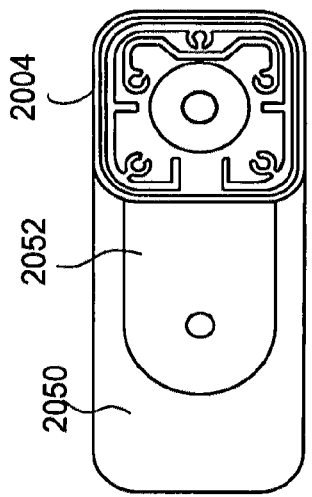
Figures 8, 8B, 9, 10:
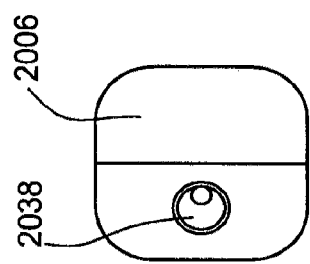
Figures 8, 8B, 9, 10, 11:
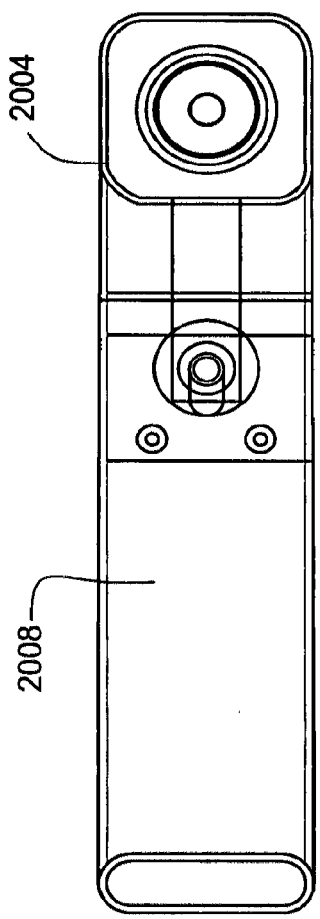
Figures 8, 8B, 9, 10, 11, 12, 13, 14, 15, 16, 17, 18:
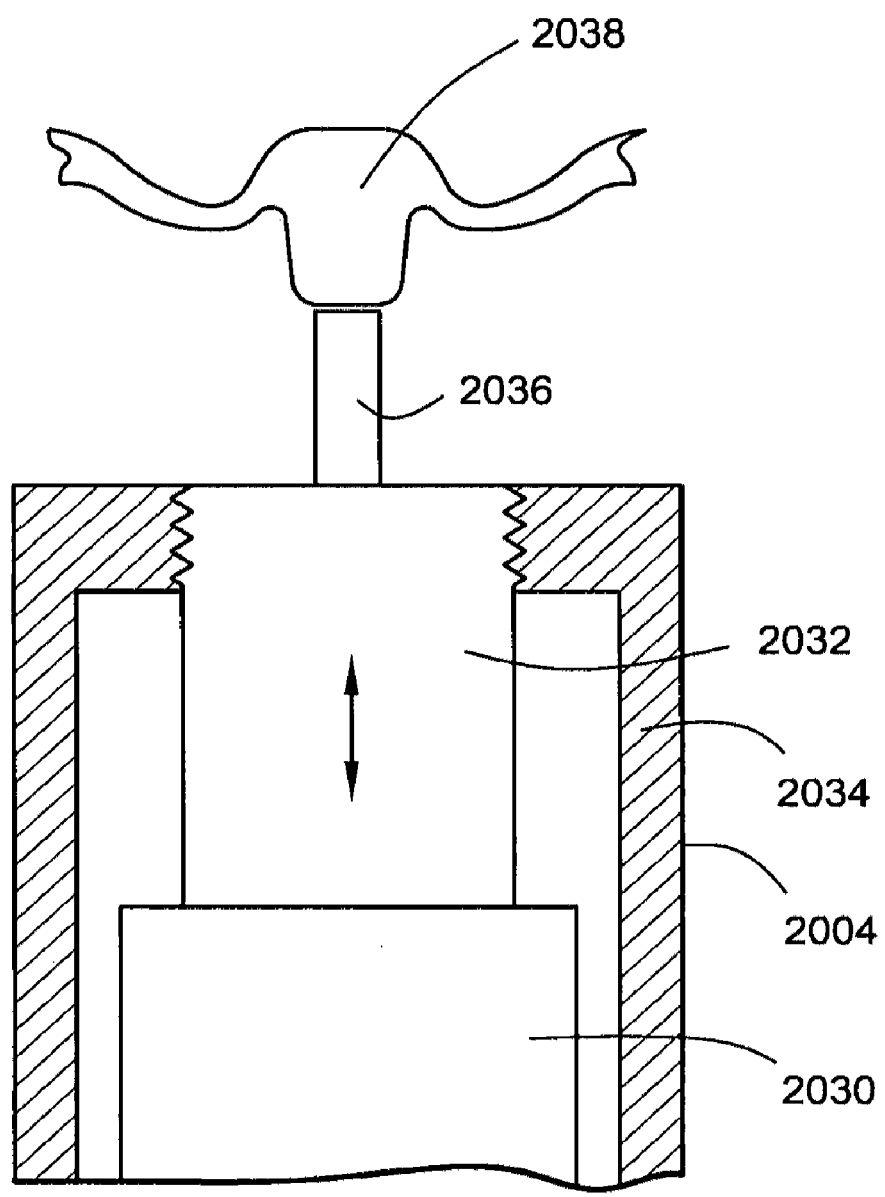
Figures 2, 8F:
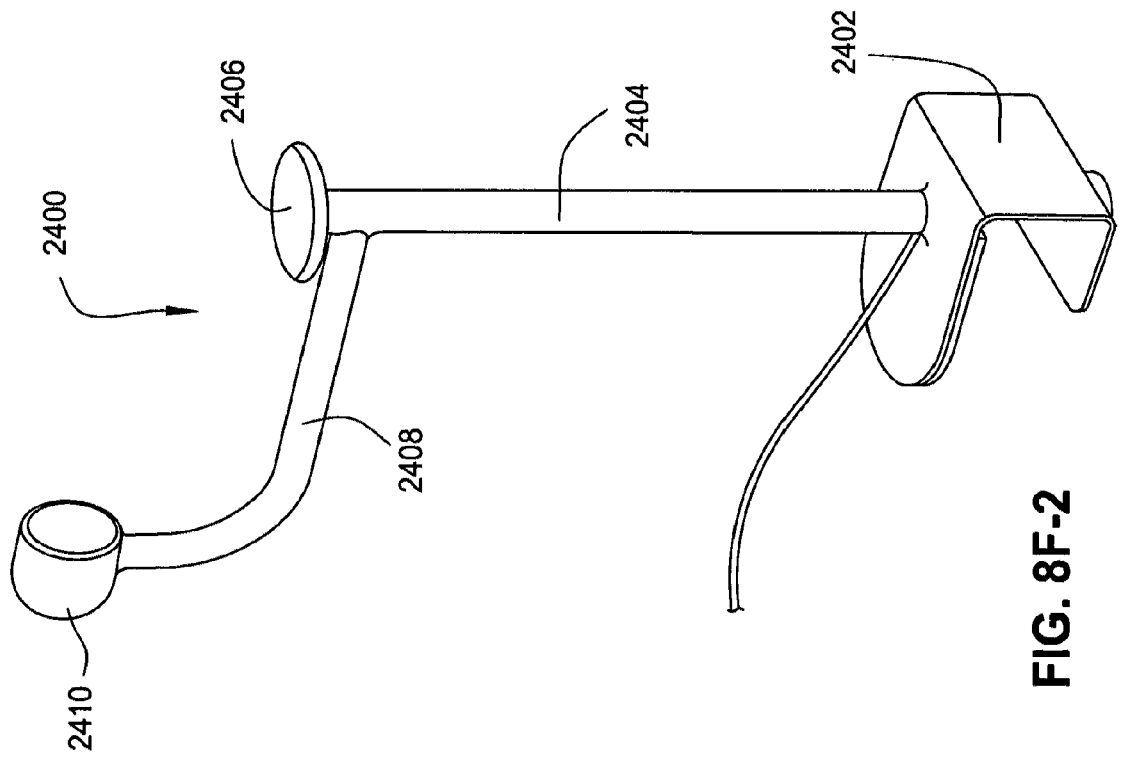
Figures 1, 8F:
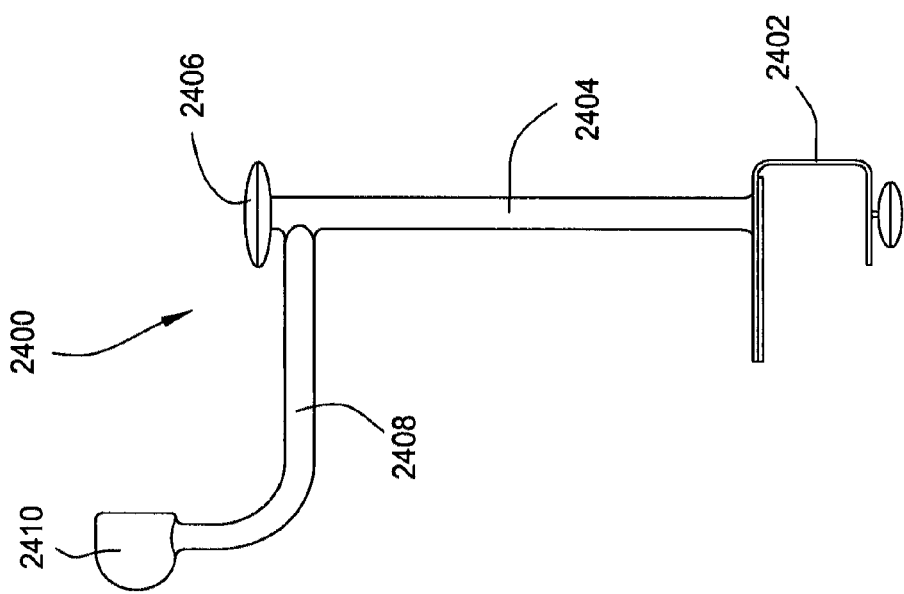

FIGS. 8F-1 to 8F-2 illustrate various views of a head support and camera mount assembly 2400 according to another embodiment of the present invention. As illustrated, the head support and camera mount assembly 2400 includes a base 2402 adapted to clamp onto the side of a table or desktop, an upright 2404 including a chin support 2406, and an arm 2408 that supports an imaging device 2410, e.g., camera.

The arm 2408 may rotate laterally via a pivot joint provided to the upright 2404. Alternatively, the arm 2408 may rotate laterally along with the upright 2404 that may be rotatable with respect to the base 2402. As illustrated, the upright 2404 and arm 2408 include relatively small diameter circular tubing.

3.2.6 Sixth Alternative Embodiment

Figures 2, 8G:
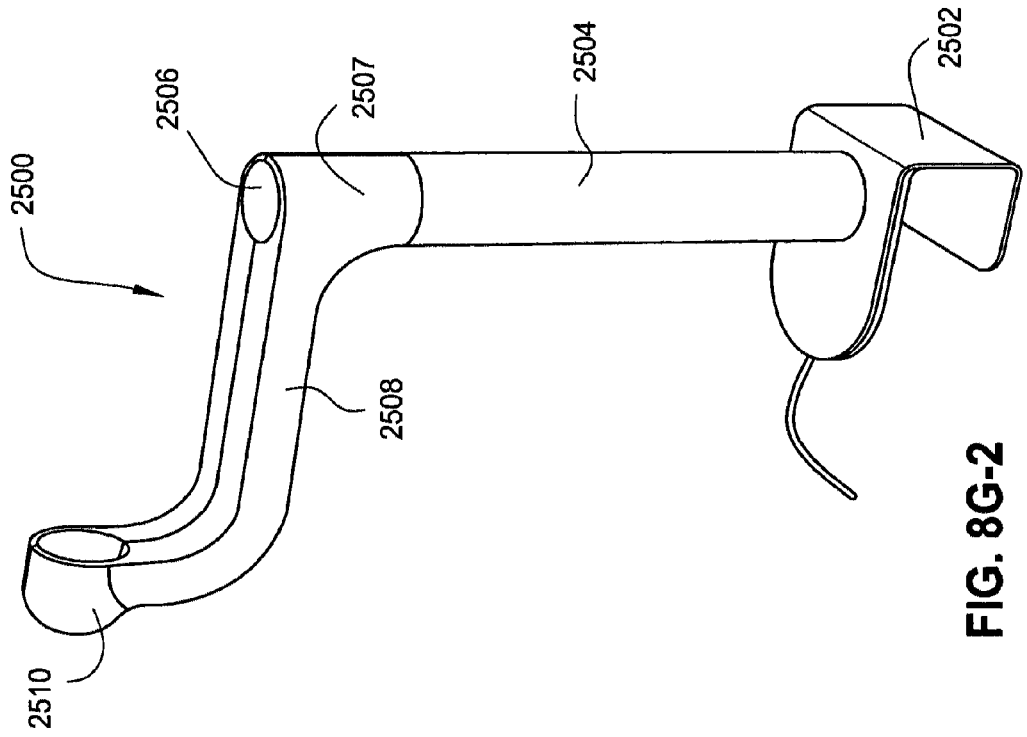
Figures 1, 8G:
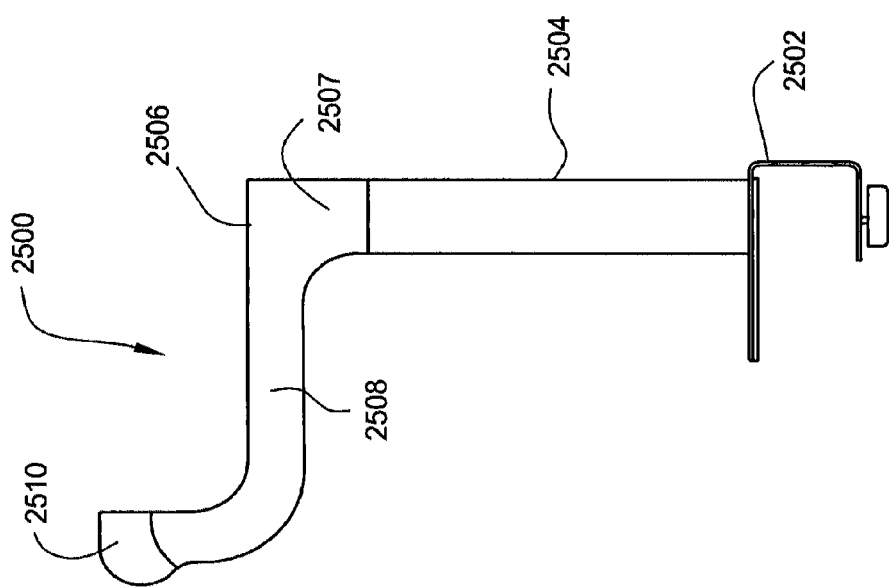

FIGS. 8G-1 to 8G-2 illustrate various views of a head support and camera mount assembly 2500 according to another embodiment of the present invention. As illustrated, the head support and camera mount assembly 2500 includes a base 2502 adapted to clamp onto the side of a table or desktop, an upright 2504 including a chin support 2506, and an arm 2508 that supports an imaging device 2510, e.g., camera.

The arm 2508 includes a pivot joint 2507, e.g., integrally formed in one-piece therewith, that allows the arm 2508 to rotate laterally with respect to the upright 2504, e.g., 90 degrees in both directions.

3.2.7 Seventh Alternative Embodiment

FIGS. 8H-1 to 8H-3 illustrate various views of a head support and camera mount assembly 2600 according to another embodiment of the present invention. As illustrated, the head support and camera mount assembly 2600 includes a base 2602 adapted to clamp onto the side of a table or desktop, an upright 2604 including a chin support 2606, and an arm 2608 that supports an imaging device 2610, e.g., camera.

The arm 2608 is pivotally mounted to a joint 2607 that allows the arm 2608 to rotate up and down between an in-use configuration (see FIG. 8H-2) and a collapsed configuration (see FIG. 8H-1). The joint 2607 is also slidably mounted within a track portion 2660 provided to the upright 2604 (see FIG. 8H-3) which allows the arm to slide up and down with respect to the upright 2604, e.g., for collapsing as shown in FIG. 8H-1.

The imaging device 2610 may also be pivotally mounted to the arm 2608 to allow adjustment of the imaging device 2610 during use and/or for storage.

The arm 2608 may rotate laterally along with the upright 2604 that may be rotatable with respect to the base 2602.

3.2.8 Eighth Alternative Embodiment

Figures 1, 2, 8I:
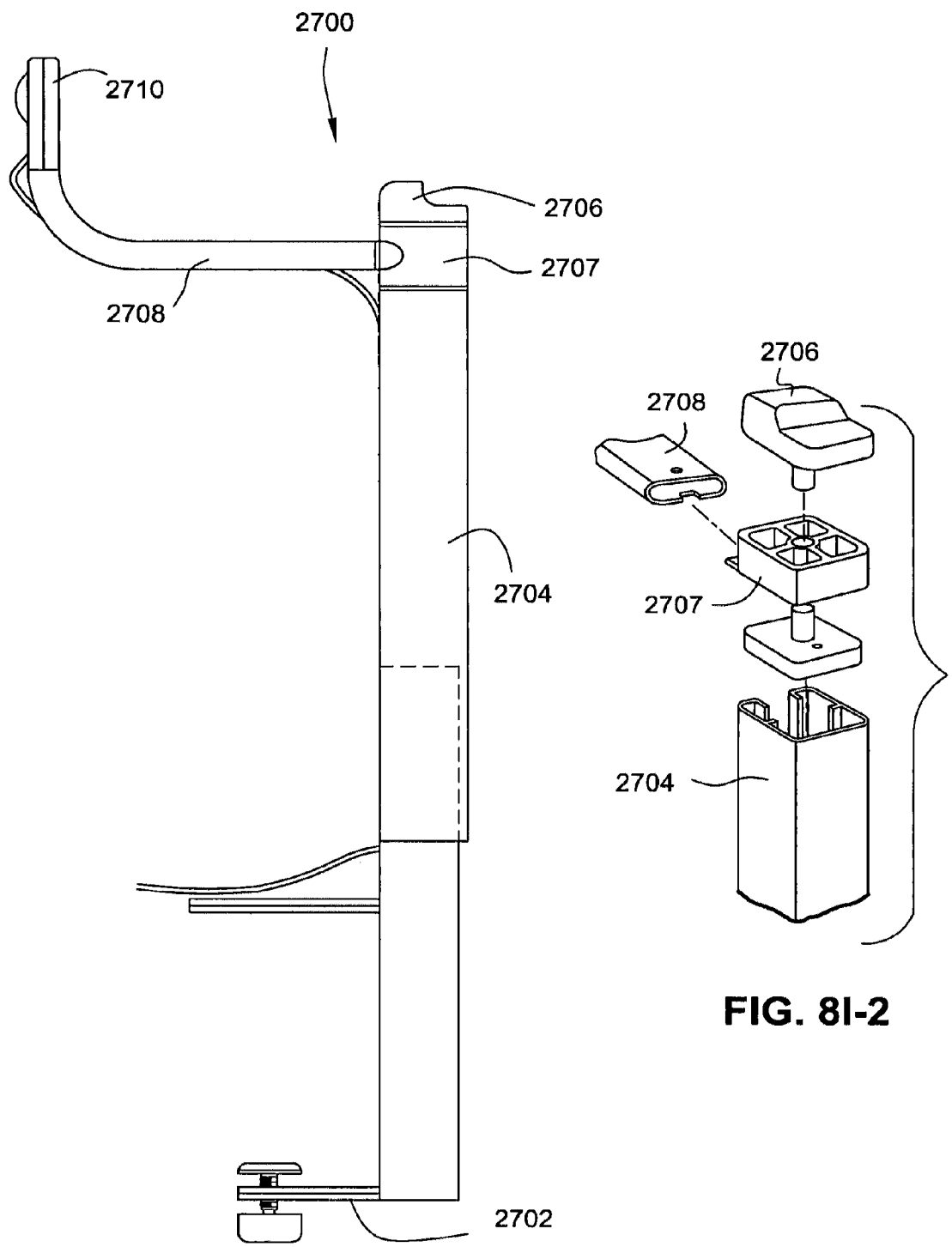

FIGS. 8I-1 to 8I-2 illustrate various views of a head support and camera mount assembly 2700 according to another embodiment of the present invention. As illustrated, the head support and camera mount assembly 2700 includes a base 2702 adapted to clamp onto the side of a table or desktop, an upright 2704 including a chin support 2706, and an arm 2708 that supports an imaging device 2710, e.g., camera.

The arm 2708 is mounted to a pivot joint 2707 that allows the arm 2708 to rotate laterally with respect to the upright 2704, e.g., 90 degrees in both directions. The upright 2704 may include a telescopic arrangement to control height adjustment of the upright 2704.

3.2.9 Ninth Alternative Embodiment

FIGS. 8J-1 to 8J-2 illustrate various views of a head support and camera mount assembly 2800 according to another embodiment of the present invention. As illustrated, the head support and camera mount assembly 2800 includes a base 2802 adapted to clamp onto the side of a table or desktop, an upright 2804 including a chin support 2806, and an arm 2808 that supports an imaging device 2810, e.g., camera.

The arm 2808 is pivotally mounted to a joint 2807 that allows the arm 2808 to rotate up and down between an in-use configuration and a collapsed configuration. The joint 2807 may also be rotatable with respect to the upright 2804, e.g., via pivot pin 2860 provided to the upright 2804 (see FIG. 8J-2).

Also, the upright 2804 may include a telescopic arrangement to control height adjustment of the upright 2804.

3.2.10 Tenth Alternative Embodiment

Figures 1, 8K:
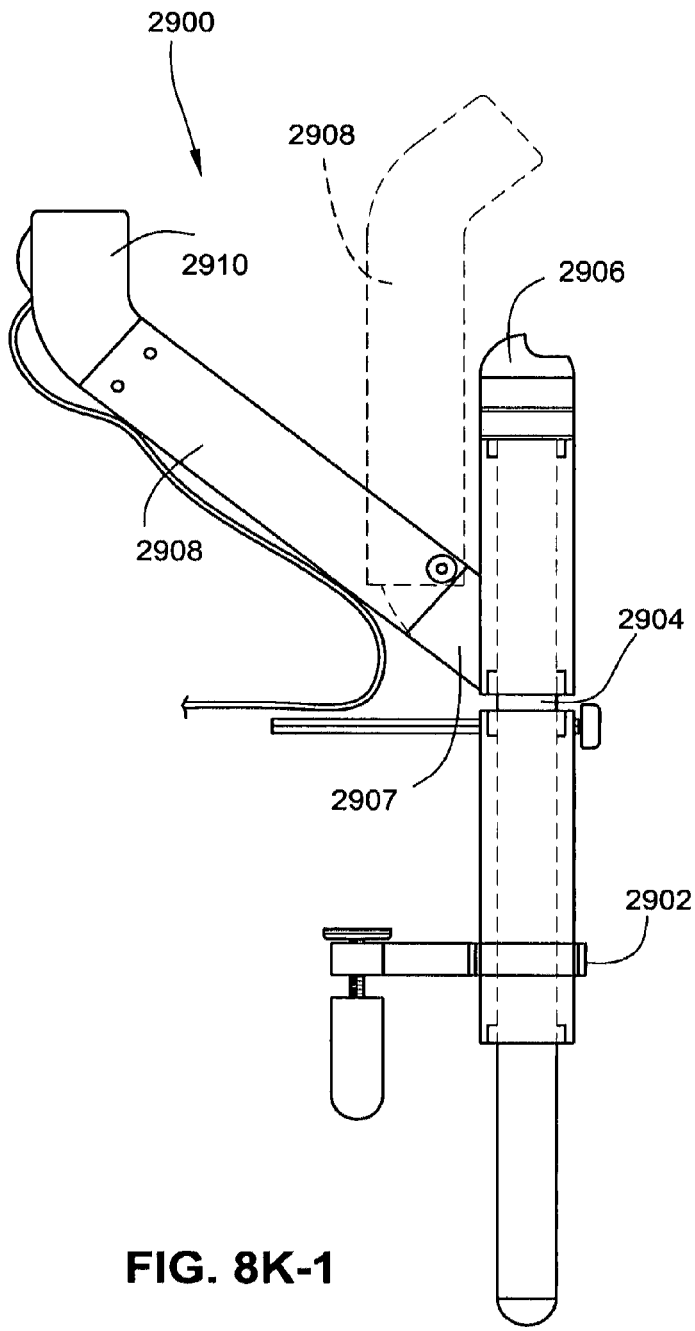
Figures 2, 8K:
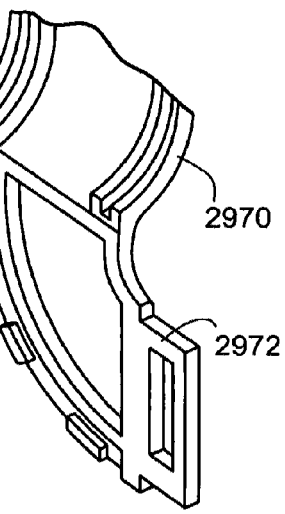
Figures 3, 8K:
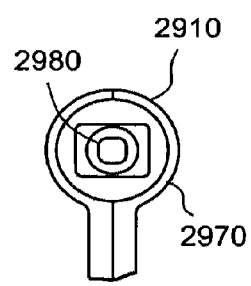

FIGS. 8K-1 to 8K-3 illustrate various views of a head support and camera mount assembly 2900 according to another embodiment of the present invention. As illustrated, the head support and camera mount assembly 2900 includes a base 2902 adapted to clamp onto the side of a table or desktop, an upright 2904 including a chin support 2906, and an arm 2908 that supports an imaging device 2910, e.g., camera.

The arm 2908 is pivotally mounted to a joint 2907 that allows the arm 2908 to rotate up and down between an in-use configuration (solid lines in FIG. 8K-1) and a collapsed configuration (dashed lines in FIG. 8K-2).

The joint 2907 and arm 2908 thereof may rotate laterally with respect to the upright 2904. Also, the upright 2904 may include a telescopic arrangement to control height adjustment of the upright 2904.

FIG. 8K-2 illustrates a portion of a housing 2970 that supports a camera for the imaging device 2910. As illustrated, the housing 2970 includes a connecting portion 2972 adapted to connect to the arm 2908.

FIG. 8K-3 is a front view of the imaging device 2910 showing camera 2980 and housing 2970.

3.2.11 Eleventh Alternative Embodiment

FIGS. 8L-1 to 8L-3 illustrate various views of a head support and camera mount assembly 3000 according to another embodiment of the present invention. As illustrated, the head support and camera mount assembly 3000 includes a base 3002 adapted to clamp onto the side of a table or desktop, an upright 3004 including a chin support 3006, and an arm 3008 that supports an imaging device 3010, e.g., camera.

The arm 3008 includes a pivot joint 3007, e.g., integrally formed in one-piece therewith, that allows the arm 3008 to rotate laterally with respect to the upright 3004, e.g., 90 degrees in both directions.

The upright 3004 may include a telescopic arrangement for height adjustment.

FIG. 8L-2 illustrates a housing including first and second housing parts 3070, 3071, e.g., molded of plastic, for the imaging device 3010 that cooperate to support a camera 3080. As illustrated, the housing parts 3070, 3071 each include a connecting portion 3072 adapted to connect to the arm 3008. Each housing part 3070, 3071 also includes a support 3074 adapted to support a respective end of a chassis 3082 that holds the camera 3080 (see FIG. 8L-3). A front cover 3075 is provided to the housing with a viewing window 3077 for the camera 3080 to see through. In addition, a removable and/or pivotable cover 3076 is provided to the housing to access the camera 3080, e.g., pivot cover ¼ turn to access camera.

3.2.12 Twelfth Alternative Embodiment

FIGS. 8M-1 to 8M-3 illustrate various views of a head support and camera mount assembly 3100 according to another embodiment of the present invention. As illustrated, the head support and camera mount assembly 3100 includes a base 3102 adapted to clamp onto the side of a table or desktop, an upright 3104 (e.g., constructed of extruded aluminum) including a chin support 3106 (e.g., molded silicone), and an arm 3108 (e.g., constructed of extruded aluminum) that supports an imaging device 3110, e.g., camera.

The arm 3108 is mounted to a pivot joint 3107 (e.g., cast aluminum or nylon) that allows the arm 3108 to rotate laterally with respect to the upright 3104, e.g., 90 degrees in both directions.

FIG. 8M-3 illustrates a section of the upright 3104. As illustrated, the upright 3104 includes a track portion 3160 that slidably receives a slider 3151 provided to flange 3150 (see FIG. 8M-2). This arrangement allows the flange 3150 to slide up and down the upright 3104 for clamping purposes with the base 3102.

3.2.13 Thirteenth Alternative Embodiment

Figures 1, 8N:
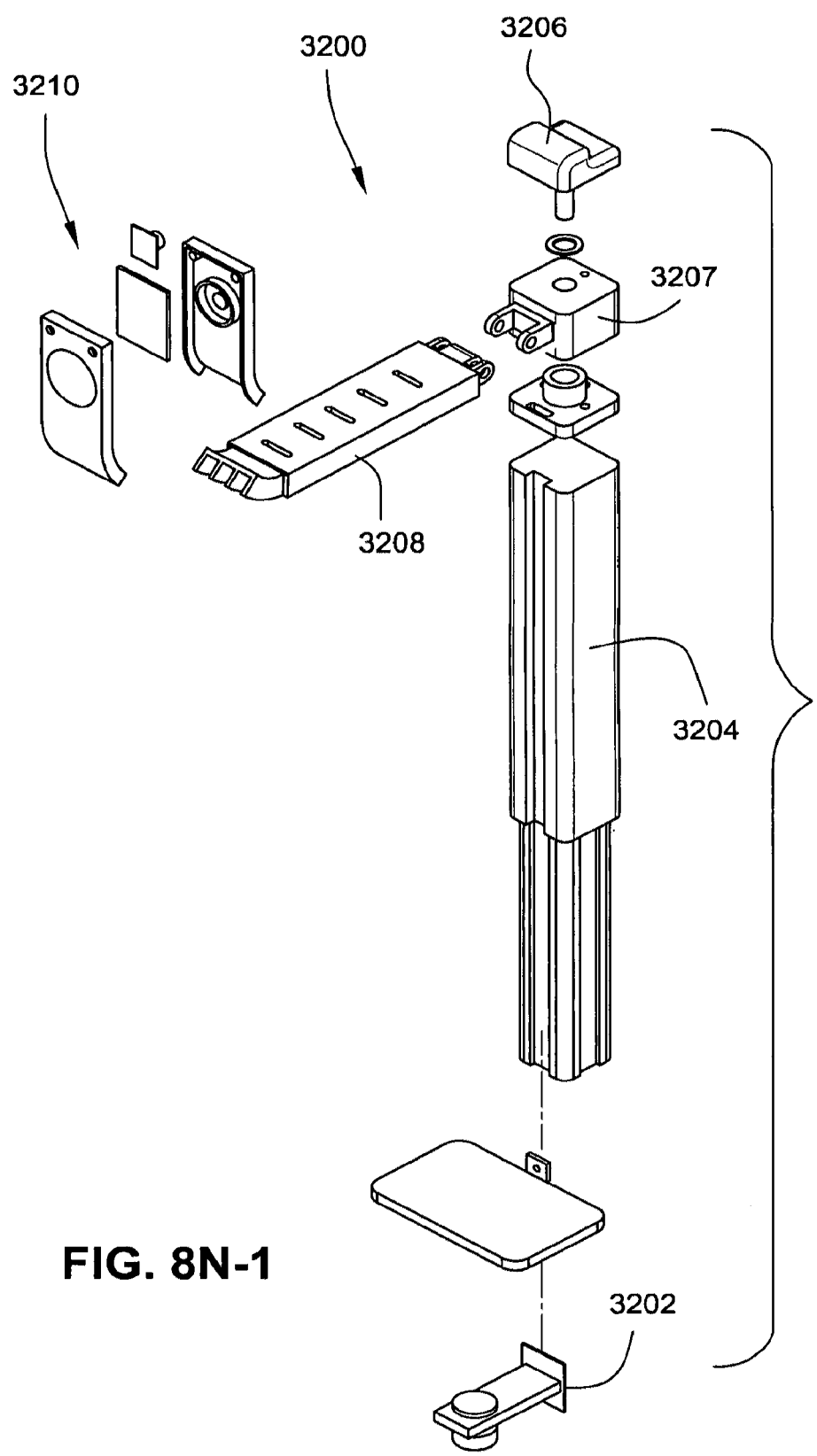
Figures 2, 3, 8N:
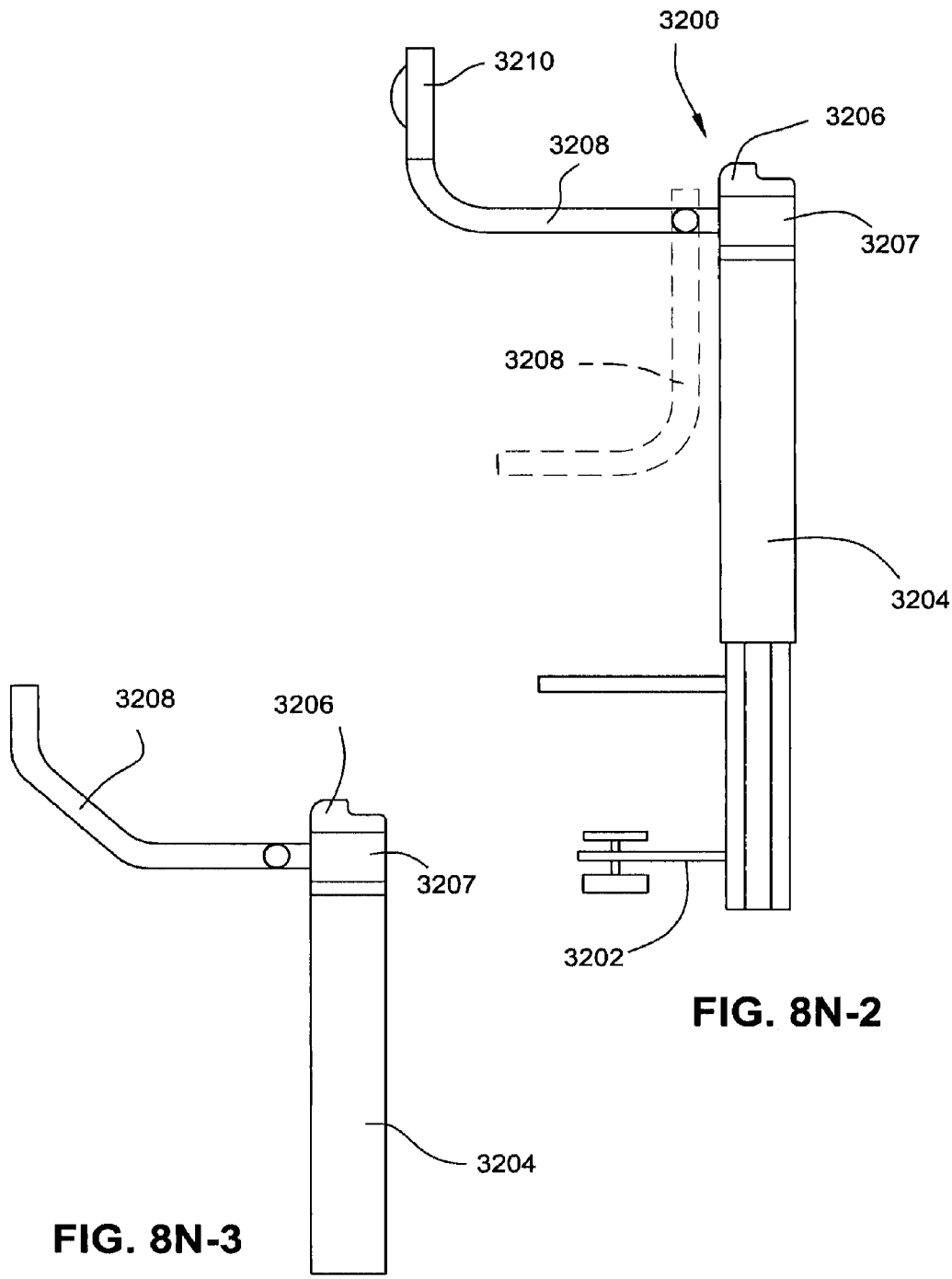

FIGS. 8N-1 to 8N-2 illustrate various views of a head support and camera mount assembly 3200 according to another embodiment of the present invention. As illustrated, the head support and camera mount assembly 3200 includes a base 3202 adapted to clamp onto the side of a table or desktop, an upright 3204 including a chin support 3206, and an arm 3208 that supports an imaging device 3210, e.g., camera.

The arm 3208 is mounted to a pivot joint 3207 that allows the arm 3208 to rotate laterally with respect to the upright 3204, e.g., 90 degrees in both directions. In addition, the pivot joint 3207 includes a hinge region that allows the arm 3208 to rotate up and down between an in-use configuration (solid lines in FIG. 8N-2) and a collapsed configuration (dashed lines in FIG. 8N-2).

The upright 3204 may include a telescopic arrangement to control height adjustment of the upright 3204.

FIG. 8N-3 illustrates an alternative configuration of the arm 3208.

3.2.14 Fourteenth Alternative Embodiment

Figures 1, 8P:
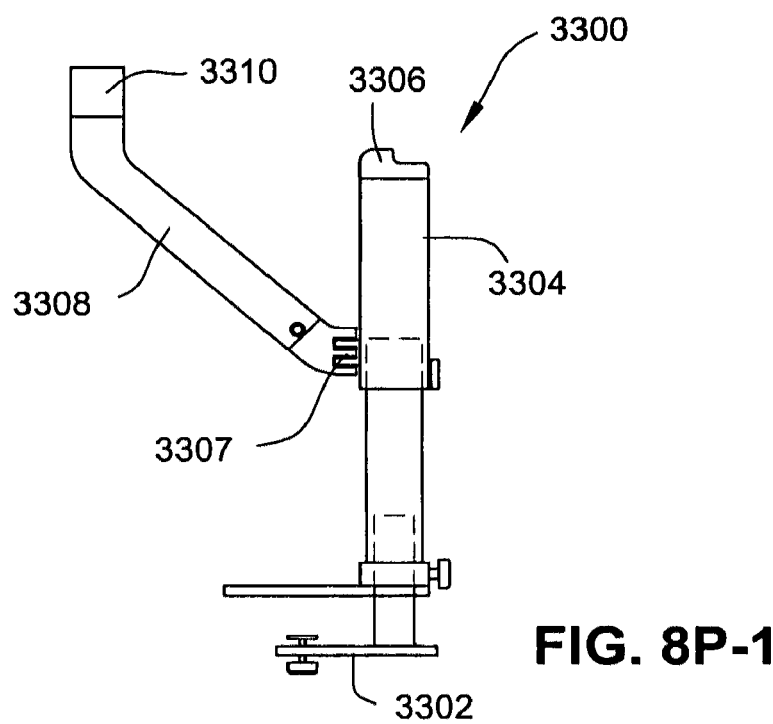

FIG. 8P-1 illustrates a head support and camera mount assembly 3300 according to another embodiment of the present invention. As illustrated, the head support and camera mount assembly 3300 includes a base 3302 adapted to clamp onto the side of a table or desktop, an upright 3304 including a chin support 3306, and an arm 3308 that supports an imaging device 3310, e.g., camera.

The arm 3308 is mounted to a hinge 3307 provided to the upright 3304 that allows the arm 3308 to rotate laterally with respect to the upright 3304, e.g., 90 degrees in both directions.

The upright 3304 may include a telescopic arrangement to control height adjustment of the upright 3304.

3.2.15 Fifteenth Alternative Embodiment

Figures 1, 8Q:
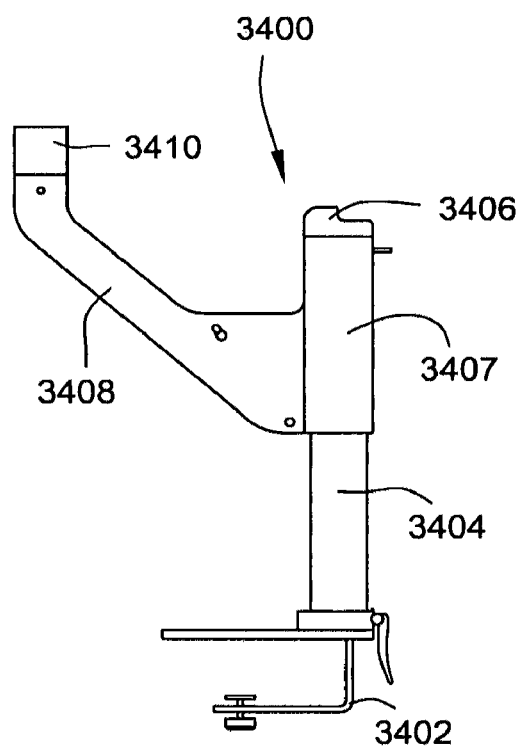

FIG. 8Q-1 illustrates a head support and camera mount assembly 3400 according to another embodiment of the present invention. As illustrated, the head support and camera mount assembly 3400 includes a base 3402 adapted to clamp onto the side of a table or desktop, an upright 3404 including a chin support 3406, and an arm 3408 that supports an imaging device 3410, e.g., camera.

The arm 3408 includes a pivot joint 3407, e.g., integrally formed in one-piece therewith, that allows the arm 3408 to rotate laterally with respect to the upright 3404, e.g., 90 degrees in both directions.

3.2.16 Sixteenth Alternative Embodiment

Figures 1, 8R:
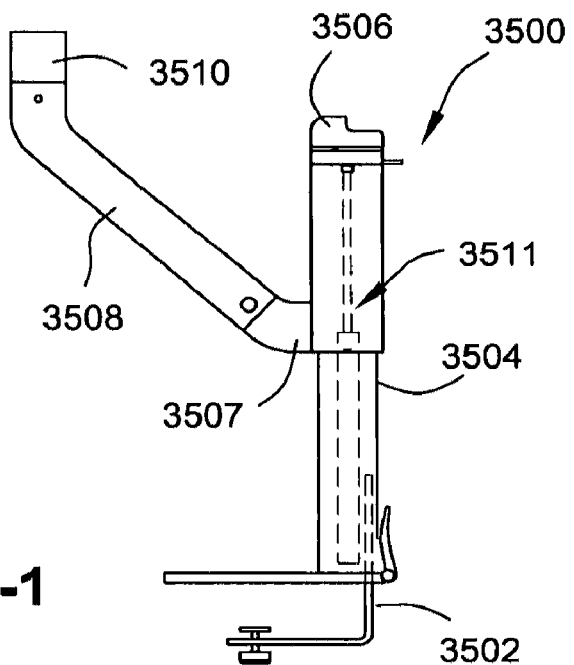

FIG. 8R-1 illustrates a head support and camera mount assembly 3500 according to another embodiment of the present invention. As illustrated, the head support and camera mount assembly 3500 includes a base 3502 adapted to clamp onto the side of a table or desktop, an upright 3504 including a chin support 3506, and an arm 3508 that supports an imaging device 3510, e.g., camera.

The arm 3508 is pivotally mounted to a joint 3507 that allows the arm 3508 to rotate up and down between an in-use configuration and a collapsed configuration.

Also, the upright 3504 includes a telescopic pneumatic system 3511, e.g., gas lift, to control height adjustment of the upright 3504.

3.2.17 Seventeenth Alternative Embodiment

Figures 1, 8S:
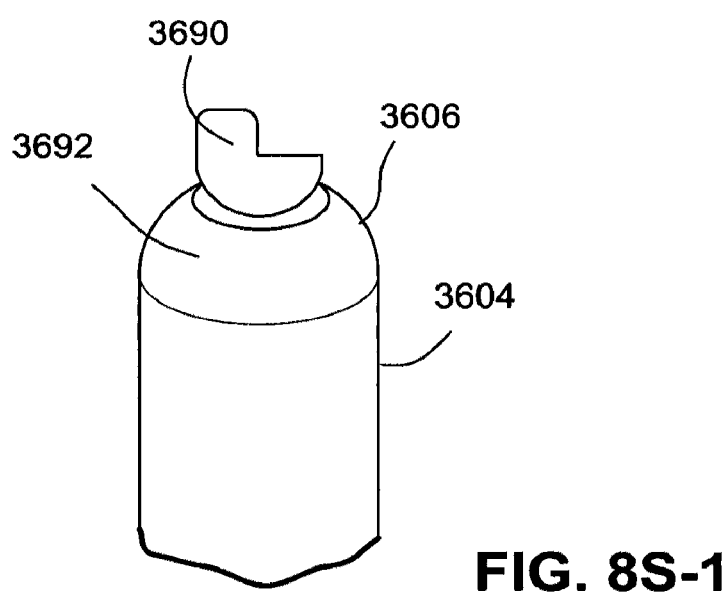

FIG. 8S-1 illustrates an alternative embodiment of a chin support 3606 provided to an upright 3604 of a head support and camera mount assembly. As illustrated, the chin support 3606 includes a ball and socket joint. Specifically, the chin support 3606 includes a first part 3690 with a rounded end that fits into a cup-shape socket of a second part 3692. The first part 3690 provides a chin rest and the second part 3690 is provided to the upright 3604.

3.2.18 Eighteenth Alternative Embodiment

FIGS. 8T-1 to 8T-3 illustrate various views of a head support and camera mount assembly 3700 according to another embodiment of the present invention. As illustrated, the head support and camera mount assembly 3700 includes a base 3702 adapted to clamp onto the side of a table or desktop, an upright 3704 including a chin support 3706, and an arm 3708 that supports an imaging device 3710, e.g., camera.

The arm 3708 is mounted to a pivot joint 3707 that allows the arm 3708 to rotate laterally with respect to the upright 3704, e.g., 90 degrees in both directions. In addition, the pivot joint 3707 includes a hinge region 3709 that allows the arm 3708 to rotate up and down between an in-use configuration and a collapsed configuration. FIG. 8T-3 illustrates alternative embodiments of the pivot joint 3707 and the hinge region 3709 adapted to connect to the arm 3708.

The upright 3704 may include a telescopic arrangement to control height adjustment of the upright 3704.

FIGS. 8T-2 illustrate various sections of the assembly 3700 to show hollow portions for guiding and/or managing cables, e.g., cables associated with the imaging device 3710.

3.2.19 Nineteenth Alternative Embodiment

Figures 1, 8U:
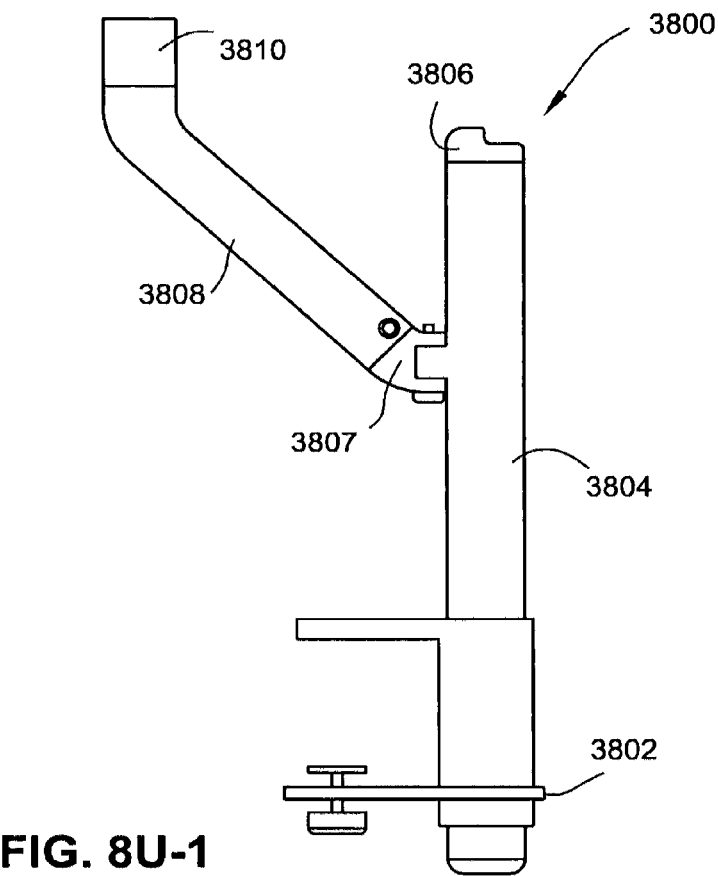
Figures 2, 8U:
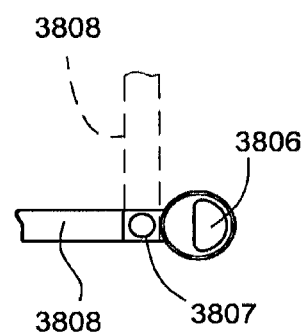
Figures 3, 8U:
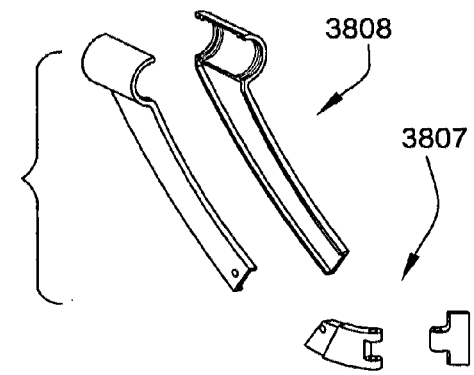
Figures 1, 8V:
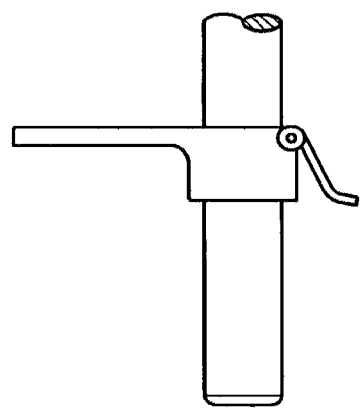
Figures 2, 8V:
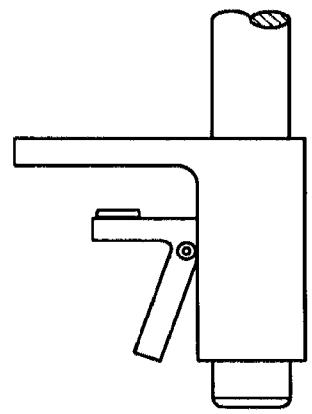
Figures 3, 8V:
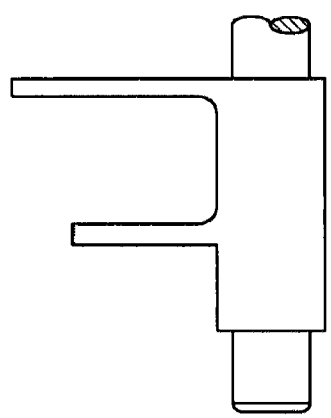
Figures 4, 8V:
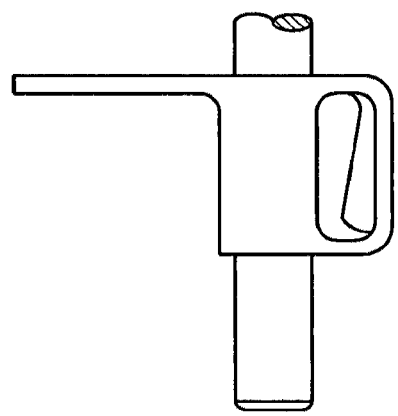
Figures 5, 8V:
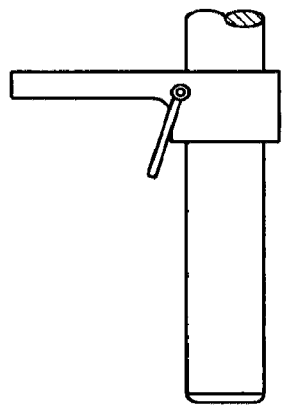
Figures 6, 8V:
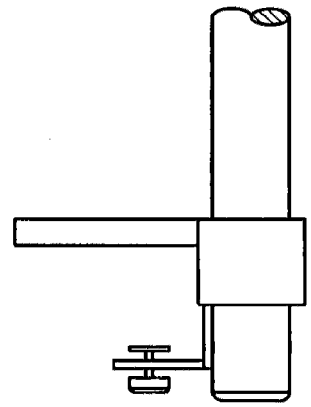
Figures 7, 8V:
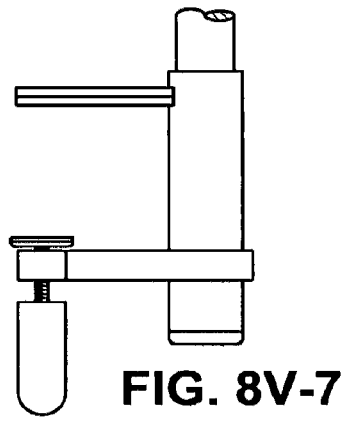
Figures 8, 8V:
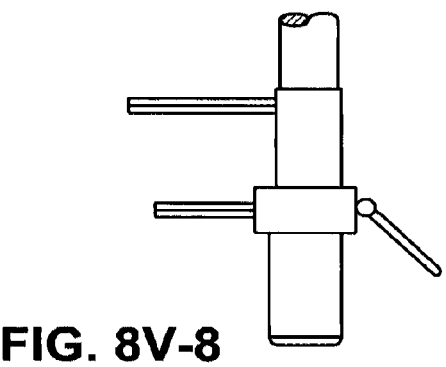
Figures 8, 8V, 9:
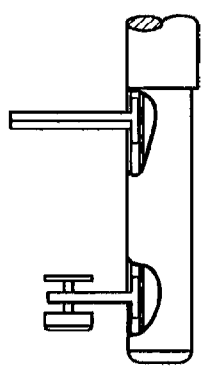
FIGS. 9A-12D schematically illustrate various custom-fit techniques according to embodiments of the present invention.
Figures 8, 8V, 9, 10:
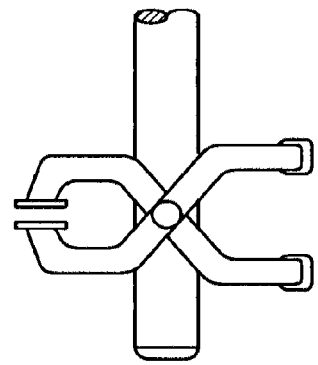

FIGS. 8U-1 to 8U-3 illustrate various views of a head support and camera mount assembly 3800 according to another embodiment of the present invention. As illustrated, the head support and camera mount assembly 3800 includes a base 3802 adapted to clamp onto the side of a table or desktop, an upright 3804 including a chin support 3806, and an arm 3808 that supports an imaging device 3810, e.g., camera.

The arm 3808 is mounted to a hinge 3807 provided to the upright 3904 that allows the arm 3808 to rotate laterally with respect to the upright 3804, e.g., between 3 positions.

3.2.20 Alternative Base Embodiments

FIGS. 8V-1 to 8V-10 illustrate alternative embodiments of a base adapted to clamp a head support and camera mount assembly onto the side of a table or desktop. For example, the base may include a G-clamp such as that shown in FIGS. 8V-6 or 8V-7, a cam arrangement such as that shown in FIGS. 8V-1, 8V-5, or 8V-8, a slide arrangement such as that shown in FIG. 8V-9, or a pivot arrangement such as that shown in FIGS. 8V-2 or 8V-10.

3.2.21 Alternative Upright Embodiments for Height Adjustment

Figures 6, 8W:
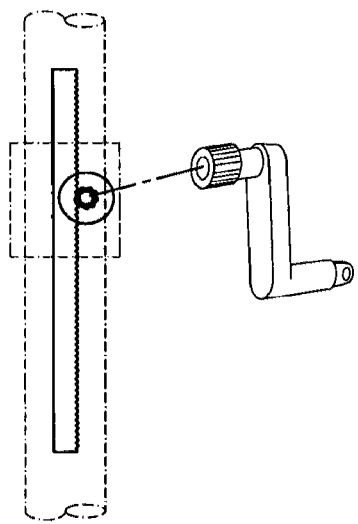
Figures 7, 8W:
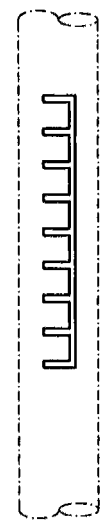
Figures 8, 8W:
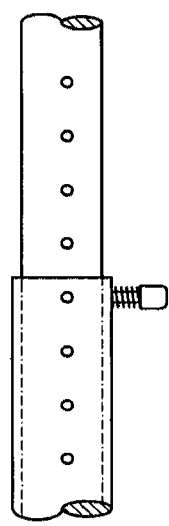
Figures 8, 8W, 9:
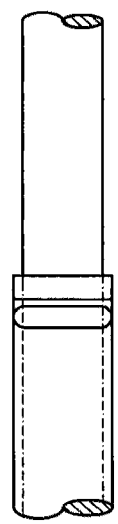

FIGS. 8W-1 to 8W-9 illustrate alternative embodiments of an upright for a head support and camera mount assembly that allows height adjustment. For example, the upright may include a counterweight arrangement as shown in FIG. 8W-1, a pneumatic system, e.g., gas lift, as shown in FIG. 8W-2, a telescopic arrangement with a threaded knob lock as shown in FIG. 8W-3, a telescopic arrangement with a cam lock as shown in FIG. 8W-4, a telescopic arrangement with a collar lock as shown in FIG. 8W-S, a rack and pinion arrangement as shown in FIG. 8W-6, incremental slot arrangement as shown in FIG. 8W-7, a telescopic arrangement with a spring-loaded pin lock as shown in FIG. 8W-8, or a telescopic arrangement with an expanding lock as shown in FIG. 8W-9.

3.2.22 Bushing Embodiment

FIG. 8X illustrates an embodiment of a bushing 3995 for use with an upright having a telescopic arrangement. As illustrated, the bushing 3995 is positioned to prevent the patient from squashing his/her finger between first and second telescoping parts 3950, 3952.

3.2.23 Assembly Support Embodiment

FIGS. 8Y-1 to 8Y-2 illustrate a support 4001 that may be used in lieu of the clamp-type bases described above to support a head support and camera mount assembly on the table or ground. For example, the support 4001 may be adapted to connect to the upright of the assembly.

4. Custom Mask Fitting

With the above system, the selection of a mask system can be very rapid. Moreover, with a wider range of mask systems, a better fit can be obtained for each patient, even those with unusual facial shapes.

The system is also advantageous in that new mask systems can be entered into the mask system database 2. This is advantageous as each patient or clinician is not required to learn or even know about each new mask, and which patients to which the new mask system is particularly suited.

This will allow clinicians to concentrate on person-to-person interactions and medical treatment, rather than struggling with measurement of the patient's dimensions, etc. The ability of the physician or clinician to introduce and recommend new products would entail better care of the patients. Moreover, patients who are fitted with the best possible mask system are more likely to use such mask system, which increases patient compliance and effectiveness of treatment.

In some applications, scaling may be required so that the dimensions are accurately entered into the system. Scaling can be achieved, for example, by a patient holding a ruler or other calibration device in the image when the frontal and/or profile views are taken. For example, the head supporting template could be provided with a built in calibration or scaling device, easily visible by the reader, e.g., scanner, camera, etc. The system can then process the image, in part by taking into account the information provided by the scaling device, e.g., a ruler or standard length. In another form, scaling can be achieved by utilizing the known focal length and/or field of view of the camera, or by clicking on a standard length scale (e.g., a ruler).

In another embodiment, the relevant dimensions of the patient's head can be automatically processed by the system, without the need for the clinician or patient to "click" on the points described above in relation to FIGS. 6-7B. In this system, the clinician or patient need only know how to operate a reader or an imaging device such as a webcam or digital camera. For example, the detection of facial features can be obtained using algorithms that typically use neural networks. "See Storm" offers a package that detects features in the frontal image, which package is commercially available. Also, major airport security systems employ facial recognition systems/software which may automatically analyze and output desired fit dimensions, without user needing to click dimensions, thereby eliminating steps in the imaging process.

In yet another alternative, a three-dimensional modeling technique is used to determine the mask that will best fit the patient. The system would use a three-dimensional requisition device to capture a 3D model of the patient's face. The model of the mask system is then "placed" against the model of the patient, electronically speaking, and a best fit is determined based on the minimized gap between the mask and the patient.

In yet another alterative, the 3D modeling technique may also take into account skin texture and firmness. Once a mask fit is found, e.g., based on the above 3D model technique for determining mask systems with minimized gap(s) between the mask system and the patient, the software will then perform an analysis for leaks and pressure at certain points around the cushion to determine the mask size that will provide maximum comfort. Fully automated facial scanners are commercially available from Cyberware. In addition, hand-held three-dimensional laser scanning devices are also commercially available. In general, both contact and non-contact imaging systems are contemplated. An example of a contact system is a multitude of pins that are slidable on a base, and which can take the impression of a patient's features.

5. Custom Mask Fitting—Partial Fits and/or Custom Component Selection

Although the above techniques include the selection of an entire mask system, similar principals can be used to select only components thereof, such as headgear, mask cushions, etc. Moreover, such information can be used to select an off-the-shelf mask system, as well as create a custom made patient interface (e.g., cushion) to replace the standard cushion provided with the mask system. Several methods for creating customized masks are described below.

5.1 Method 1: Contact Cushion Contouring (Stylus Recording)

A patient's face deforms when it is subjected to a load. For a mask to achieve the best sealing performance the contour of the mask should match the surface that it is sealing against. To develop a customized mask for a patient the shape of the mask should match the contour of the comfortable facial deformation of the patient.

Figure 9A:
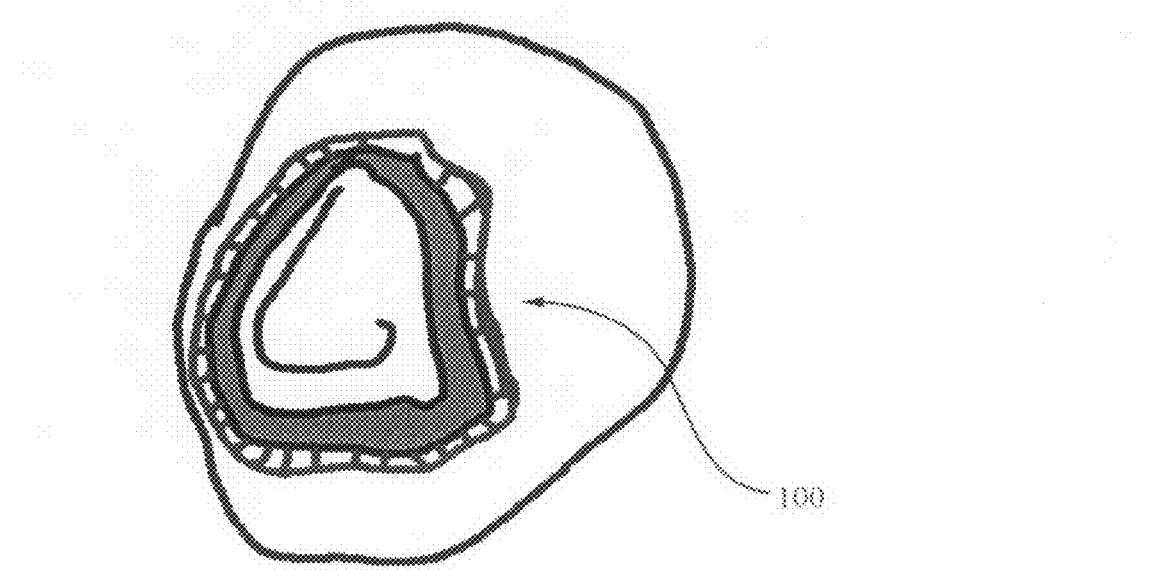
Figure 9B:
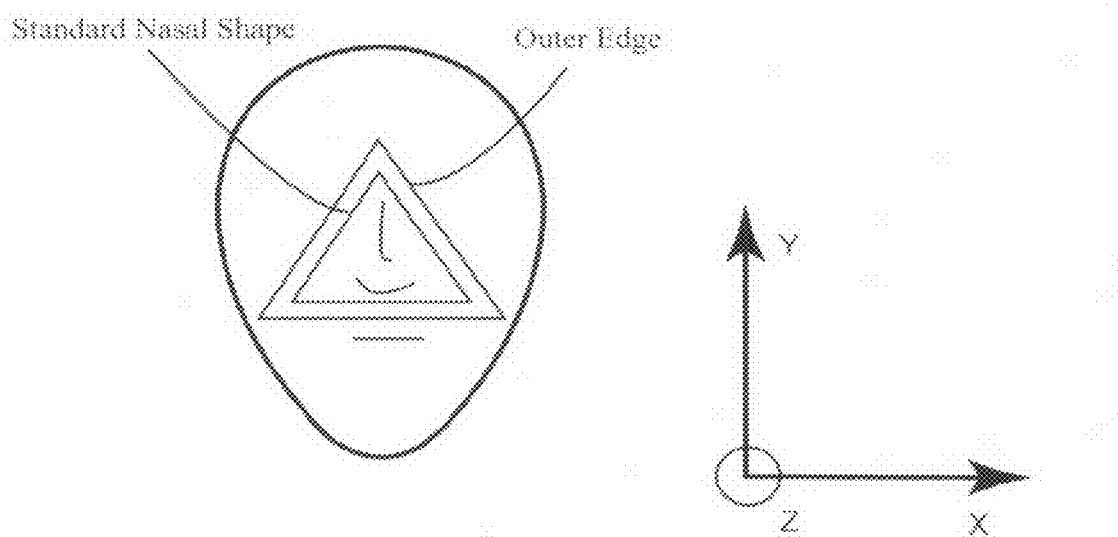

In order to find the comfortable facial deformation of the patient, a standard nasal or full face mask cushion outline can be applied. As shown in FIG. 9B, this outline is constrained in the x-y directions according to the standard cushion profiles, however, it is variable in the z direction.

Figure 10:
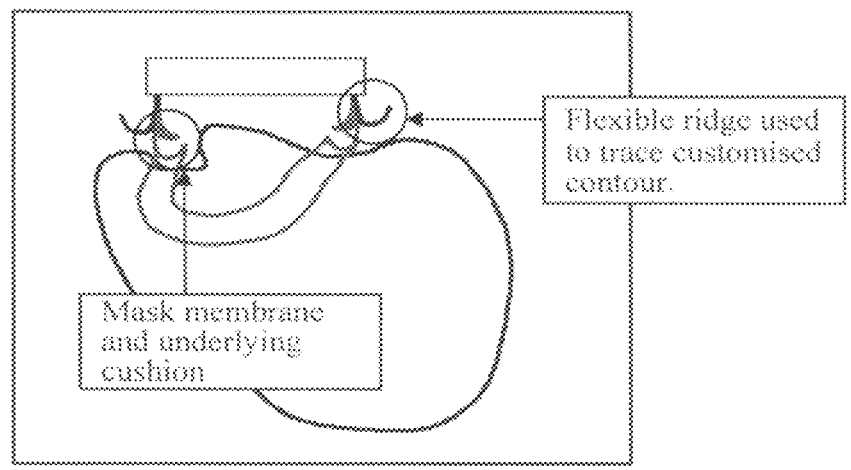
Figure 10A:
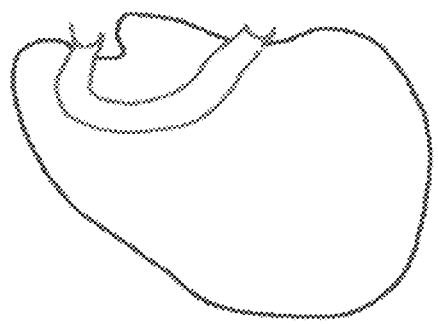
Figure 10B:
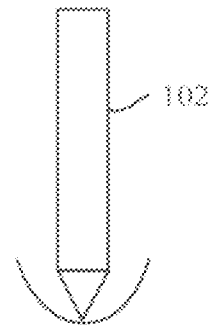
Figure 10C:
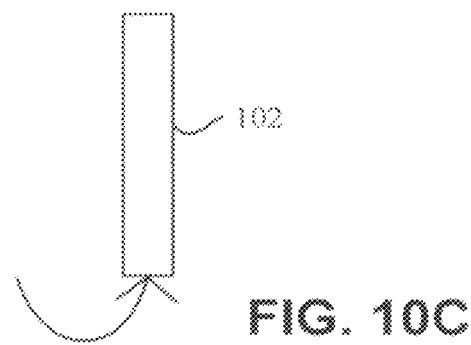

When subjected to a set pressure the outline deforms in the z direction according to the facial elasticity of each individual patient. This pressure should be equal to or exceed that required for sealing and not exceed that which is comfortable for a patient. The pressure can be produced either by a cushion or by point loads, which are controlled either by mass or a spring constant. FIGS. 9A, 10 and 10A show a mask membrane 100 and underlying cushion applied to a face. Using this outline, the stylus 102 can then be run over either the valley of the cushion (FIG. 10) or the ridge (FIG. 10C) in order to capture the variation in the z direction data.

A further embodiment using a cushion utilizes a deformable material that changes shape when pressure is applied. The material is fitted to a standard mask frame and again has x-y dimensions matching that of standard nasal or full-face mask cushions. The frame and cushion is applied to the face at which point the deformable material varies in the z direction according to the facial elasticity of the patient. Once the frame is removed from the face, the z contour can be traced by a stylus or otherwise captured using scanning or other data capturing methods. Suitable materials include but are not limited to gel, silicone, foam or other plastic materials.

Figure 11A:
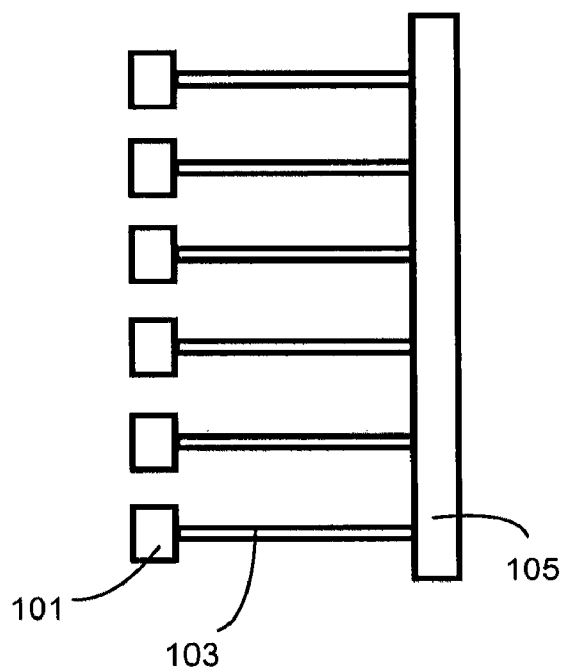

An alternative embodiment using point loads is shown in FIG. 11A. This includes a series of point loads (masses) 101 of which are mounted on rods 103 according to the preferred mask cushion outline in the directions x-y. Rods 103 are slidable on a frame 105. When fully extended as shown in FIG. 11A, the point loads have a uniform displacement in z.

Figure 11B:
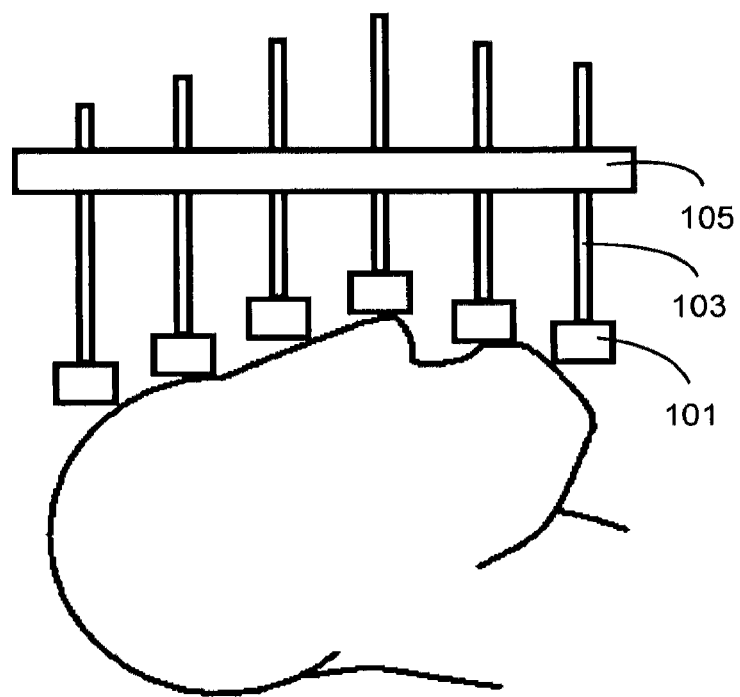

In order to apply the mass loads uniformly (due to gravity), the patient should lie on his or her back. While this may lead to some additional set-up effort, it simulates the real-life bed situation and allows for the relaxation of muscle tissue with gravity. Once the patient is comfortable, the support is moved towards the patient until all masses are resting on the patient's face, see FIG. 11B. The patient's contour can now be traced from the protruding rods using a stylus, photographic means, scanning or other data capturing methods.

Figure 11C:
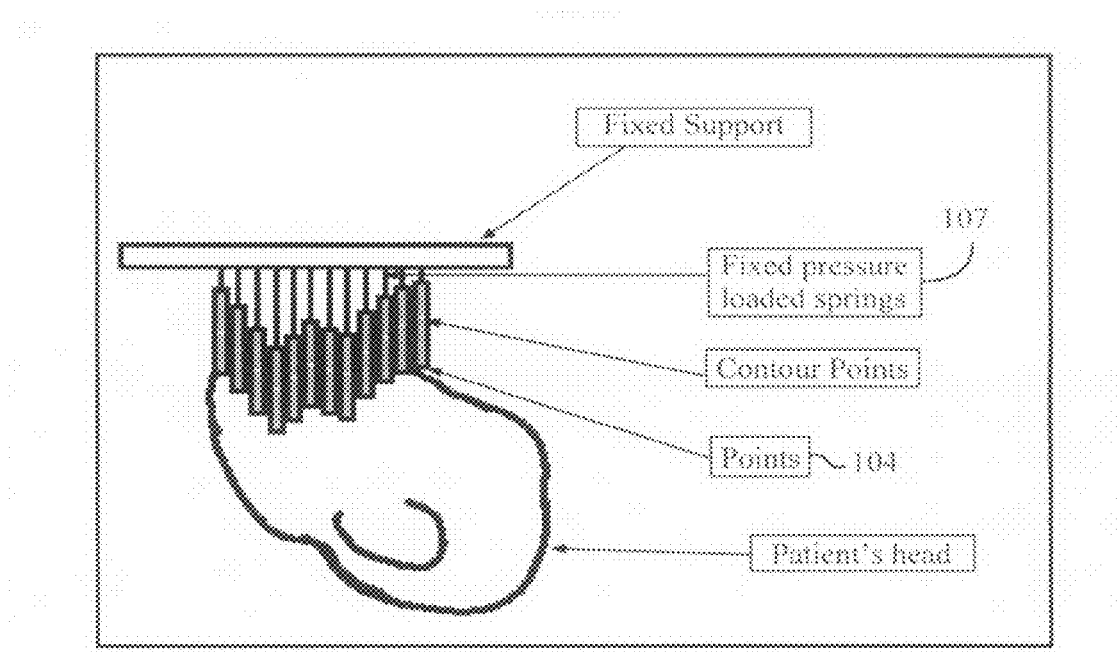

A further embodiment of the system can be set up using pre-loaded springs or a measurement of central contour points, see FIG. 11C. Such a method would not rely on the patient lying down.

An advantage of the above described systems is that they can be used on numerous patients, with only the data being sent to the mask fitting system or mask manufacturing base for conversion into a custom mask. Note, these systems as described relate only to changes in the z direction, however, similar systems can be utilized to capture data in the x and y directions providing a full knowledge of the patient geometry or completely customized cushions.

Figure 11D:
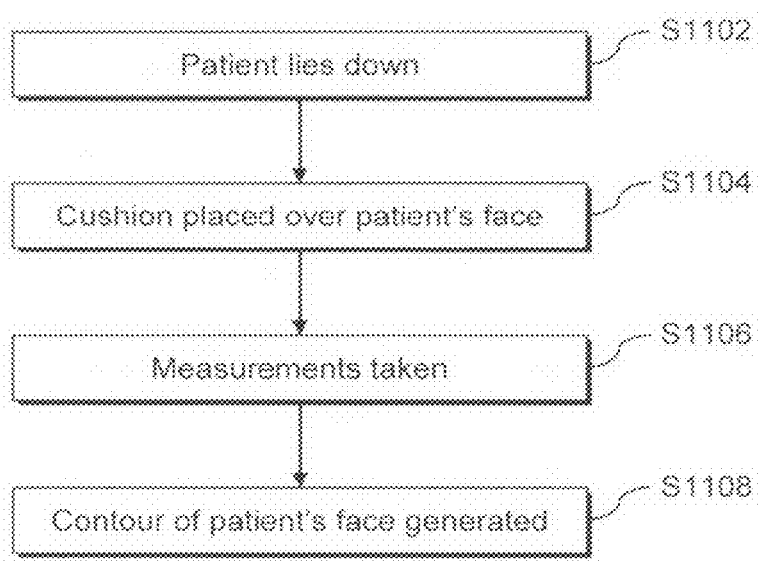

Specifically, in certain example embodiments, a cushion of translatable pins may be used for 3D modeling and to determine facial make-up. Such systems may function similarly to those described above, though they may record data with respect to x, y, and z coordinates to generate a 3D contour of the patient's face. FIG. 11D is a flowchart of an example process for generating a 3D model of a patient's face using a cushion of translatable pins. As noted above, it is advantageous for a patient to lie down to apply the mass loads from the pins uniformly. Accordingly, in step S1102, the patient lies down. A cushion is placed over the patient's face in step S1104.

Measurements are taken in step S1106. Measurements may be taken by using a system akin to that shown in FIG. 11B. As such, point loads 101 would come into contact with the patient's face. Rods 103 may be operably connected to controller 24, which may generate a contour of the patient face (as in step S1108). The contour may be generated by measuring, for example, the depths of rods 103 relative to frame 105, associating the x-y position of each rod to a depth relative to frame 105 (or some other plane), etc. It will be appreciated that the cushion of pins may take measurements of the patient's face from frontal and/or profile views. As noted above, it is preferable to have the patient lying down. However, any angles can be used to generate the contour of the patient's face if mathematical transforms are applied to the captured data. In some cases, additional data may need to be extrapolated to complete the contour if the positioning of the cushion is greatly askew. This can be corrected, for example, by assuming some level of symmetry and completing the contour accordingly.

It will be appreciated that the resolution of the contour of the patient's face may be influenced by, for example, the number of pins in the cushion. Generally, more pins in the cushion will translate to a higher resolution. It also will be appreciated that data relating to the contour of the patient's face may be interpolated from a coarse measurement. Taking a coarse measurement may provide sufficient data, as an exact topography may not be necessary in all cases. Furthermore, it may be advantageous to have a higher resolution and/or concentration of pins in certain areas that are particularly sensitive (e.g. nose and mouth) while such a high resolution is not necessary at other locations (e.g. forehead). Thus, using these methods, it may be possible to use a cushion of translatable pins as a subcutaneous scanning technique to determine facial make-up and generate a corresponding 3D model. A mask suited for the patient may be recommended based on this information, and the contour and/or the recommended mask may be displayed.

5.2 Method 2: Nasal Cannular Scan

Figure 12A:
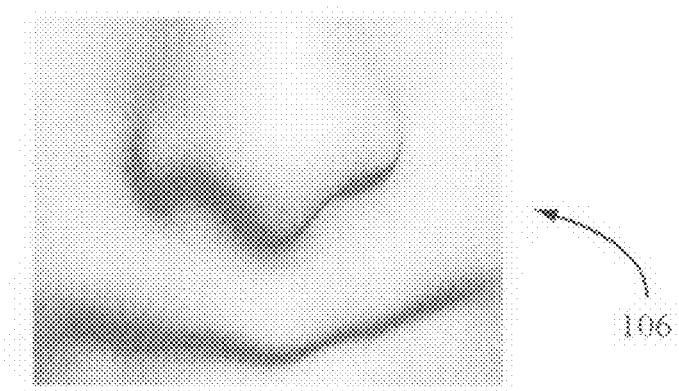
Figure 12B:
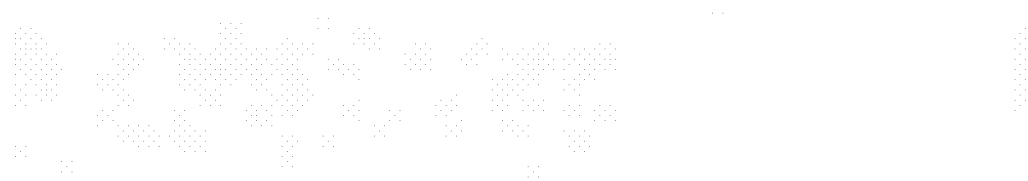
Figure 12B:
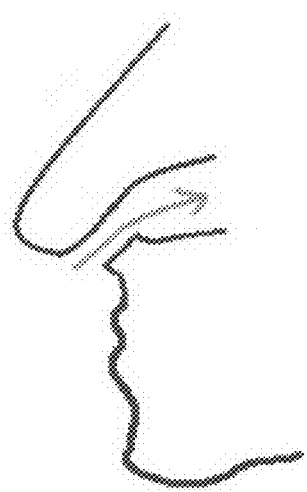

The patient's nasal area is scanned or traced with the laser/stylus and the resulting contour 106 (FIG. 12A) is used to develop customized nasal prongs. The direction of the prongs is also modified so that the airflow is placed in a direction that flows in alignment with the start of the nasal passage. FIG. 12B is a laser image of a patient's nose, e.g., the nares.

Figure 12C:
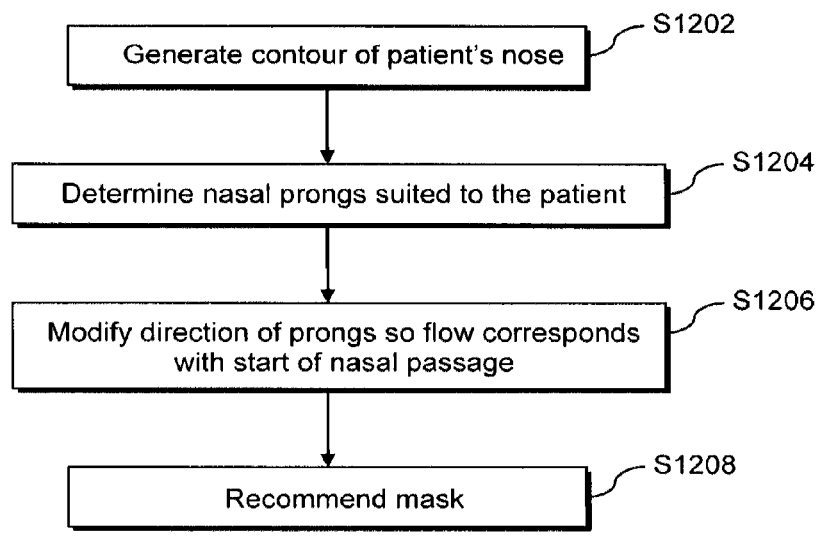

A mask suited for the patient may be recommended based on this information, according to the example process shown in FIG. 12C. In FIG. 12C, a contour of the patient's nose is generated. It may be generated, for example, by scanning the nasal area with a laser, tracing it with a stylus, etc. It will be appreciated that any sensor capable of generating a signal (preferably digital) corresponding to the contour of the nasal area may be used. It also will be appreciated that areas beyond the mere nasal area may be sensed. Nasal prongs suited for the patient are determined in step S1204. Then, in step S1206, the direction of the prongs may be modified so that the flow of air corresponds with the start of the nasal passage. Based at least on all of this information, a mask may be recommended to the patient in step S1208. The contour and/or the recommended mask also may be displayed

5.3 Method 3: Shadow Stereopsis Sensor

It also may be possible to use a shadow stereopsis sensor as a subcutaneous scanning technique to determine facial make-up and to generate a corresponding 3D model of a patient's face. In general, stereopsis is a process in visual perception leading to perception of the depth or distance of objects. An object's shadow may provide information relating to spatial relationships and depth. Specifically, shadows caused by one object are a source of information for spatial position, location, and depth relations. For example, the gap between an object and its shadow may indicate the object's height relative to a plane, and the location of a shadow on the plane may be indicative of the object's distance and location.

Figure 12D:
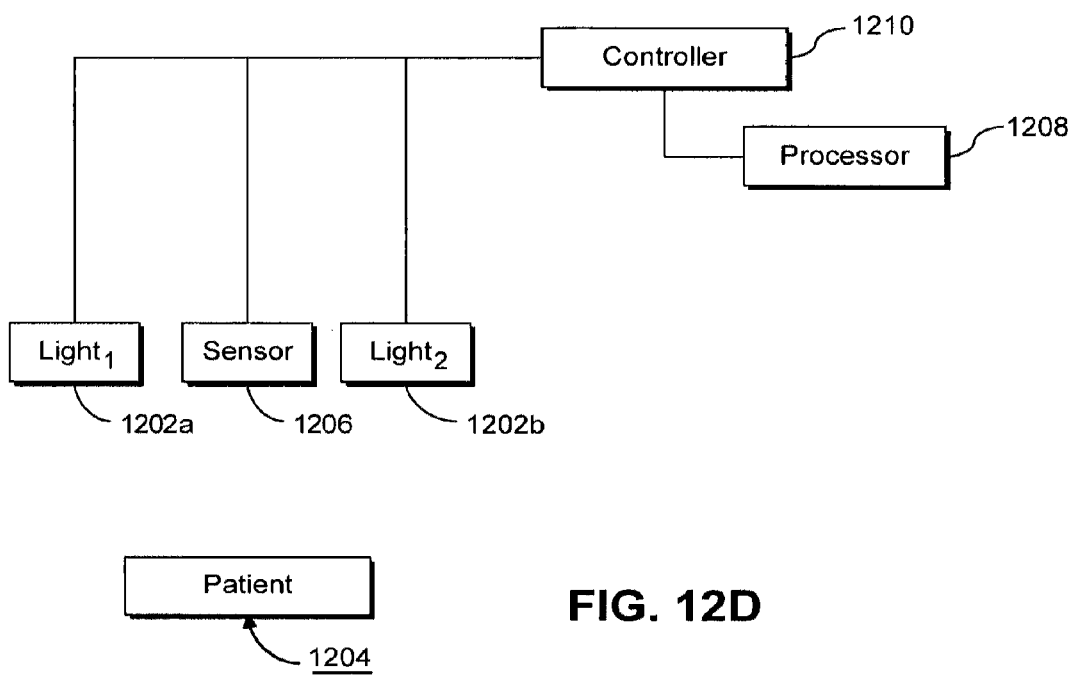
Figure 13:
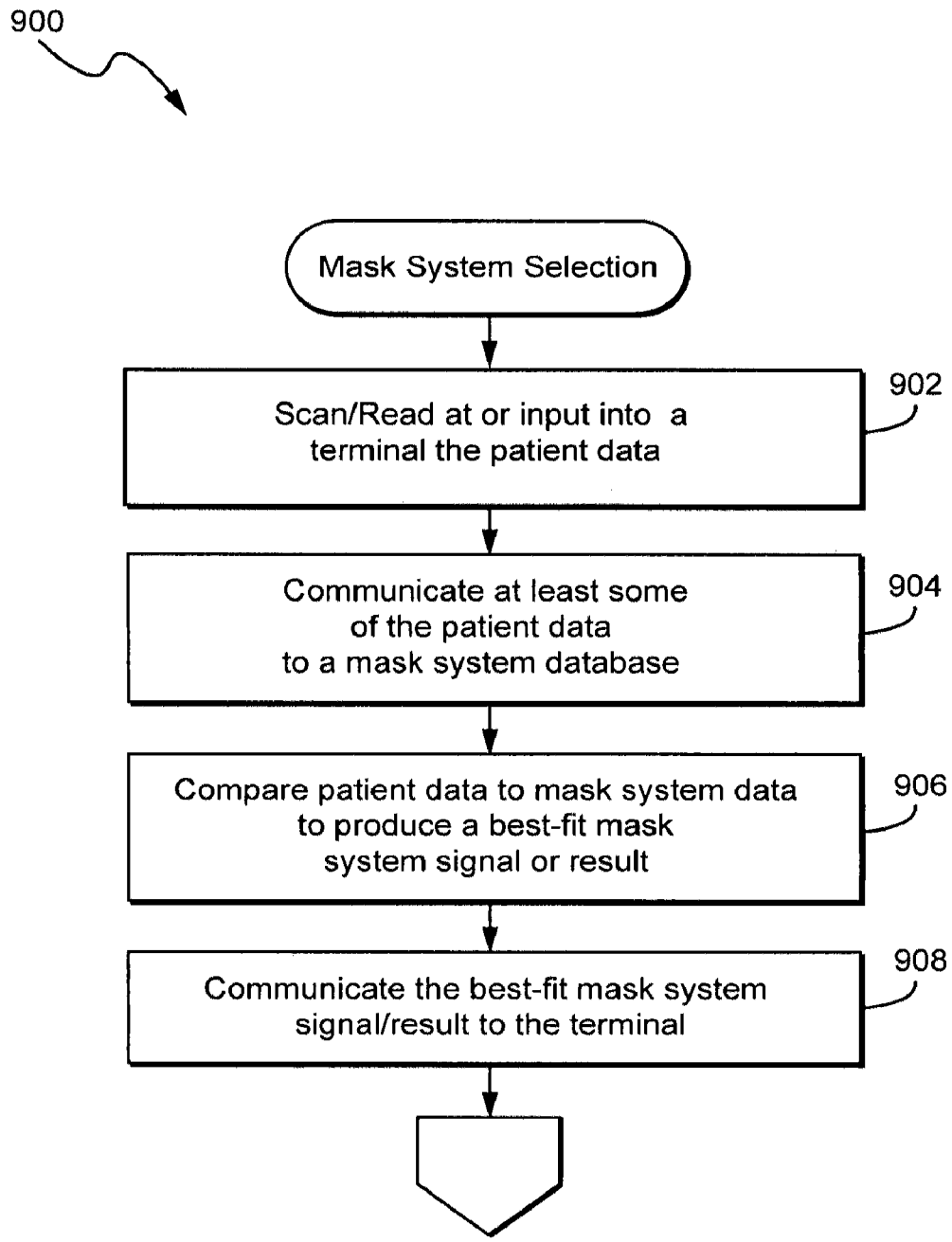
FIG. 13 is a flowchart of a mask system selection process according to an embodiment of the present invention.
Figure 14:
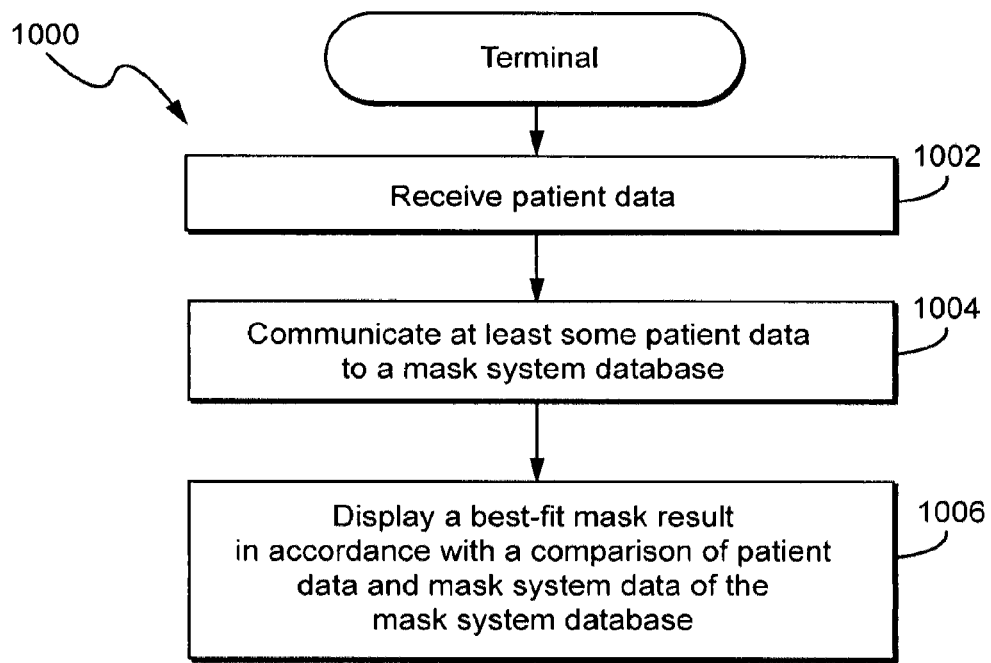
FIG. 14 is a flowchart of a terminal process according to an embodiment of the present invention.
Figure 15:
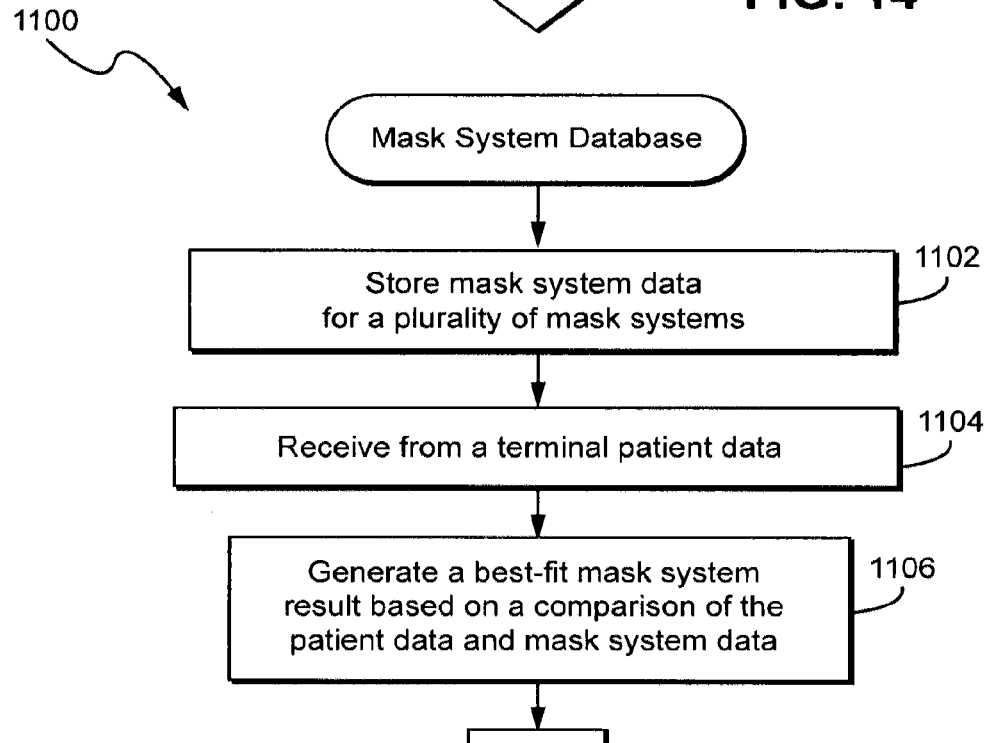
FIG. 15 is a flowchart illustrating a mask system database process according to an embodiment of the present invention.
Figure 16:
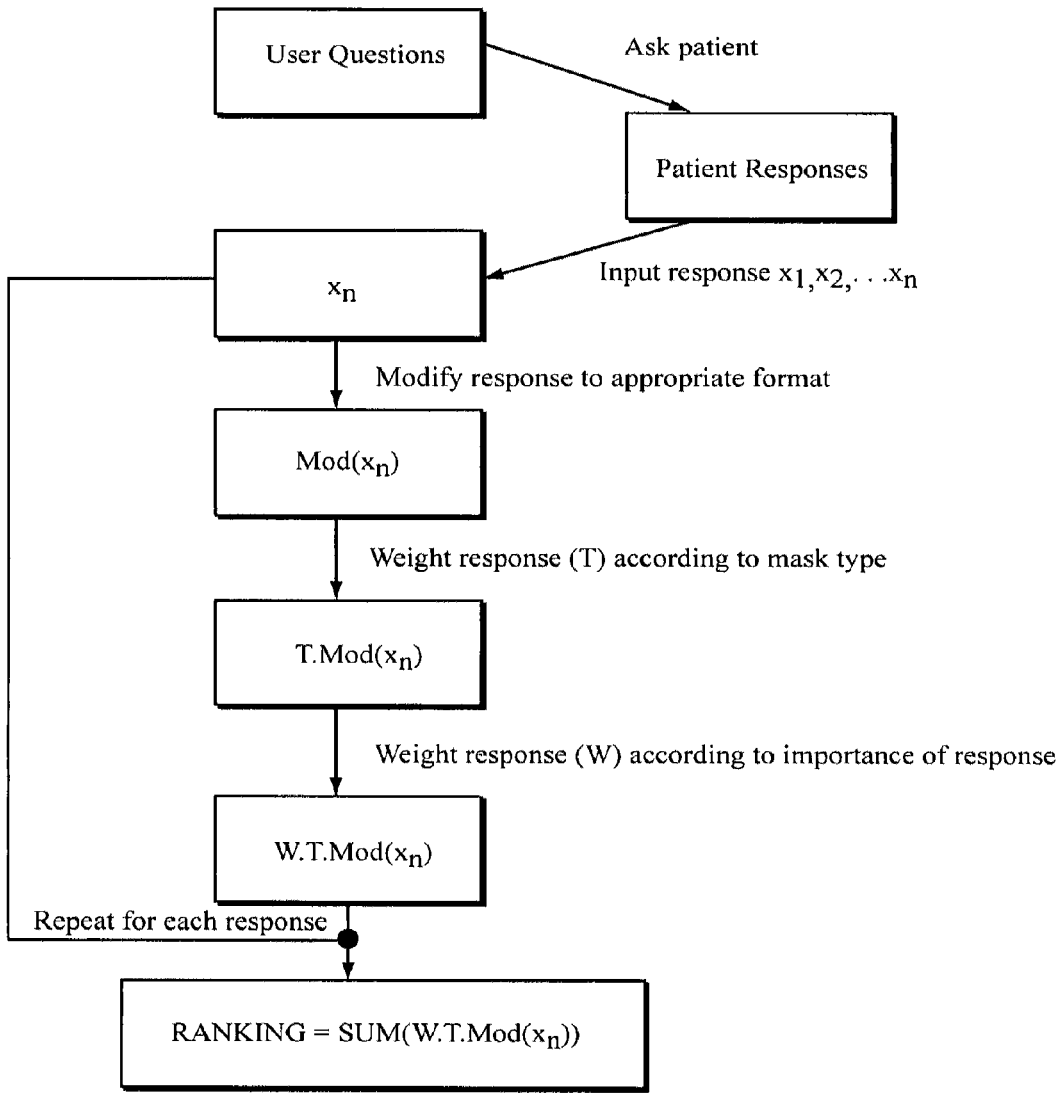
FIG. 16 is a flow chart illustrating a mask selection algorithm according to an embodiment of the present invention.
Figure 17:
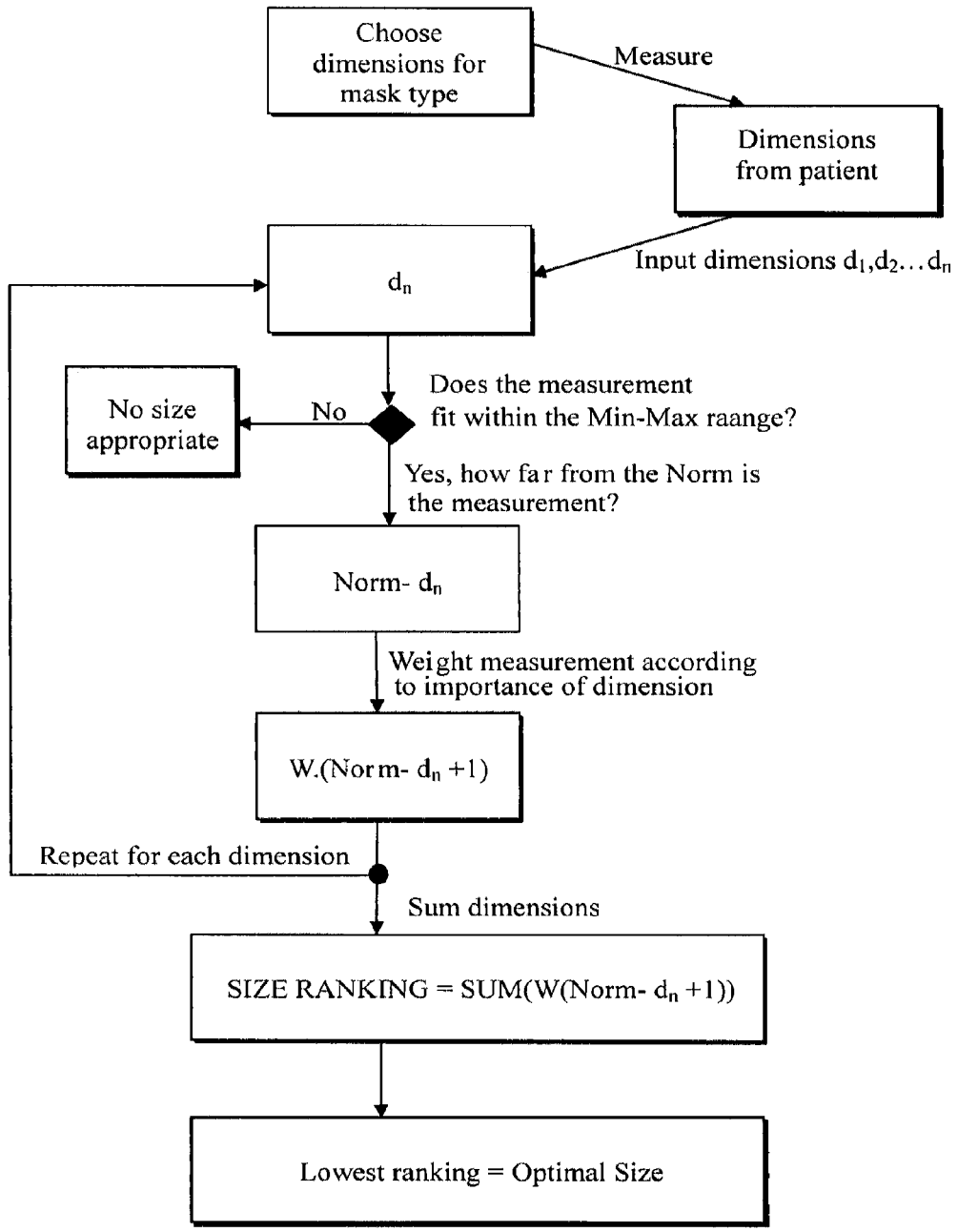
FIG. 17 is a flow chart illustrating a mask fitting algorithm according to an embodiment of the present invention.

Thus, a shadow stereopsis sensor may be used to develop a 3D map of a patient's face using, for example, the illustrative system shown in FIG. 12D. One preferred embodiment uses two spaced apart light sources 1202a-b. These light sources 1202a-b create shadows on the patient's face 1204, which may be detected by a sensor 1206. A processor 1208 may interpret the data (e.g. presence/absence of shadow, shade of shadow, etc.) from a sensor and generate a 3D map from the sensor's data. A controller 1210 may coordinate the shining of light, sensing, and processing steps. A mask suited for the patient may be recommended based on this information, and the contour and/or the recommended mask may be displayed.

6. Example Mask Selection Processes and Algorithms

FIG. 13 illustrates a process 900 for mask system selection according to an embodiment of the present invention. In step 902, patient data is scanned or read at a terminal. Alternatively, the patient data can be simply input into the terminal. In step 904, at least a portion of the patient data is communicated to a mask system database. In step 906, mask system data is compared to patient data to produce a best-fit mask system signal or result. In step 908, the best-fit mask system signal/result is communicated to the terminal.

FIG. 14 illustrates a process 1000 for operation of terminal 6. In step 1002, patient data is received into the terminal. In step 1004, at least a portion of the patent data is communicated to a mask system database. In step 1006, a best-fit mask result is displayed at the terminal in accordance with a comparison of patient data and mask system data of the mask system database.

FIG. 15 illustrates a process 1100 for operating a mask system database. In step 1102, mask system data is stored for a plurality of mask systems. In step 1104, patient data is received from a terminal. In step 1106, a best-fit mask system result or signal is generated based on a comparison of the patient data and mask system data.

FIGS. 16 and 17 are sample flowcharts. FIG. 16 is based on mask type while FIG. 17 is based on mask size. FIGS. 16 and 17 show the process of how clinician input and designer input are captured in a sample method of weighting of the questions, and a sample method of weighting of the dimensions, respectively. The weighting of dimensions provides data for analytically describing 'goodness of fit.' Stated differently, the way in which data is produced conveniently provides the designer's expertise to the possibly inexperienced clinician fitting the mask. This may provide one or more of the following improvements to the known processes, such as fitting templates, descriptions in the user manual, etc.

Improved consistency of fit
Reduced fitting time
Reduced requirement of trial and error
Reduced reliance on clinician training
Direct incorporation of designers knowledge to the fitting method.

The flowcharts of FIGS. 13-17, or portions thereof, can be programmed onto a machine-readable recording medium, e.g., a compact or floppy disk, memory etc., that includes a control program for controlling a data processor, e.g., controllers 14 (FIG. 2) or 24 (FIG. 3). Moreover, upgrades at terminal 6 may be initiated by sending such recording medium to the terminals. Alternatively, or in addition, upgrades to the control program can be sent electronically to the terminals.

As shown in FIG. 1, the mask fitting system 1 is preferably implemented on a programmed general purpose computer. A processor associated with such a general purpose computer may be operable to generate and interpret signals from sensors, imaging devices, or the like; perform mathematical operations; control a computerized questionnaire; look up data from a database; generate a display; etc. It will be appreciated that the term processor is used in a generic sense, and any control mechanism comprising any combination of hardware, software, firmware, or the like may be used. It also will be appreciated that such a processor may be operable with any of the techniques for mask fitting described herein (e.g. picture and/or video imaging, contact cushion contouring, nasal cannular scans, shadow stereopsis sensors, combinations thereof, etc.). The mask fitting system (or its subcomponents) can also be implemented on a special purpose computer, a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA or PAL, or the like. In general, any device, capable of implementing a finite state machine that is in turn capable of implementing the described systems, methods and the flowcharts shown in FIGS. 13-17, can be used to implement the mask fitting system.

In an embodiment, the mask fitting system may be automated (e.g., by servo motors) so that so that the whole process or parts of the process may be automated. The mask fitting system may be "plug and play" and both the mechanical components and software may do the job for the clinician or provide recommendations for review by the clinician.

A mask fitting algorithm is provided on-line. See the "CPAP Mask Sizing Guide" from the cpap.com website.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in nonmedical applications.

What is claimed is:

1. A mask fitting system for selecting, from a plurality of selection mask systems, at least two mask systems for a patient, comprising:
   an image and/or video acquiring device operable to capture plural images and/or a video of at least a portion of the patient's face;
   a processor operable to process the images and/or video to determine a physical characteristic of the patient's face based at least on the images and/or video and at least one symbol, the at least one symbol having been applied to the patient's face prior to the image and/or video acquiring device capturing the images and/or video;
   a display to show the images and/or video and/or each of the selection mask systems;
   a head support and camera mount assembly including:
     a base;
     an upright provided to the base, the upright including a chin support adapted to support the patient's chin in use; and
     an arm extending outwardly from the upright, the arm having a distal end structured to support the image and/or video acquiring device, the image and/or video acquiring device being configured to capture at least one image of the patient's face when the patient's chin is resting on the chin support in use; and
   servo motors to automate movement of the arm,
   wherein the processor is further operable to select the at least two mask systems based at least in part on the physical characteristic of the patient's face, and
   wherein the processor is further operable to generate scheduling information, the scheduling information suggesting when the patient should rotate among the two or more mask systems.

2. The system of claim 1, wherein the image and/or video acquiring device is a digital camera and/or web cam.

3. The system of claim 1, wherein the at least one symbol comprises a sticker.

4. The system of claim 1, wherein the at least one symbol is located on at least one predetermined position on the patient's face, the at least one predetermined position corresponding to one or more of the patient's nostrils' sidewalls, the patient's nose's bottom tip; the patient's nasal bridge, the patient's middle of forehead, and the patient's chin.

5. The system of claim 1, wherein the base is adapted to clamp onto the side of a table or desktop.

6. The system of claim 1, wherein the arm is laterally rotatable with respect to the upright.

7. The system of claim 1, wherein the arm is rotatable up and down with respect to the upright between an in-use configuration and a collapsed configuration.

8. The system of claim 1, wherein the arm is slidable up and down with respect to the upright.

9. The system of claim 1, wherein the image and/or video acquiring device is movably mounted to the arm.

10. The system of claim 1, wherein the base, upright, chin support, and/or arm is constructed of steel, plastic, and/or aluminum.

11. The system of claim 1, wherein the at least two mask systems are selected from a plurality of either nose masks or full face masks.

12. The system of claim 1, further comprising a shadow steropsis sensor configured to generate a signal corresponding to shadow caused by light shined on the patient's face, the signal being indicative of a contour of at least a portion of the patient's face.

13. The system of claim 1, wherein the arm is telescoping and lockable in in-use extended and out-of-use collapsed configurations.

14. The system of claim 1, wherein the at least one image and/or video includes a portion of the patient's face comprising at least the patient's nasal area, and
   wherein the processor is further operable to (a) generate a contour of at least the patient's nasal area, and (b) determine a type and direction of nasal prongs suited to the patient based at least in part on the contour.

15. The system of claim 14, wherein the at least two mask systems are selected based at least in part on the type and direction of nasal prongs suited to the patient.

16. The system of claim 1, further comprising a routine operable to allow a user of the system to overlay at least one image of at least one mask system and the at least one image and/or video.

17. The system of claim 16, wherein the routine is further operable to synchronize a plurality of images and/or videos from a plurality of image and/or video acquiring devices.

18. The system of claim 1, wherein the at least one processor is further configured to use the at least one symbol to gauge distance of and/or orientation of the patient's face, based on fixed dimensions of the at least one symbol.

19. The system of claim 18, wherein the at least one processor is further configured to use the at least one symbol to obtain a measurement of the patient's face.

20. The system of claim 1, wherein the arm is laterally rotatable through approximately 90 degrees in both directions from center in order to position image and/or video acquiring device at locations suitable for acquiring side photos of the patient's face.

21. The system of claim 20, wherein the camera mount assembly includes a button to allow rotation of the arm, the button being detented in at least three positions corresponding to straight ahead, right side, and left side locations for the image and/or video acquiring device, relative to the patient's face.

22. The system of claim 20, further comprising servo motors to automate movement of the arm.

23. The system of claim 1, wherein the arm is rotatable.

24. The system of claim 23, further comprising a squeeze button at a hinge region between the arm and the upright adapted to allow rotation of the arm when squeezed and to prevent rotation not squeezed.

25. The system of claim 23, wherein the hinge is dampened to prevent the arm from banging against the upright if dropped.

26. The system of claim 1, wherein the upright includes a telescopic arrangement to control height adjustment of the upright.

27. The system of claim 26, wherein telescopic movement of the upright is controlled by a pneumatic system.

28. The system of claim 26, wherein the telescopic arrangement includes a bushing positioned to prevent the patient from squashing his/her finger between telescoping parts.

29. The system of claim 26, wherein the telescopic arrangement is raisable by 10% to 500% of its height.

30. The system of claim 26, wherein the telescopic arrangement is raisable by 150 mm.

31. A method of selecting, from a plurality of selection mask systems, at least two mask systems for a patient, the method comprising:
    applying at least one symbol to the patient's face;
    capturing at least one image and/or video of at least a portion of the patient's face; and
    determining a physical characteristic of the patient's face based at least in part on the at least one image and/or video and the at least one symbol;
    displaying the at least one image and/or video and/or the selection mask systems;
    selecting the at least two mask systems based at least in part on the physical characteristic of the patient's face: and
    generating a report that suggests when the patient should rotate among the selected at least two mask systems,
    wherein the capturing is practiced after the patient engages with a head support and camera mount assembly including:
        a base;
        an upright provided to the base, the upright including a chin support adapted to support the patient's chin in use; and
        an arm extending outwardly from the upright, the arm having a distal end structured to support the image and/or video acquiring device, the image and/or video acquiring device being configured to capture at least one image of the patient's face when the patient's chin is resting on the chin support in use, and
    wherein said capturing is practiced by laterally rotating the arm through approximately 90 degrees in both directions from center in order to position image and/or video acquiring device at locations suitable for acquiring front and side photos of the patient's face.

32. The method of claim 31, wherein the at least one image and/or video is acquired by a digital camera and/or web cam.

33. The method of claim 31, wherein the at least one symbol comprises a sticker.

34. The method of claim 31, wherein the at least one symbol is applied at least one predetermined position on the patient's face, the at least one predetermined position corresponding to one or more of the patient's nostrils' sidewalls, the patient's nose's bottom tip; the patient's nasal bridge, the patient's middle of forehead, and the patient's chin.

35. The method of claim 31, wherein the at least one image and/or video includes a portion of the patient's face comprising at least the patient's nasal area, and further comprising:
    generating a contour of at least the patient's nasal area;
    determining a type and direction of nasal prongs suited to the patient based at least in part on the contour.

36. The method of claim 31, wherein the at least two mask systems are selected based at least in part on the type and direction of nasal prongs suited to the patient.

37. The method of claim 31, wherein the base is adapted to clamp onto the side of a table or desktop.

38. The method of claim 31, wherein the arm is laterally rotatable with respect to the upright.

39. The method of claim 31, wherein the arm is rotatable up and down with respect to the upright between an in-use configuration and a collapsed configuration.

40. The method of claim 31, wherein the arm is slidable up and down with respect to the upright.

41. The method of claim 31, wherein the image and/or video acquiring device is movably mounted to the arm.

42. The method of claim 31, wherein the base, upright, chin support, and/or arm is constructed of steel, plastic, and/or aluminum.

43. The method of claim 31, wherein the at least two mask systems are selected from a plurality of either nose masks or full face masks.

44. The method of claim 31, wherein the camera mount assembly includes a button to allow rotation of the arm, the button being detented in at least three positions corresponding to straight ahead, right side, and left side locations for the image and/or video acquiring device, relative to the patient's face.

45. The method of claim 31, further comprising enabling a user to overlay at least one image of at least one mask system and the at least one image and/or video.

46. The method of claim 45, further comprising enabling the user to synchronize a plurality of images and/or videos from a plurality of image and/or video acquiring devices.

47. The method of claim 31, further comprising calculating a distance to and/or orientation of the patient's face, based on fixed dimensions of the at least one symbol.

48. The method of claim 47, further comprising obtaining a measurement of the patient's face based on the at least one symbol.

49. The method of claim 31, wherein the upright includes a telescopic arrangement to control height adjustment of the upright.

50. The method of claim 49, wherein telescopic movement of the upright is controlled by a pneumatic system.

51. The method of claim 49,
    wherein the telescopic arrangement includes a bushing positioned to prevent the patient from squashing his/her finger between telescoping parts.

* * * * *